(12) United States Patent
Arakawa et al.

(10) Patent No.: US 10,947,306 B2
(45) Date of Patent: *Mar. 16, 2021

(54) CORRECTLY FOLDED ETANERCEPT IN HIGH PURITY AND EXCELLENT YIELD

(71) Applicant: COHERUS BIOSCIENCES, INC., Redwood City, CA (US)

(72) Inventors: Tsutomu Arakawa, Thousand Oaks, CA (US); Douglas Farrar, Longmont, CO (US)

(73) Assignee: Coherus BioSciences, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/443,688

(22) Filed: Jun. 17, 2019

(65) Prior Publication Data

US 2019/0330325 A1 Oct. 31, 2019

Related U.S. Application Data

(63) Continuation of application No. 15/720,291, filed on Sep. 29, 2017, which is a continuation of application No. 14/023,736, filed on Sep. 11, 2013, now abandoned.

(60) Provisional application No. 61/699,552, filed on Sep. 11, 2012.

(51) Int. Cl.
| | |
|---|---|
| *A61K 39/00* | (2006.01) |
| *C07K 16/00* | (2006.01) |
| *C12P 21/08* | (2006.01) |
| *C07K 16/24* | (2006.01) |
| *C07K 14/705* | (2006.01) |
| *C07K 1/16* | (2006.01) |
| *A61K 39/395* | (2006.01) |

(52) U.S. Cl.
CPC .......... *C07K 16/241* (2013.01); *A61K 39/395* (2013.01); *C07K 1/165* (2013.01); *C07K 14/70578* (2013.01); *A61K 2039/505* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,605,690 | A | 2/1997 | Jacobs et al. |
| 7,294,481 | B1 | 11/2007 | Fung |
| 7,648,702 | B2 | 1/2010 | Gombotz et al. |
| 7,750,129 | B2 | 7/2010 | Johnsson et al. |
| 7,915,225 | B2 | 3/2011 | Finck et al. |
| 8,758,747 | B2 | 6/2014 | Kallmeyer et al. |
| 9,302,002 | B2 * | 4/2016 | Manning ................. A61K 9/16 |
| 9,393,305 | B2 * | 7/2016 | Manning ........... A61K 38/1793 |
| 9,453,067 | B2 | 9/2016 | Deutel et al. |
| 9,662,396 | B2 * | 5/2017 | Manning ................. A61K 47/02 |
| 9,770,510 | B2 * | 9/2017 | Manning ................. A61K 9/16 |
| 9,801,942 | B2 * | 10/2017 | Manning .............. A61K 38/191 |
| 9,943,601 | B2 * | 4/2018 | Manning .......... A61K 39/39591 |
| 10,213,508 | B2 * | 2/2019 | Manning ................. A61K 9/16 |
| 10,293,049 | B2 * | 5/2019 | Manning ............. A61K 9/0019 |
| 10,376,588 | B2 * | 8/2019 | Manning .............. A61K 38/191 |
| 10,485,869 | B2 * | 11/2019 | Manning .......... A61K 39/39591 |
| 10,493,151 | B2 * | 12/2019 | Manning ........... A61K 38/1793 |
| 2003/0180287 | A1 | 9/2003 | Gombotz et al. |
| 2005/0032183 | A1 | 2/2005 | Osslund et al. |
| 2006/0177444 | A1 | 8/2006 | Horizoe |
| 2006/0292148 | A1 | 12/2006 | Matsumoto |
| 2007/0196364 | A1 | 8/2007 | Krishnamurthy et al. |
| 2007/0243185 | A1 | 10/2007 | Gombotz et al. |
| 2008/0071063 | A1 | 3/2008 | Allan et al. |
| 2008/0108106 | A1 | 5/2008 | Wang et al. |
| 2008/0112953 | A1 | 5/2008 | McAuley et al. |
| 2008/0124326 | A1 | 5/2008 | Rehder et al. |
| 2008/0177048 | A1 | 7/2008 | Gagnon |
| 2008/0187544 | A1 | 8/2008 | Buckly et al. |
| 2008/0213282 | A1 | 9/2008 | Jaby et al. |
| 2008/0311119 | A1 | 12/2008 | Maloney |
| 2009/0048122 | A1 | 2/2009 | Glaser et al. |
| 2009/0068705 | A1 | 3/2009 | Drapeau et al. |

(Continued)

FOREIGN PATENT DOCUMENTS

| | | |
|---|---|---|
| CN | 1244805 A | 2/2000 |
| CN | 1829739 A | 9/2006 |

(Continued)

OTHER PUBLICATIONS

U.S. Appl. No. 16/443,594, filed Jun. 2019, Arakawa; Tsutomu.*

(Continued)

*Primary Examiner* — Thea D'Ambrosio
(74) *Attorney, Agent, or Firm* — Rothwell, Figg, Ernst & Manbeck, P.C.

(57) ABSTRACT

A mixed mode chromatography method for separating correctly folded from incorrectly folded conformations of a given protein is provided. The method is highly effective in separating correctly folded etanercept from incorrectly folded etanercept and aggregates in commercially attractive yields capable of affording etanercept preparations having very high purity in terms of correctly folded etanercept versus incorrectly folded etanercept. The invention is further directed to protein preparations and formulations comprising correctly folded proteins obtained using the present methods, and methods of treatment using the high purity preparations obtained from the mixed mode method.

22 Claims, 26 Drawing Sheets

(56) References Cited

U.S. PATENT DOCUMENTS

| | | |
|---|---|---|
| 2009/0117097 A1 | 5/2009 | Igawa et al. |
| 2009/0163424 A1 | 6/2009 | Finck et al. |
| 2009/0291062 A1 | 11/2009 | Fraunhofer et al. |
| 2010/0158908 A1 | 6/2010 | Rehder et al. |
| 2010/0166774 A1 | 7/2010 | Dali et al. |
| 2011/0065901 A1 | 3/2011 | Soice et al. |
| 2011/0091936 A1 | 4/2011 | Gawlitzek et al. |
| 2011/0129468 A1 | 6/2011 | McCue et al. |
| 2011/0144302 A1 | 6/2011 | Jarstad et al. |
| 2012/0208986 A1 | 8/2012 | Wenger et al. |
| 2013/0101583 A1* | 4/2013 | Manning .......... A61K 39/39591 424/134.1 |
| 2013/0101584 A1 | 4/2013 | Manning |
| 2013/0101640 A1 | 4/2013 | Manning |
| 2013/0108632 A1 | 5/2013 | Manning et al. |
| 2013/0108633 A1 | 5/2013 | Manning |
| 2013/0108634 A1* | 5/2013 | Manning .......... A61K 39/39591 424/134.1 |
| 2013/0150554 A1 | 6/2013 | Melville et al. |
| 2013/0224855 A1 | 8/2013 | Gupta et al. |
| 2014/0187751 A1* | 7/2014 | Nti-Gyabaah ........... C07K 1/36 530/387.3 |
| 2014/0199303 A1 | 7/2014 | Choi et al. |
| 2014/0248274 A1 | 9/2014 | Kallmeyer et al. |
| 2014/0255400 A1* | 9/2014 | Maloney .......... C07K 14/70578 424/134.1 |
| 2015/0125532 A1* | 5/2015 | Manning ................ A61K 9/14 424/489 |
| 2016/0108634 A1 | 4/2016 | Uphold et al. |
| 2018/0037642 A1* | 2/2018 | Arakawa .............. C07K 16/241 |
| 2018/0125982 A1* | 5/2018 | Manning ................ A61K 38/17 |
| 2019/0184017 A1* | 6/2019 | Manning .................. A61K 9/08 |
| 2019/0300600 A1* | 10/2019 | Arakawa .............. C07K 16/241 |
| 2019/0300601 A1* | 10/2019 | Arakawa .............. C07K 16/241 |

FOREIGN PATENT DOCUMENTS

| | | | |
|---|---|---|---|
| CN | 101237890 A | 8/2008 | |
| CN | 101969971 A | 2/2011 | |
| CN | 102239177 A | 11/2011 | |
| CN | 103930124 A | 7/2014 | |
| EA | 201490195 A1 | 4/2014 | |
| EA | 201391739 A1 | 5/2014 | |
| EP | 0 420 649 A2 | 4/1991 | |
| EP | 1314 437 A1 | 5/2003 | |
| EP | 1478394 A2 | 11/2004 | |
| EP | 1607103 A1 | 12/2005 | |
| EP | 1908482 A1 | 4/2008 | |
| EP | 1 478 394 B1 | 7/2008 | |
| ES | 2311094 T3 | 2/2009 | |
| JP | 2005-527503 | 5/2005 | |
| JP | 2005527503 A | 9/2005 | |
| JP | 2009521482 A | 6/2009 | |
| JP | 2009-525986 | 7/2009 | |
| JP | 2009534390 A | 9/2009 | |
| JP | 20100506911 A | 3/2010 | |
| JP | 2010513522 A | 4/2010 | |
| JP | 2010517942 A | 5/2010 | |
| JP | 2010529999 A | 9/2010 | |
| JP | 2014518276 A | 7/2014 | |
| JP | 2014519484 A | 8/2014 | |
| JP | 2014522402 A | 9/2014 | |
| TW | 200510453 A | 3/2005 | |
| TW | 201311293 A1 | 3/2013 | |
| TW | I595883 | 8/2017 | |
| TW | I619504 | 4/2018 | |
| WO | 9406476 A1 | 3/1994 | |
| WO | 1998022136 A2 | 3/1998 | |
| WO | 00/62790 A2 | 10/2000 | |
| WO | 0158473 A1 | 8/2001 | |
| WO | 03/072060 A2 | 9/2003 | |
| WO | 2003072060 A2 | 9/2003 | |
| WO | 2004017955 A1 | 3/2004 | |
| WO | 2004075918 A1 | 9/2004 | |
| WO | 2005/012353 A1 | 2/2005 | |
| WO | 2005012353 A1 | 2/2005 | |
| WO | 2005/037214 A2 | 4/2005 | |
| WO | 2005/082377 A1 | 9/2005 | |
| WO | 2005/095578 A1 | 10/2005 | |
| WO | 2006/026447 A2 | 3/2006 | |
| WO | 2006132363 A1 | 12/2006 | |
| WO | 2007/076354 A2 | 7/2007 | |
| WO | 2007076062 A2 | 7/2007 | |
| WO | 2007/092772 A2 | 8/2007 | |
| WO | 2007124082 A2 | 11/2007 | |
| WO | 2008045373 A2 | 4/2008 | |
| WO | 2008051363 A2 | 5/2008 | |
| WO | 2008/086335 A | 7/2008 | |
| WO | 2008079290 A2 | 7/2008 | |
| WO | 2008/152075 A1 | 12/2008 | |
| WO | 2008157356 A2 | 12/2008 | |
| WO | 2009/111347 A1 | 9/2009 | |
| WO | 2011/015926 A1 | 2/2011 | |
| WO | 2011049798 A1 | 4/2011 | |
| WO | WO-2011049798 A1 * | 4/2011 | ........... B01D 15/362 |
| WO | 2011079308 A1 | 6/2011 | |
| WO | 2011/134920 A1 | 11/2011 | |
| WO | 2011/141926 A2 | 11/2011 | |
| WO | 2011141926 A2 | 11/2011 | |
| WO | 2012/013980 A1 | 2/2012 | |
| WO | WO-2012051147 A1 * | 4/2012 | ........... C12M 47/12 |
| WO | 2012/143418 A1 | 10/2012 | |
| WO | 2012143418 A1 | 10/2012 | |
| WO | 2013006454 A1 | 10/2012 | |
| WO | WO-2012143418 A1 * | 10/2012 | ............. A61K 47/12 |
| WO | 2012165917 A1 | 12/2012 | |
| WO | 2013/006454 A1 | 1/2013 | |
| WO | 2013/006479 A2 | 1/2013 | |
| WO | WO-2013006454 A1 * | 1/2013 | ......... A61K 38/1793 |

OTHER PUBLICATIONS

U.S. Appl. No. 16/443,514, filed Jul. 2019, Arakawa; Tsutomu.*
"THPdb: A Database of FDA approved Therapeutic Peptides and Proteins" available online at http://crdd.osdd.net/raghava/thpdb/display_thppid_sub.php?details=Th1005, 7 pages (accessed on Jan. 10, 2020) (Year: 2020).*
Arakawa et al., Prot. Expr. Purif. 63:158-163 (2009) (Year: 2009).*
Gagnon et al., Bioprocess Int. 8:26-35 (2010) (Year: 2010).*
Taiwanese Office Action with Search Report dated Nov. 5, 2018, 10 pages.
Translation of Examination Report for corresponding Japanese Patent Application No. 2014537220 dated Jun. 21, 2016.
Examination Report for corresponding Singaporean Patent Application No. 11201401562R dated Jan. 16, 2016.
Translation of Search Report for corresponding Taiwanese Patent Application No. 101138560 dated Jun. 27, 2016.
Translation of Examination Report for corresponding Chinese Patent Application No. 201280062761.9 dated Apr. 3, 2015.
Translation of Examination Report for corresponding Chinese Patent Application No. 201280062761.9 dated Jan. 29, 2016.
Translation of Examination Report for corresponding Chinese Patent Application No. 201280062761.9 dated Jul. 21, 2016.
Translation of Examination Report for corresponding Eurasian Patent Application No. 201490802 dated May 14, 2015.
Translation of Examination Report for corresponding Eurasian Patent Application No. 201490802 dated Feb. 29, 2016.
Examination Report for corresponding European Patent Application No. 12841505.6 dated Jan. 28, 2015.
Translation of Examination Report for corresponding Japanese Patent Application No. 2014537221 dated Jun. 21, 2016.
Translation of Search Report for corresponding Taiwanese Patent Application No. 101138566 dated Mar. 3, 2016.
Examination Report for corresponding Australian Patent Application No. 2012326082 dated Aug. 16, 2016.
Translation of Examination Report for corresponding Chinese Patent Application No. 201280062739.4 dated Mar. 30, 2015.
International Search Report and Written Opinion for corresponding PCT application No. PCT/US2012/060738 dated Jan. 7, 2013.

(56) References Cited

OTHER PUBLICATIONS

Translation of Examination Report for corresponding Chinese Patent Application No. 201280062739.4 dated Jan. 29, 2016.
Translation of Examination Report for corresponding Eurasian Patent Application No. 201490803 dated Jun. 4, 2015.
Translation of Examination Report for corresponding Eurasian Patent Application No. 201490803 dated Feb. 12, 2016.
Examination Report for corresponding European Patent Application No. 12842312.6 dated Jan. 28, 2015.
Translation of Examination Report for corresponding Japanese Patent Application No. 2014537222 dated Jun. 21, 2016.
Translation of Search Report for corresponding Taiwanese Patent Application No. 101138567 dated Dec. 24, 2015.
Examination Report for corresponding Australian Patent Application No. 2012326084 dated Aug. 16, 2016.
Translation of Examination Report for corresponding Chinese Patent Application No. 201280062418.4 dated Jan. 30, 2015.
Translation of Examination Report for corresponding Chinese Patent Application No. 201280062418.4 dated Sep. 15, 2015.
Translation of Examination Report for corresponding Eurasian Patent Application No. 201490801 dated Jun. 4, 2015.
Translation of Examination Report for corresponding Eurasian Patent Application No. 201490801 dated Oct. 15, 2015.
English language translation of Examination Report for corresponding Japanese Patent Application No. 2014-537218 dated Jul. 26, 2016.
English language translation of Examination Report for corresponding Taiwanese Patent Application No. 101138560 dated Jun. 23, 2016.
Examination Report for corresponding Australian Patent Application No. 2013290289 dated Mar. 27, 2017.
English language translation of Examination Report for corresponding Bolivian Patent Application No. SP 0207-2013 dated Nov. 10, 2014.
English language translation of Examination Report for corresponding Bolivian Patent Application No. SP 0207-2013 dated Feb. 15, 2016.
English language translation of Examination Report for corresponding Chilean Patent Application Chile Nr. 0051-2015 dated Jan. 27, 2016.
English language translation of Examination Report for corresponding Eurasian Patent Application 201590161 dated Jan. 27, 2016.
English language translation of Examination Report for corresponding Japanese Patent Application 2015-521752 dated Apr. 4, 2017.
English language translation of Examination Report for corresponding Chilean Patent Application CL0572-2015 dated Aug. 22, 2016.
English language translation of Examination Report for corresponding Chinese Patent Application CN201380058650.5 dated Apr. 26, 2016.
English language translation of Examination Report for corresponding Colombian Patent Application CO15076746 dated Oct. 9, 2017.
EP Examination Report issued for EP14776207.4 dated May 27, 2016.
Tellez, CM, et al., Method for the characterization of size-exclusion chromatography media for preparative purification of DNA restriction fragments, Jun. 1999, Biotechnology Techniques, 13(6), 395-401.
Caporali R, et al., Diffuse skin reaction after changing the etanercept formulation, Nov. 1, 2008, Clinical and Experimental Rheumatology, 26(6), 1165.
Gokarn YR, et al., Excipients for protein drugs, Excipient development for pharmaceutical, biotechnology, and drug delivery systems, Jan. 1, 2006, 291-331.
Niazi, SK. "Enbrel" Handbook of pharmaceutical manufacturing formulations: Sterile products, 2009, 410.
Gazerani, Pet al., Effects of subcutaneous administration of glutamate on pain, sensitization and vasomotor responses in healthy men and women, Pain, Oct. 2006, 124(3), 338-348.

Bolli, R. et al., L-Proline reduces IgG dimer content and enhances the stability of intravenous immunoglobulin (IVIG) solutions, Biologicals, Jan. 2010, 38(1), 150-157.
EP Examination Report issued for EP15742902.8 dated Jun. 6, 2017.
Falconer R.J., et al., Stabilization of a monoclonal antibody during purification and formulation by addition of basic amino acid excipients, J Chem Technol Biotechnol, 2011, 86, 942-948.
Chari, R., et al., Long- and short-range electrostatic interactions affect the rheology of highly concentrated antibody solutions, Pharm. Res., Dec. 2009, 26(12), 2607-2618.
Chaudhri A, et al., Coarse-grained modeling of the self-association of therapeutic monoclonal antibodies, J Phys Chem B, Jul. 19, 2012, 116(28), 8045-8057.
Chaudhri A. et al., The role of amino acid sequence in the self-association of therapeutic monoclonal antibodies insights from coarse-grained modeling, J Phys Chem B, Feb. 7, 2013, 117(5), 1269-1279.
EP Examination Report issued for EP15742902.8 dated Mar. 1, 2018.
Buck, P.M. et al., Highly viscous antibody solutions are a consequence of network formation caused by domain-domain electrostatic complementarities: insights from coarse-grained simulations, Mol Pharm, Jan. 5, 2015, 12(1), 127-139.
English language translation of Examination Report for corresponding Singapore Patent Application SG11201605860S dated May 24, 2017.
Light Metals 2008, edited by: David H. DeYong, 875-880 (1).
Heidemann, R. et al.,The use of peptones as medium additives for the production of a recombinant therapeutic protein in high density perfusion cultures of mammalian cells, Cytotechnology, 2000, 32: 157-167.
Hossler, P. et al., Review: Optimal and consistent protein glycosylation in mammalian cell culture, Glycobiology, 2009, vol. 19, No. 9, pp. 936-949.
Altamirano, C. et al., Strategies for fed-batch cultivation of t-PA producing CHO cells: substitution of glucose and glutamine and rational design of culture medium, Journal of Biotechnology, 2004, 110: 171-179.
Bonarius, H. et al., Metabolic-Flux Analysis of Continuously Cultured Hybridoma Cells Using 13CO2 Mass Spectrometry in Combination with 13C-Lactate Nuclear magnetic Resonance Spectroscopy and Metabolite Balancing, Biotechnology and Bioengenieering, 2001, vol. 74, No. 6, pp. 528-538.
Reinhart D. et al., Benchmarking of commercially available CHO cell culture media for antibody production. BMC Proceedings, Dec. 4, 2013, vol. 7, No. Supp 6, pp. 13.
Examination Report for corresponding European Patent Application No. 12841765.6 dated Feb. 5, 2015.
Translation of Examination Report for corresponding Japanese Patent Application No. 2014537223 dated Jun. 21, 2016.
Examination Report for corresponding Singaporean Patent Application No. 11201401517V dated Sep. 21, 2015.
Translation of Search Report for corresponding Taiwanese Patent Application No. 101138564 dated May 26, 2016.
International Search Report and Written Opinion for corresponding PCT Application No. PCT/US2012/060739 dated Dec. 7, 2012.
International Search Report and Written Opinion for corresponding PCT Application No. PCT/US2012/060741 dated Jan. 18, 2013.
International Search Report and Written Opinion for corresponding PCT Application No. PCT/US2012/060743 dated Jan. 18, 2013.
International Search Report and Written Opinion for corresponding PCT Application No. PCT/US2012/060745 dated Jan. 18, 2013.
International Search Report and Written Opinion for corresponding PCT Application No. PCT/US2012/060748 dated Jan. 3, 2013.
Examination Report for corresponding Australian Patent Application No. 2012326168 dated Aug. 17, 2016.
Translation of Examination Report for corresponding Chinese Patent Application No. 201280062758.7 dated Jun. 30, 2015.
Translation of Examination Report for corresponding Eurasian Patent Application No. 201490815 dated Jun. 4, 2015.
Examination Report for corresponding European Patent Application No. 12842226.8 dated Jan. 28, 2015.

(56) References Cited

OTHER PUBLICATIONS

Translation of Examination Report for corresponding Israeli Patent Application No. 231824 dated Jun. 14, 2016.
Translation of Examination Report for corresponding Taiwanese Patent Application No. 101138561 dated Feb. 15, 2016.
Examination Report for corresponding Australian Patent Application No. 2012326170 dated Aug. 18, 2016.
Translation of Examination Report for corresponding Chinese Patent Application No. 201280062747.9 dated Jan. 27, 2015.
Translation of Examination Report for corresponding Chinese Patent Application No. 201280062747.9 dated Oct. 21, 2015.
Translation of Examination Report for corresponding Chinese Patent Application No. 201280062747.9 dated May 16, 2016.
Examination Report for European Patent Application No. 12842352.2 dated Jun. 8, 2015.
Translation of Examination Report for corresponding Japanese Patent Application No. 2014537219 dated Jul. 19, 2016.
Examination Report for corresponding Singaporean Patent Application No. 11201401563S dated Jan. 20, 2016.
Translation of Examination Report for corresponding Taiwanese Patent Application No. 101138565 dated May 24, 2016.
Examination Report for corresponding Australian Patent Application No. 2012326171 dated Aug. 22, 2016.
Translation of Examination Report for corresponding Chinese Patent Application No. 201280062748.3 dated Feb. 5, 2015.
Translation of Examination Report for corresponding Chinese Patent Application No. 201280062748.3 dated Dec. 3, 2015.
Translation of Examination Report for corresponding Eurasian Patent Application No. 201490804 dated May 25, 2015.
Translation of Examination Report for corresponding Eurasian Patent Application No. 201490804 dated Jan. 26, 2015.
Examination Report for corresponding European Patent Application No. 12841522.1 dated Jan. 28, 2015.
De Groot et al. "Immunogenicity of protein therapeutics", ScienceDirect, vol. 28, No. 11, 2007.
Dore et al., "The immunogenicity, safety, and efficacy of etanercept liquid administered once weekly in patients with rheumatoid arthritis", Clinical and Experiemental Rheumatology, vol. 25 p. 40-46, 2007.
Enbrel, Highlights of Prescribing Information, Dec. 2012, Reference ID: 3225283.
Enbrel, Physician Package Insert, 10662-12+Kineret combo, 2003.
Enbrel (etanercept), 2004.
Enbrel (etanercept), for Subcutaneous Injection, 2004.
Enbrel (etanercept), for Subcutaneous Injection, Revised PI submitted by the sponsor—Final Draft, May 20, 2005.
Enbrel (etanercept), for Subcutaneous Injection, Wegener's Updated Revision; Jul. 20, 2005.
Hoshino et al., Influence of antiboides against infliximab and etanercept on the treatment effectiveness of these agents in Japanese patients with rheumatoid arthritis, Mod Rheumatol (2012) 22:532-540; DOI 10.1007/s10165-011-0567-8.
Van Maarschalkerweerd et al., "Conparison of analytical methods to detect instability of etanercept during thermal stress testing", European Journal of Pharmaceutics and Biopharmaceutics 78 (2011) 213-221.
Sullivan et al., "Bioequivalence of Liquid and Reconstituted Lyophilized Etanercept Subcutaneous Injections", J Clin Pharmacol 2006; 46:654-661.
Zhou, "Clinical Pharmacokinetics of Etanercept: A Fully Humanized Soluble Recombinant Tumor Necrosis Factor Receptor Fusion Protein", J Clin Pharmacol, 2005; 45:490-497.
Maas et al., "A Role for Protein Misfolding in Immunogenicity of Biopharmaceuticals" Journal of Biological Chemistry, vol. 282, No. 4. pp. 2229-2236, Nov. 29, 2006.
Search Report for corresponding PCT application PCT/US13/58994.
Lees et al., "Purifying a Recalcitrant Therapeutic Recombinant Protein with a Mixed-Mode Chromatography Sorbent," BioProcess Intl. 7(2):2-6 (2009).
Lipsky et al., "Infliimab and Methotrexote in the treatment of Pheumatoid Arthritis," New Engl. J. Med. 343; 1594-1602 (2000).
C. Challener, "Excipient Selection for Protein Stabilization," Pharmaceutical Technology APIs, Excipients, and Manufacturing Supplement, 2015, vol. 39; No. 18, pp. s35-s39.
C. Challener, "Fusion Proteins Pose Manufacturability Challenges," BioPharm International, 2017, vol. 30, No. 5, pp. 30-31, 37.
S. Goswami et al., "Developments and Challenges for mAb-Based Therapeutics," Antibodies, 2013, vol. 2, No. 3 pp. 452-500.
N. A. Kim, et al., "Effects of pH and Buffer Concentration on the Thermal Stability of Etanercept Using DSC and DLS," Biol. Pharm. Bull., 2014, vol. 37 No. 5, pp. 808-816.
S. Mathonet et al., "A Biopharmaceutical Industry Perspective on the Control of Visible Particles in Biotechnology-Derived Injectable Drug Products," PDA Journal of Pharmaceutical Science and Technology, 2016, vol. 70, No. 4, pp. 392-408.
S. Shire, et al., "Challenges in the Development of High Protein Concentration Formulations," Journal of Pharmaceutical Sciences, 2004, vol. 93, No. 6, pp. 1390-1402.
W. Wang, et al., "Antibody Structure, Instability, and Formulation," Journal of Pharmaceutical Sciences, 2007, vol. 96, No. 1, pp. 1-26.
J. Cleland, et al., "Formulation and Delivery of Proteins and Peptides: Design and Development Strategies," Ch. 1 in Formulation and Delivery of Proteins and Peptides, ACS Symposium Series 567, 1-19 (1994).
Chi et al., "Physical Stability of Proteins in Aqueous Solution: Mechanism and Driving Forces in Nonnative Protein Aggregation," Pharm. Res. 20: 1325-1336 (2003).
Bai et al., "Protein folding liquid chromatography," Methods Mol. Biol., 2011; 705: 69-85; doi: 10.1007/978-1-61737-967-3.5; available at http://www.ncbi.nlm.nih.gov/pubmed/21125381.
Gagnon, "IgG Aggregate Removal by Charged-Hydrophobic Mixed Mode Chromatography," Current Pharmaceutical Biotechnology, 2009, vol. 10, No. 4, pp. 434-439.
Capto MMC instructions, GE Healthcare Life Sciences, Mar. 2012, 28 pages.
Capto Adhere Instructions, GE Healthcare Life Sciences, Feb. 2012, 40 pages.
Office Action issued for Colombian Patent Application No. NC2018/0004886 dated May 22, 2019, along with English translation, 24 pages.
Office Action issued for Indian Patent Application No. 452/KOLNP/2015 dated Jun. 6, 2019, along with English translation, 7 pages.
Office Action issued for Canadian Patent Application No. 2,882,551 dated Jul. 9, 2019, 4 pages.
Office Action issued for Australian Patent Application No. 2018247244 dated Aug. 8, 2019, 5 pages.
Tsutomu Arakawa, Role of Arginine in Development of Biopharmaceuticals, Yakugaku Zasshi, 2010, vol. 130, pp. 793-800 (Abstract).
Translation of Notice of Rejection (1st Official Action) cited in Japanese Patent Application No. 2018-192476 dated Nov. 12, 2019, 6 pages.
Translation of Dominican Patent Office Action cited in Application No. P2015-0055, dated Nov. 12, 2019, 5 pages.
Evans et al., "Purification of an Fc-fusion biologic: Clearance of multiple product related impurities by hydrophobic interaction chromatography", J. Chromatography. A, 2008, 1177(2), pp. 265-271, (abstract only).
Queiroz et al., "Hydrophobic interaction chromatography of proteins", J. Biotechnol., 2001, 87(2), pp. 143-159, (abstract only).
Justin T. McCue, "Chapter 25 Theory and Use of Hydrophobic Interaction Chromatography in Protein Purification Applications", Methods Enzymol., 2009, 463, pp. 405-414, (abstract only).
Coffman et al., "High-throughput screening of chromatographic separations: I. Method development and column modeling", Biotechnol and Bioeng., 2008,100(4), pp. 605-618, (abstract only).
Tiwari et al., "Identification and characterization of native proteins of *Escherichia coli* BL-21 that display affinity towards Immobilized Metal Affinity Chromatography and Hydrophobic Interaction Chromatography Matrices", Protein Expr. Purif., 2010, 70(2), pp. 191-195, (abstract only).

(56) References Cited

OTHER PUBLICATIONS

Zolodz et al., "Separation by hydrophobic interaction chromatography and structural determination by mass spectrometry of mannosylated glycoforms of a recombinant transferrin-exendin-4 fusion protein from yeast", J. Chromatography. A, 2010, 1217(2), pp. 225-234, (abstract only).

Heller, Regine et al, "L• ascorbic acid potentiates endothelial nitric oxide synthesis via a chemical stabilization of Tetrahydroiopterin.", Journal of Biological Chemistry, (Jan. 5, 2001) vol. 276, No. 1, pp. 40-47.

Jennissen, "Hydrophobic Interaction chromatography: harnessing multivalent protein-surface Interactions for purification procedures.", Methods in Molecular Biology (Clifton, N.J.)2005, (2005), vol. 305, pp. 81-99.

Josics et al, "Purification of Monoclonal Antibodies by Hydroxylapatite HPLC and Size Exclusion HPLC", Biol. Chem. Hoppe-Seylars, (1991), vol. 372, pp. 149-156.

Office Action issued for Argentina No. P130103250 dated Nov. 5, 2019, along with English translation, 4 pages.

Aoyama, K.; Chiba, J., Separation of Different Molecular Forms of Mouse IgA and IgM Monoclonal Antibodies in High-Performance Liquid Chromatography on Spherical Hydroxyapatite Beads, J. Immunol. Methods, (1993),vol. 162, pp. 201-210.

Notice of Preliminary Rejection cited in Korean Patent Application No. 10-2015-7009386 dated Jul. 22, 2019 with translation, 17 pages.

Baynes et al., Role of Arginine in the Stabilization of Proteins against Aggregation. Biochem. Mar. 29, 2005;44(12):4919-25.

Bolli et al., L-Proline reduces IgG dimer content and enhances the stability of intravenous immunoglobulin (IVIG) solutions. Biologicals. Jan. 2010;38(1): 150-7.

Kolhe et al., Impact of Freezing on pH of Buffered Solutions and Consequences for Monoclonal Antibody Aggregation. Biotechnol Prog. May-Jun. 2010;26(3):727-33.

Shiraki et al., Biophysical Effect of Amino Acids on the Prevention of Protein Aggregation. J Biochem. Oct. 2002;132(4):591-5.

Zheng et al., Influence of pH, buffer species, and storage temperature on physiochemical stability of a humanized monoclonal antibody LA298. Int J Pharm. Feb. 3, 2006;308(1-2):46-51.

Handa, Medicine Update, pp. 270-275 (2011) (Year 2011).

FDA News Release, "FDA approves Erelzi, a biosimilar to Enbrel," available online at https://www.fda.gov/NewsEvents/Newsroom/PressAnnouncements/ucm518639.htm, 2 pages (2016) (Year 2016).

TheBalance, "What Is a Biobetter?," available online at https://www.thebalance.com/biobetter-definition-3895896, 3 pages (2016) (Year: 2016).

FDA Arthritis Advisory Committee, "Enbrel® (etanercept)," available online at https://www.fda.gov/ohrms/dockets/ac/01/briefing/3779b2_02_immunex.pdf, 55 pages at p. 31, 2nd paragraph (2001) (Year 2001).

IJPC, Inc., "Tonicity Adjustment Database," available online at https://compoundingtoday.com/TonicityAdjust/, 2 pages (2006) (Year: 2006).

\* cited by examiner

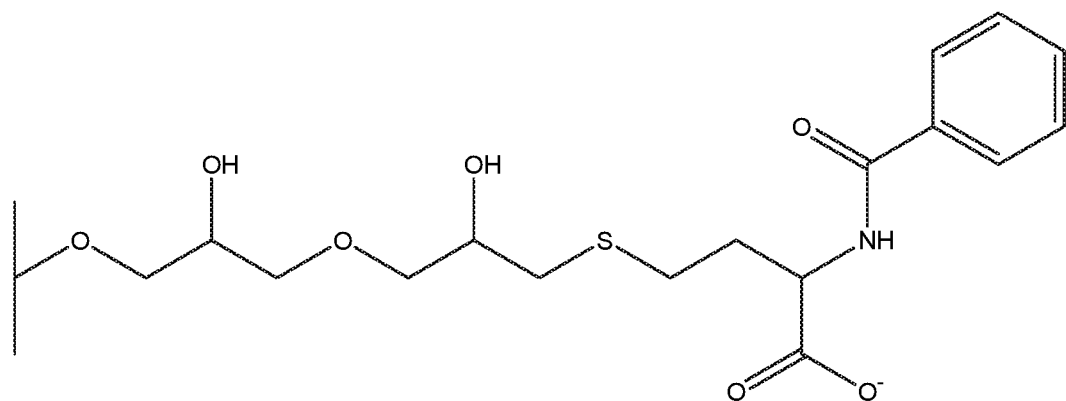
Capto MMC
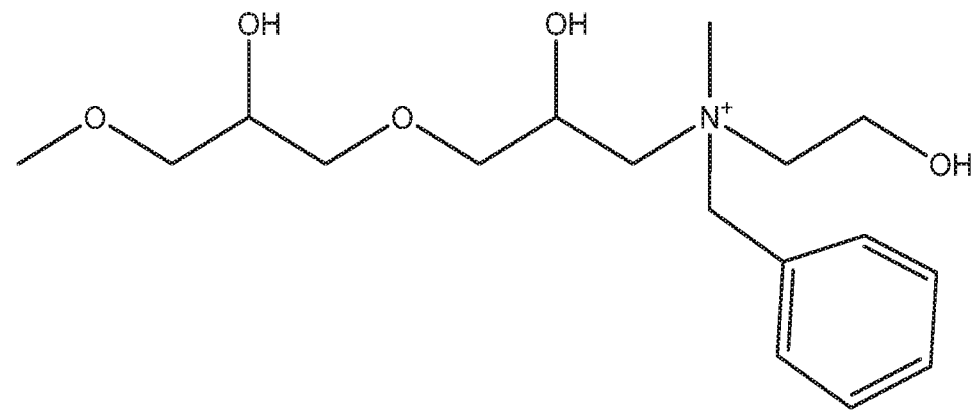
Capto Adhere
Fig. 1

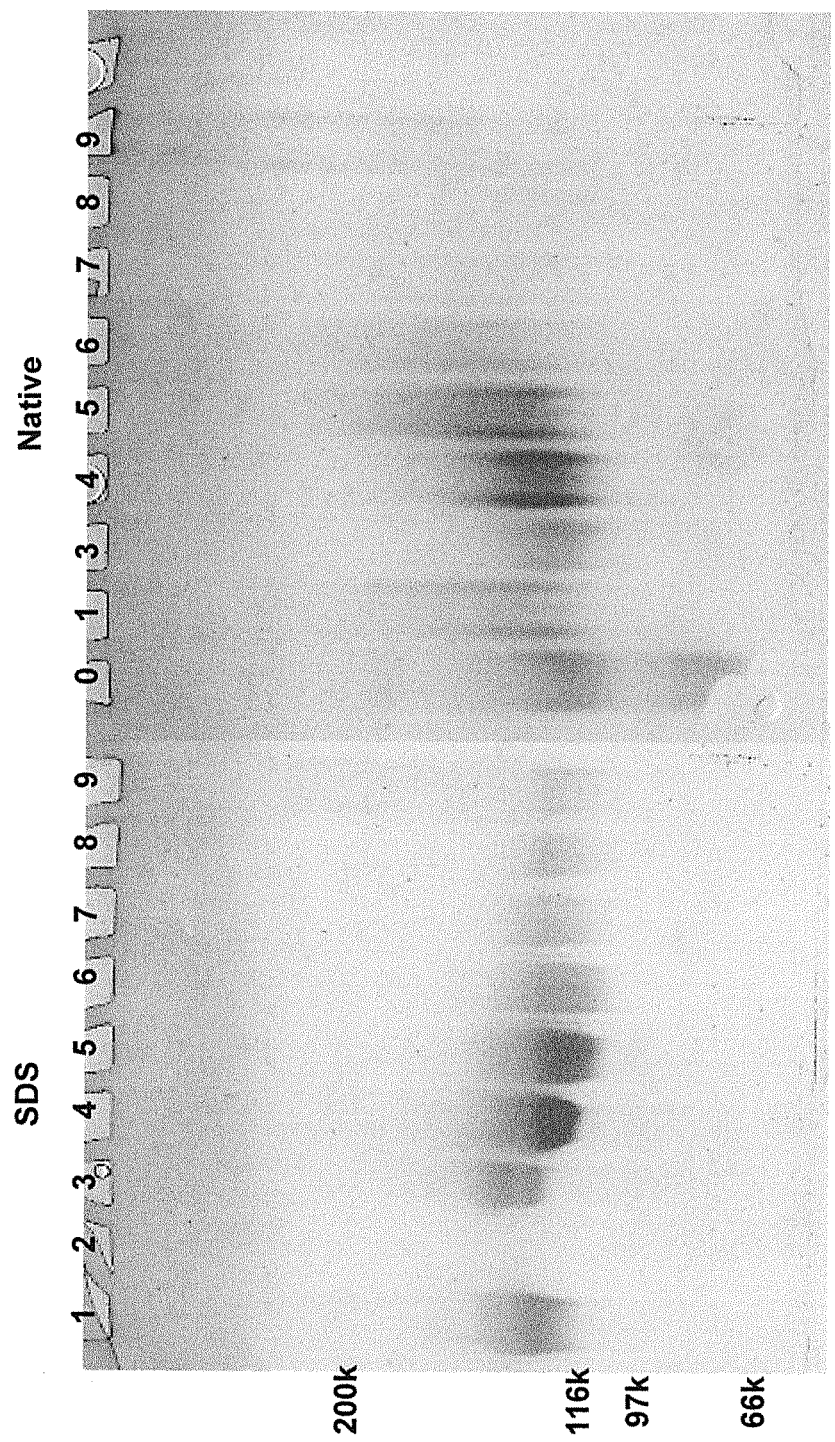

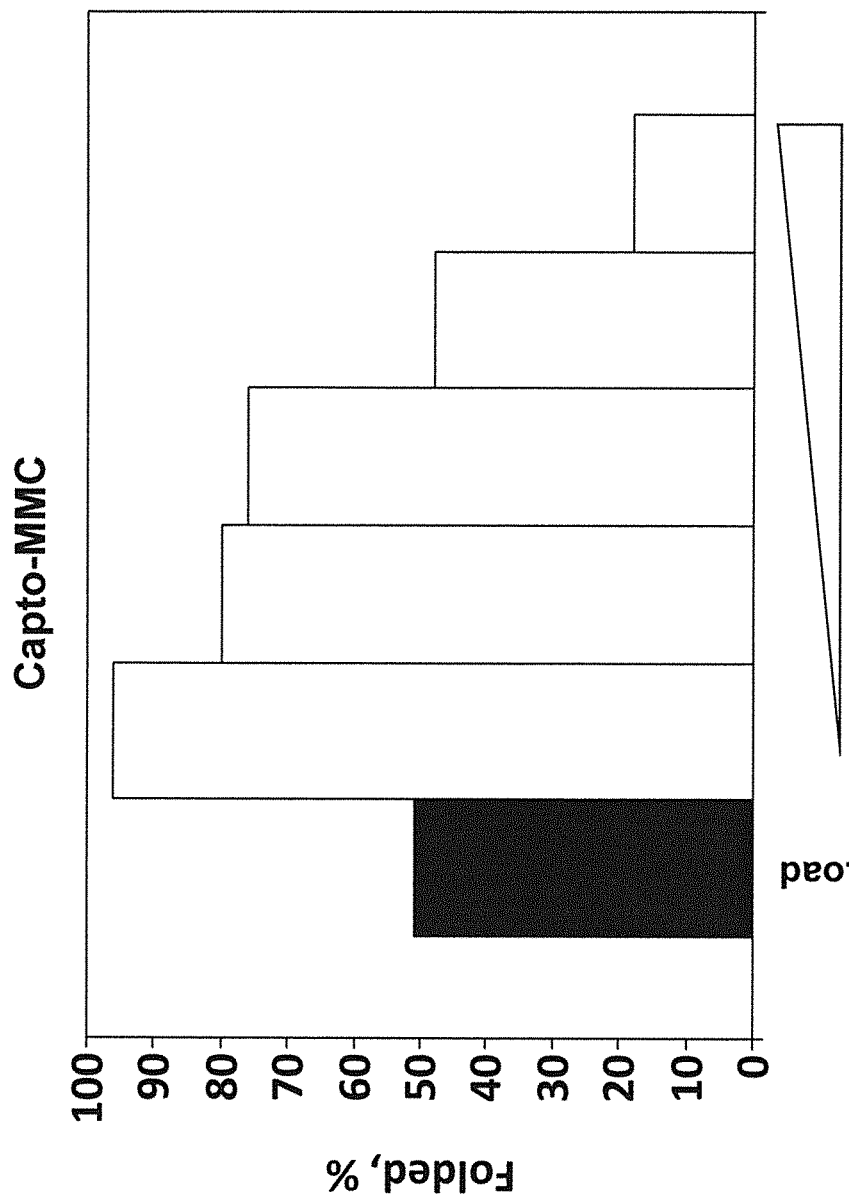

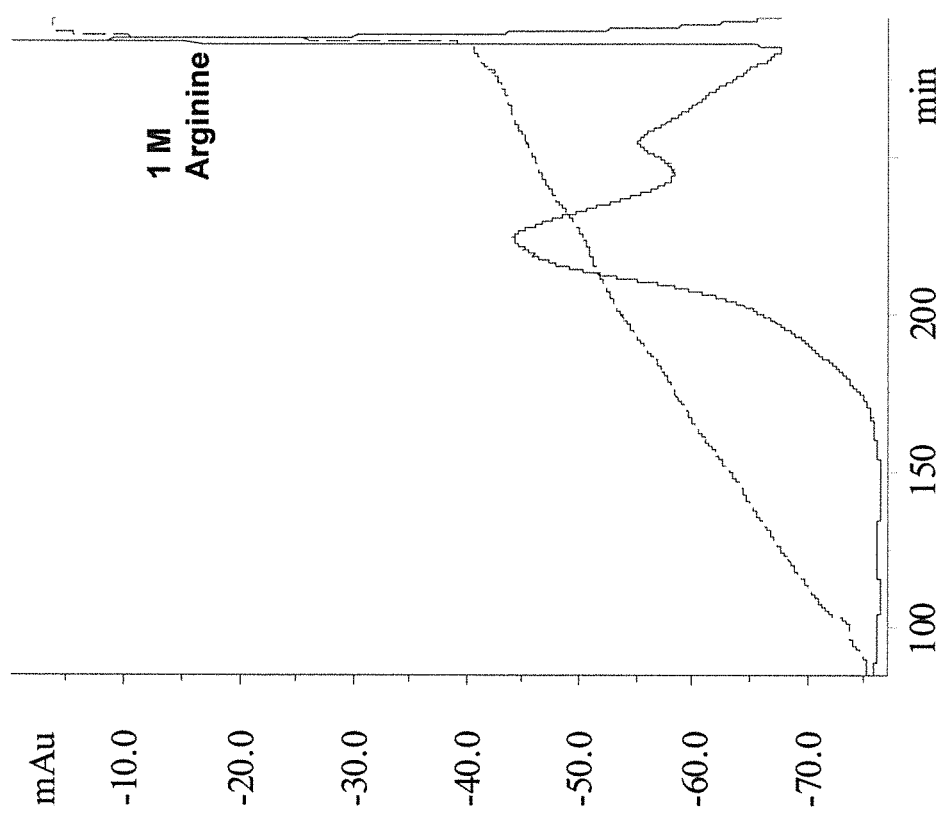

CORRECTLY FOLDED ETANERCEPT IN HIGH PURITY AND EXCELLENT YIELD

CROSS-REFERENCE TO RELATED APPLICATIONS

This application is a continuation of U.S. application Ser. No. 15/720,291, filed Sep. 29, 2017, which is a continuation of U.S. application Ser. No. 14/023,736, filed Sep. 11, 2013, which claims priority benefit of U.S. provisional Appl. Ser. No. 61/699,552, filed Sep. 11, 2012, the disclosures of which are incorporated herein by reference in their entireties.

FIELD OF THE INVENTION

The present invention relates generally to chromatographic separation methods for purifying recombinantly expressed proteins, and products obtained from such methods. More particularly, it relates to use of mixed mode chromatography to purify a recombinant protein expression product, including, for example, fusion proteins which may include undesired amounts of incorrectly folded and/or aggregated protein along with properly folded protein. The mixed-mode chromatography method of the invention is especially useful for separating correctly folded etanercept from incorrectly folded etanercept (as defined herein). The invention is also directed to etanercept preparations and pharmaceutical formulations wherein the etanercept supplied therein has been produced in high yield and high purity using the disclosed method. The invention further concerns treatment methods for TNF conditions employing highly purified etanercept characterized by remarkably low levels of misfolded/aggregated protein.

BACKGROUND OF THE INVENTION

Etanercept (Enbrel®, manufactured by Immunex Corporation) is a dimeric fusion polypeptide consisting of the extracellular ligand-binding portion of the human 75 kilodalton (p75) tumor necrosis factor receptor ("TNFR") linked to the Fc receptor [fragment, crystallizable] region of human Immunoglobulin G ("IgG1"). Etanercept consists of 934 amino acids and has an apparent molecular weight of approximately 150 kilodaltons (Physicians Desk Reference, 2002, Medical Economics Company, Inc.). The Fc component of etanercept contains the constant heavy 2 (CH2) domain, the constant heavy 3 (CH3) domain and hinge region, but not the constant heavy 1 (CH1) domain of human IgG1. An Fc domain can contain one or all of the domains described above.

People suffering from some types of inflammatory diseases such as rheumatoid arthritis, plaque psoriasis, psoriatic arthritis, juvenile idiopathic arthritis, and ankylosing spondylitis, have an immune system that over produces tumor necrosis factor ("TNF"). Administration of etanercept has been found effective for treatment of some inflammatory diseases because it can reduce the levels of the active form of TNF in a subject by binding to TNF as a decoy receptor.

Etanercept can be produced in a known manner by recombinant DNA technology in a Chinese hamster ovary ("CHO") mammalian cell expression system. Unfortunately, the product that is produced by the CHO cells contains a large amount of incorrectly or misfolded and/or aggregated etanercept. For pharmaceutical use, it is desirable to provide etanercept that is relatively free of incorrectly folded and aggregated protein because the incorrectly folded/aggregated protein will not have the same therapeutic effect as the correctly folded protein, and may actually be detrimental to the patient.

Misfolding and aggregation frequently occur during production of recombinant proteins and hence must be addressed through downstream processes capable of separating the correctly folded protein from protein that is misfolded or aggregated. Misfolding reduces or eliminates the therapeutic effect of the protein. Aggregation, generally understood to involve non-covalent association of two or more etanercept homodimers to form very high molecular weight species, results in a similar loss of therapeutic effect, and occurs when proteins, including misfolded proteins, accumulate and clump together. As stated above, such misfolded proteins and protein aggregates are not only therapeutically ineffective, but may also be detrimental to the patient. Accordingly, the ability to purify a protein expression product containing etanercept so that properly folded etanercept is separated from misfolded and/or aggregated etanercept is important for obtaining etanercept that provides the highest possible degree of pharmaceutical acceptability.

Production of misfolded and aggregated proteins is not a problem specific to etanercept. There are many therapeutic proteins for which misfolding may be a problem. For example, misfolding of disulfide-containing proteins during refolding of recombinant proteins from *Escherichia coli* inclusion bodies is difficult to avoid, but can be effectively separated by reverse-phase chromatography with high resolution. The use of low pH and organic solvent in reverse-phase chromatography, however, can denature the proteins and may cause aggregation of the purified protein during the chromatography.

Even when misfolding is thought to be negligible during production of pharmaceutical proteins, e.g., in the case of mammalian secretory expression, aggregation and some misfolding may still occur (see e.g., Chi, E. Y., Krishnan, S., Randolph, T. W. and Carpenter, J. F., *Physical Stability of Proteins in Aqueous Solution: Mechanism and Driving Forces in Nonnative Protein Aggregation*, Pharm. Res., 20, 1325-1336 (2003); Kiese, S., Pappenberger, A., Friess, W., and Mahler, H. C., *Shaken, Not Stirred: Mechanical Stress Testing of an IgG1 Antibody*, J. Pharm. Sci., 97, 4347-4366 (2008)). Researchers have successfully separated non-native, misfolded proteins under non-denaturing conditions using aqueous chromatography employing ion exchange ("IEC") (see, e.g., Gagnon, P. J., *Antibody Aggregate Removal by Hydroxyapatite Chromatography in the Presence of Polyethylene Glycol*, Immunol. Methods, 336, 222-228 (2008); Gagnon, P., *Purification Tools for Monoclonal Antibodies*, Validated Biosystems, Tucson, Ariz., 57-87 (1996); Shukla, A. A., and Yigzaw, Y., *Process Scale Bioseparations for the Biopharmaceutical Industry*, Shukla, A., Etzel, M., and Gadam, S., eds., 179-227, CRC Press, Boca Raton (2007); Staby, A., Jacobsen, J. H., Hansen, R. G., Bruus, U. K., Jensen, I. H., *Comparison of Chromatographic Ion-exchange Resins. V. Strong and Weak Cation-Exchange Resins*, J. Chromatogr. A, 1118, 168-179 (2006); Shukla, A. A., Hubbard, B., Tressel, T., Guhan, S., Low, D. J., *Downstream Processing of Monoclonal Antibodies Application of Platform Approaches*, Chromatogr. B, 848, 28-39 (2007); Shihara, T., Kadoya, T. J., *Accelerated Purification Process Development of Monoclonal Antibodies for Shortening Time to Clinic: Design and case Study of Chromatography Processes*, Chromatogr. A, 1176, 149-156 (2007); Fahrner, R. L., Knudsen, H. L., Basey, C. D., Galan, W., Feuerhelm, D., Vanderlaan, M., Blank, G. S., *Industrial Purification of*

*Pharmaceutical Antibodies: Development, Operation, and Validation of Chromatography Processes*, Biotechnol. Genet. Eng. Rev., 18, 301-27 (2001); and Yigzaw, Y., Hinckley, P., Hewig, A. and Vedantham, G., *Ion Exchange Chromatography of Proteins and Clearance of Aggregates*, Curr. Pharm. Biotech., 10, 421-426 (2009)), hydrophobic interaction ("HIC") (see e.g., Chen, J., Tetrault, J., Ley, A., *Comparison of Standard and New Generation Hydrophobic Interaction Chromatography Resins in the Monoclonal Antibody Purification Process*, J. Chromatogr. A., 1177, 272-81 (2008); Gagnon, P., and Grund, E., *Large Scale Process Development for Hydrophobic Interaction Chromatography, Part 4: Controlling Selectivity*, BioPharm, 9, 54-64 (1996); and Lu, Y., Williamson, B., and Gillespie, R., *Recent Advancement in Application of Hydrophobic Interaction Chromatography for Aggregate Removal in Industrial Purification Process*, Curr. Pharm. Biotech., 10, 427-33 (2009)) and hydroxyapatide ("HA") chromatography (see e.g., Aoyama, K., Chiba, J., *Separation of Molecular Forms of Mouse IgG and IgM Monoclonal Antibodies in High Performance Liquid Chromatography on Spherical Hydroxyapatite Beads*, J. Immunol. Methods, 162, 201-210 (1993); Luellau, E., Marison, W., von Stockar, U., *Ceramic Hydroxapatite: A New Tool for Separation and Analysis of IgA Monocolonal Antibodies*, in Animal Cell Technology, Carondo, M., ed., Kluwer Academic Publishers, Netherlands, 265-269 (1997); Luellau, E., von Stockar, U., Vogt, S., Freitag, R., *Development of a Downstream Process for the Isolation and Separation of Monoclonal Immunoglobulin A Monomer, Dimers, and Polymers from Cell Culture Supernatant*, J. Chomatogr. A., 796, 165-175 (1998); Yamakawa, Y., Chiba, J., *High Performance Liquid Chromatography of Mouse Monoclonal Antibodies on Spherical Hydroxyapatite Beads*, J. Liquid. Chromatogr., 11, 665-681 (1998); Coppola, G., Underwood, J., Cartwright, G., Hearn, M. T., *High-performance Liquid Chromatography of Amino Acids, Peptides and Proteins: XCIII. Comparison of Methods for the Purification of Mouse Monoclonal Immunoglobulin M Autoantibodies*, J. Chromatogr. A., 476, 269-290 (1989); Josics, D., Loster, K., Kuhl, R., Noll, F., Reusch, J., *Purification of Monoclonal Antibodies by Hydroxylapatite HPLC and Size Exclusion HPLC*, Biol. Chem. Hoppe-Seylars, 372, 149-156 (1991); Gagnon, P., and Beam, K., *Antibody Aggregate Removal by Hydroxyapatite Chromatography*, Curr. Pharm. Biotech. (2008)).

Prior teachings such as those referenced above have not proven useful for application to the separation of correctly folded etanercept from incorrectly folded etanercept in that they fail to provide qualitatively and/or quantitatively adequate samples. Accordingly, there is a need in the art for an effective and efficient separation technique for use with CHO cell produced etanercept capable of providing etanercept preparations of very high purity (i.e., in which incorrectly folded etanercept is either absent or present in present in very low levels) and in commercially attractive production yields.

The present invention employs so called "mixed mode" chromatography. A chromatography method for purifying recombinantly expressed proteins may generally be termed "mixed mode" when it utilizes at least two different forces to bind proteins and separate a desired protein product from undesired materials that may be present in a relatively impure expression product containing the desired protein along with undesired impurities. These forces can include, for example, electrostatic forces and hydrophobic forces.

Mixed mode chromatography works in a manner similar to more traditional chromatography techniques in that there is a stationary phase and a mobile phase. The stationary phase is normally an insoluble resin or gel, typically referred to as the chromatography resin, which provides the basis for the separation. The resin is contained in a column allowing liquids to pass through and contact the resin. The ability of the chromatography resin to separate desired material from undesired material is made possible by the presence of selected chemical groups, or moieties, that are conjugated to the resin. These conjugated groups, typically called ligands, give the resin the necessary affinity properties (i.e., electrostatic attraction properties resulting from ion exchange moieties present in the ligands, and hydrophobic attraction properties resulting from hydrophobic moieties present in the ligands) thereby enabling the resin to bind to some of the protein materials in an impure sample, but not others, when a solution containing the impure sample is allowed to flow through the chromatography column in contact with the resin.

The stationary phase of the chromatography column containing the resin with these affinity groups is packed inside the chromatography column which is typically a rigid cylindrical vessel into which fluid can be introduced at one end, contact the resin, and then exit the column at an opposite end. A solution containing the protein to be purified can be introduced into (and thus allowed to flow through) the column by placing the protein product into an appropriate solution and allowing the solution, called the mobile phase, to travel through the column. When the protein product to be purified (called the analyte) is presented to the column in the mobile phase, it reaches a state of equilibrium between the column and the mobile phase meaning that some of the material in the protein solution will attach, bind or become affixed to or captured by the affinity groups on the column resin, while the remainder of the material in the product will not attach to the column, but instead will flow through and out of the column where it can be collected for analysis, further processing, or it can be discarded.

Once a protein analyte has become bound to the column in the above-described manner, a washing step—typically called an elution step—is then used to elute, or release, the bound analyte from the column. Depending on the type of affinity ligands (e.g., charge based moieties or hydrophobic moieties, or a combination thereof, etc.,) that are present on the resin to bind analyte to the column, the solution used for eluting or releasing the analyte from the column must have an affinity or an attraction to the analyte and/or the ligand (example charge properties, hydrophobic properties, pH properties, salt concentration, etc.) that can overcome the analyte's affinity, or attraction, to the resin, thereby causing the analyte to be released from the resin (the stationary phase referenced above) and into the elution medium (the mobile phase). Once released or eluted into the mobile phase, the analyte can then flow through and out of the chromatography column for eventual collection, analysis, etc, or transfer to further purification methods or filtration steps. It may be understood that whatever properties of attraction, or affinity, cause an analyte to bind to the chromatography resin (e.g, charge properties or hydrophobic properties), the mobile phase solution that is subsequently used to elute or release the analyte must have a competing set of properties such that the analyte then "prefers" to be in the elution medium rather than remaining captured on the column resin.

Compared to other single mode chromatography techniques, so-called mixed mode chromatography is unique in that the various binding and elution factors can be interdependent and can oppose one another. For example, increasing the ionic strength of the mobile phase in traditional single mode ion-exchange chromatography can drive elution or release of resin-bound analyte when the charged characteristics of an analyte have stronger attraction (preference) for the elution medium versus the attractive forces of the column resin. However, in a mixed mode chromatography method where the chromatography resin uses both electrostatic attraction as well as hydrophobic attraction to bind an analyte, increasing the ionic strength of the mobile (elution) phase can drive release of sample material from the column based on charge properties of that material, while at the same time driving or reinforcing binding of hydrophobic materials in the analyte because such hydrophobic protein materials—in the presence of charged based elution medium—will then tend to have a stronger attraction or preference to bind to the hydrophobic ligands of the column versus the charged environment of the elution medium. Accordingly, while an increase in the salt concentration may indeed drive a tendency to displace charged protein materials from the stationary phase when charged ions in the mobile phase compete with the protein for binding sites on the stationary phase—those portions of an analyte product mixture that may exhibit a higher degree hydrophobic character may have an enhanced tendency to remain bound to the hydrophobic moieties of the mixed mode chromatography column. The ability to exploit these phenomenon in any given protein separation context can hardly be considered predictable.

Two examples of mixed mode resins are Capto™ MMC and Capto™ Adhere (available from GE Healthcare). Capto™ MMC utilizes a ligand attached to a solid support matrix that may interact with the analyte by cation exchange (with its carboxylic group), hydrogen bonding, and hydrophobic interactions. Capto™ MMC's ligand is illustrated below:

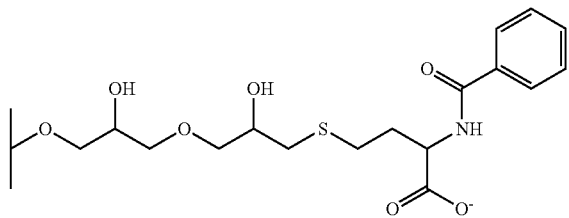 [SMILES: CC(C)OCC(O)COCC(O)CSCCC(NC(=O)c1ccccc1)C(=O)[O-]]

Capto™ Adhere is similar to Capto™ MMC in that it also employs a ligand which is attached to a solid support matrix. The ligand, N-benzyl-N-methyl ethanol amine, also interacts with the analyte by anion exchange, hydrogen bonding, and hydrophobic interactions. Capto™ Adhere's ligand is illustrated below:

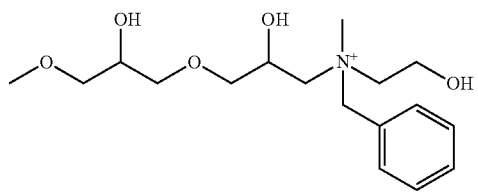 [SMILES: COCC(O)COCC(O)C[N+](C)(CCO)Cc1ccccc1]

In both ligands, hydrophobic interaction is expected to be weak. Thus, if these ligands have only hydrophobic moieties (no charges), they would most likely require salting-out (protein precipitating) conditions for protein binding. However, having electrostatic interaction can make such weak hydrophobic interaction sufficient to provide additional binding force.

SUMMARY OF THE INVENTION

The present invention is premised upon the discovery that mixed mode chromatography, for example using Capto™ MMC and Capto™ Adhere as the mixed mode chromatography resin, may be employed to purify an analyte comprising a mixture of correctly folded and incorrectly folded protein, including, for example, a protein mixture comprising correctly folded and incorrectly folded etanercept, whereby the correctly folded protein can be efficiently separated from the incorrectly or misfolded protein in a highly efficient manner, and in excellent production yields, to obtain a protein preparation that is very highly enriched in the desired, correctly folded protein. Moreover, the invention encompasses the ability to practice the mixed mode chromatographic separation described herein in such a manner as to obtain an elution product from the chromatographic separation that can, if desired, be free or essentially free of incorrectly folded product, although it may be understood for purposes of balancing yield and purity, one may find it acceptable to include very low levels of incorrectly folded product (e.g., less than 5 wt % and preferably less than 3 wt %) in order to maximize yields to a desired extent.

Accordingly, in a first embodiment the present invention is a mixed mode chromatography method for separating a correctly folded protein from an incorrectly folded protein, comprising the steps of: (a) binding a first protein mixture comprising both correctly folded and incorrectly folded conformations of a given protein to a mixed mode chromatography resin having both ion exchange moieties and hydrophobic moieties; (b) eluting the correctly folded protein from the mixed mode resin to obtain a second protein mixture comprising a higher proportion of correctly folded protein than the first protein mixture. The term "higher proportion" means that the ratio of correctly to incorrectly folded protein in the eluate of step (b) is at least greater than 1:1, but most preferably greater than about 8:2 and preferably greater than about 9:1. The second protein mixture most preferably contains correctly folded protein in an amount constituting at least about 95 wt % of the second protein mixture.

In a second embodiment, the method is directed to a mixed mode chromatography method for purifying a protein mixture in order to separate correctly folded etanercept from incorrectly folded etanercept present in said mixture, the method comprising the steps of: (a) contacting a mixed mode chromatography resin having hydrophobic moieties and ion exchange moieties with a solution containing a protein mixture comprising correctly folded etanercept and incorrectly folded etanercept, such that both the correctly and incorrectly folded etanercept become affixed to, bound to or captured upon the mixed mode chromatography resin; and (b) contacting the mixed mode resin with a solution capable of eluting the etanercept proteins from the mixed mode chromatography resin to obtain an eluate in which the ratio of the amount of correctly folded etanercept to incorrectly folded etanercept is greater, and preferably much greater than that of the protein mixture introduced to the resin in step (a).

A third embodiment the present invention is directed to an etanercept-containing protein mixture, or a pharmaceutically acceptable formulation comprising said mixture, obtained in accordance with the above-described method embodiments and wherein said protein mixture comprises correctly folded etanercept in amount constituting greater than about 90 wt. % of the protein mixture; and comprising incorrectly folded etanercept in an amount constituting less than about 5 wt % of the protein mixture; and wherein the protein mixture has a combined amount of correctly folded and incorrectly folded etanercept constituting at least about 95 and preferably at least about 98 wt. % of the etanercept-containing protein mixture. Amounts of correctly folded and incorrectly folded etanercept can be determined using hydrophobic interaction chromatography (single mode). The combined amounts of correctly folded and incorrectly folded etanercept can be determined using size exclusion chromatography ("SEC"). As used herein, the terms "etanercept-based protein mixture" or "etanercept-containing protein mixture" or "etanercept preparation" or "etanercept-based material" and the like, should be read as synonymous and are meant to denote a protein mixture in which the major component comprises correctly folded etanercept and the minor components may comprise clipped etanercept, incorrectly folded etanercept, aggregated etanercept (such aggregates being comprised of correctly and/or incorrectly folded etanercept), or fragments of etanercept. The present invention affords the ability to produce an etanercept-based protein mixture (or etanercept preparation) for use as the active ingredient in pharmaceutical formulations in which it is desired to maximize the amount of correctly folded etanercept, while minimizing the amount of incorrectly folded (including aggregated) etanercept, to a greater extent than has been heretofore achieved.

In a fourth embodiment, the invention is directed to a pharmaceutically acceptable formulation comprising highly pure etanercept suitable for administration to a subject requiring treatment for a TNF mediated condition, said formulation containing a protein mixture comprising a major amount of correctly folded etanercept and a minor amount of incorrectly folded etanercept, wherein: (i) the incorrectly folded etanercept constitutes less than about 10 wt. %, preferably less than about 8 wt. % and most preferably preferably less than about 5 wt. % of the protein mixture; (ii) the correctly folded etanercept constitutes more than 90 wt. % and preferably more than about 92 wt % and most preferably more than about 95 wt % of the protein mixture; and (iii) the total amount of correctly folded etanercept and incorrectly folded etanercept (but not including aggregates thereof) constitutes at least 95 wt % and preferably at least 98% by weight of the protein mixture; wherein the formulation further comprises pharmaceutically acceptable inactive ingredients, excipients or carriers rendering the formulation suitable for administration to the subject.

In a fifth embodiment the invention is a method for producing an etanercept-containing protein mixture having high purity with respect to the amount of correctly folded versus incorrectly folded etanercept present therein, said method comprising the steps of: (1) expressing etanercept in a mammalian expression system to obtain a harvest cell culture fluid containing an etanercept-containing protein mixture comprising both correctly folded and incorrectly folded etanercept; (2) subjecting the harvest cell culture fluid obtained in step 1 to a purification process whereby an etanercept-containing protein mixture is obtained with a reduced amount of, or substantially free of, undesired impurities (i.e., non-etanercept-based proteins) present in the harvest cell culture fluid produced in step (1); (3) contacting the etanercept-containing protein mixture obtained in step (2) one or more times with a mixed mode chromatographic resin having both ion exchange moieties and hydrophobic interaction moieties in order to affix proteins contained in the mixture to the resin; and (4) contacting the mixed mode resin having protein bound thereon from step 3 with a solution capable of eluting correctly folded etanercept from the mixed mode resin to obtain an eluate comprising an etanercept-containing protein mixture having a higher proportion of correctly folded etanercept versus incorrectly folded etanercept than the etanercept-containing mixture introduced to the resin in step 3; and wherein (i) the amount of protein present in the etanercept-containing protein mixture obtained from purification of step 2 is at least about 80 wt % and most preferably at least about 85 wt % of the amount of the etanercept-based protein mixture present in the harvest cell culture fluid obtained in step 1; (ii) the combined amount of correctly and incorrectly folded etanercept protein present in the protein mixture eluted in step 4 is at least about 60 wt. % of the amount thereof present in the protein mixture obtained from step 2; (iii) the amount of correctly folded etanercept present in the eluate of step 4 is at least about 30 wt. % and preferably at least about 34 wt. % of the amount of etanercept-containing protein mixture present in the harvest cell culture fluid obtained in step 1; and (iv) said correctly folded etanercept constitutes at least about 90 wt % and preferably at least about 95 wt. % of the eluate obtained in step 4.

In a sixth embodiment, the invention is directed to a method for treating a subject suffering from a TNF mediated disease, comprising the steps of administering to such individual a pharmaceutical formulation containing a protein mixture comprising correctly folded etanercept and incorrectly folded etanercept, said mixture being obtained by any of the methods described above, and wherein the amount of incorrectly folded etanercept in the protein mixture is less than about 10 wt. % and preferably less than about 5 wt % of said mixture.

In a seventh embodiment the invention is directed to a method for treating a subject suffering from a TNF mediated disease, comprising the steps of administering to such individual a pharmaceutical formulation containing a protein mixture comprising correctly folded etanercept and incorrectly folded etanercept wherein the amount of incorrectly folded etanercept in the protein mixture is less than about 10 wt % and preferably less than about 5 wt % of said mixture.

In an eighth embodiment the invention is directed to a method for separating correctly folded etanercept from incorrectly folded etanercept, wherein chromatographic means are used to achieve said separation, and wherein the chromatographic means consist solely of mixed mode chromatography in which a mixture comprising correctly folded and incorrectly folded etanercept is contacted with a mixed mode chromatographic resin having ion exchange and hydrophobic moieties, and then eluted therefrom, to obtain an eluate comprising at least about 85 and preferably at least about 90, and most preferably at least about 95 wt % correctly folded etanercept. With respect to this embodiment, when stated herein that "chromatography means consist solely of mixed chromatography," it should be understood that such phraseology does not exclude the optional use of various chromatography means (e.g., HIC, SEC, etc) when used solely for analytical purposes. This embodiment is advantageous in that it does not require use of separation methodologies for resolving correctly from incorrectly folded protein other than the mixed mode methodology described herein.

In a further aspect, the methods described above as applied to etanercept may be practiced two or more times to obtain a highly pure etanercept prepration in the following manner: by performing a first mixed mode separation (separation #1) by carrying out steps (a) and (b) as described, e.g., in embodiments 1 and 2 above; followed by performing a second mixed mode separation (separation #2) by carrying out steps (a) and (b) again; where the eluate obtained in step (b) of separation #1 is then used as the analyte (i.e., the solution containing a protein mixture) for step (a) of separation #2. The mixed mode resins used in separation #1 and separation #2 can be the same or different. In a particularly preferred practice of this aspect, separation #1 is performed with CAPTO MMC mixed mode resin and separation #2 is performed with CAPTO ADHERE mixed mode resin.

Optionally, the etanercept preparations resulting from the method of the invention, or provided in the preparation, formulation or treatment embodiments described above may, if so desired, be free or essentially free of incorrectly folded etanercept, although it may be understood that the ability herein to provide etanercept preparations having remarkably low levels of incorrectly folded etanercept, preferably less than about 10 wt. % and most preferably less than about 5 wt % of the total amount of an etanercept-based protein mixture present in a drug formulation, represents a significant advance over pharmaceutical formulations currently available for commercial sale containing etanercept-based mixtures in which the amount of incorrectly folded etanercept in such mixtures, based on HIC analysis, can be greater than about 10% of the etanercept-based proteins found in such formulations.

Preferred mixed mode resins for use in the invention are CAPTO MMC and CAPTO ADHERE; however, it should be understood that any mixed mode resin functionalized with both ion exchange moieties and hydrophobic moieties are contemplated for use in the present invention.

Without being bound to any particular theory, it was considered possible, if not at all predictable, that one might be able to exploit the interdependence and opposing action between the charge characteristics and the hydrophobic characteristics in a mixed mode chromatography employing these two affinity types, in order to develop a highly efficient separation of properly folded protein species from species that are incorrectly folded and/or aggregated. Surprisingly, the mixed mode method of the invention does not need to be combined with or supplemented with any other separation strategies to resolve correctly form incorrectly folded protein in excellent yield and high purity. For example, it is not necessary to employ an additional HIC step to further achieve such separation of correctly from incorrectly folded protein.

As applied to etanercept, the mixed mode chromatography method according to the present invention involves the occurrence of the following general sequence of phenomena: First, upon introduction of an impure etanercept-containing sample to the mixed mode resin (i.e., a sample comprising correctly folded, incorrectly folded and other impurities) such as that obtained, e.g., from CHO expression of etanercept, the method of the invention allows etanercept (both correctly and incorrectly folded) to bind to the mixed mode resin. Secondly, during a subsequent elution or washing step (e.g, using a salt gradient applied preferably in a gradient of increasing concentration), the present invention allows for release (i.e. elution) from the resin of an etanercept-based mixture wherein the etanercept contained therein is predominantly folded correctly, while substantially allowing etanercept that is incorrectly folded to remain bound or captured on the mixed mode resin; whereby there may be obtained in the material eluted from the resin a very high proportion of properly folded etanercept (as compared to a lower proportion thereof present in the etanercept-containing protein sample initially introduced to and bound to the resin). In terms of physical operation of the mixed mode chromatography of the present invention, the mixed mode resin can be contained (i.e., packed) into a rigid columnar containment means or vessel which can contain the resin, and which has inlet and outlet means for allowing fluid solutions to enter at one end of the column, flow into contact with the resin, and then exit at an opposite end of the vessel to be collected for further analysis or processing, or to be discarded.

The solution containing a protein mixture of correctly folded and incorrectly folded etanercept used in step (a) of the methods described above can be obtained in a known manner from the expression of etanercept protein in mammalian cell culture, for example CHO cells. Prior to mixed mode chromatographic purification in the present invention, the harvested protein from the mammalian expression (a harvest cell culture fluid) may be subjected to an initial purification step, such as Protein A affinity purification, to remove impurities. While such step may be desirable for removing non-etanercept based impurities, this purification will generally not result in appreciable separation (i.e., resolution) of correctly folded etanercept from incorrectly folded etanercept. Accordingly the Protein A pool is then subject to the mixed mode methodology of the present invention to accomplish such separation.

The method of the present invention affords commercially useful recoveries (yields) of correctly folded etanercept. For example, in instances in which the etanercept based protein solution of correctly and incorrectly folded etanercept used in step (a) of the present method is preferably provided in the form of Protein A chromatography output obtained by purifying a mammalian expression product of etanercept in a Protein A column, the amount of material recovered in the Protein A purification step is preferably at least about 80 wt. % and preferably at least about 85 wt % of the etanercept-based expression products present in the harvest cell culture introduced to the Protein A column (where the amount of etanercept-based proteins present in the harvest cell culture can be determined by Fc Elisa, and the amount of etanercept based proteins obtained in the Protein A elution pool can be determined by UV absorbance at A280 nm). Subsequently, when the mixed mode chromatography of the present invention is practiced using the above-referenced Protein A-purified material, the amount of etanercept-based protein material obtained in the elution of step (b) of the present is preferably at least about 60 wt. % and preferably at least about 70 wt % of the amount of etanercept-based material introduced to the mixed mode resin in step (a) of the invention.

Accordingly the overall yield of a highly pure etanercept mixture in the mixed mode eluate of step (b) hereof that is highly enriched in correctly folded etanercept (i.e., containing not more than 10 wt % and preferably not more than about 5 wt % misfolded material by weight of the eluate) can be anywhere from about 30 to about 50 wt % of the etanercept-based mixture originally present in a harvest cell culture fluid prior to purification (e.g., Protein A purification) thereof.

Purification of the harvest cell culture fluid may also be achieved by other chromatographic means, such as mixed mode chromatography using chromatography resins having both ion exchange and hydrophobic interaction moieites.

In practicing the method of the present invention, additional filtration steps (e..g viral filtration, and tangential flow filtration) may be conducted in a known manner to further process eluates produced in step (b) of the above-described mixed mode chromatography method.

The present invention affords a vastly improved separation method for separation of correctly folded from incorrectly folded conformations (including aggregates) of a given protein, and, in particular, resolution of properly folded etanercept from misfolded (and aggregated) etanercept obtained from a mammalian cell culture harvest comprising a highly heterogenous mixture of etanercept-based species.

BRIEF DESCRIPTION OF THE DRAWINGS

FIG. 1 shows the chemical structure of Capto-MMC and Capto-Adhere mixed mode resin.

FIG. 4C (Elution profile of Protein A pool from Capto MMC) shows SDS-PATE and native-PAGE of eluted sample for different Protein A pool wherein: Lane-0, standard; lane-1, Load, lane-2, FT; lane-3 to lane-8, eluted fractions; lane-9, 1 M arginine.

FIG. 6 shows a HIC analysis of Capto-MMC eluted fractions.

FIG. 10A (Elution profile of Protein-A pool from Capto-Adhere) shows a Chromatogram of elution by pH and arginine gradient.

DETAILED DESCRIPTION OF THE INVENTION

Figure 2A:
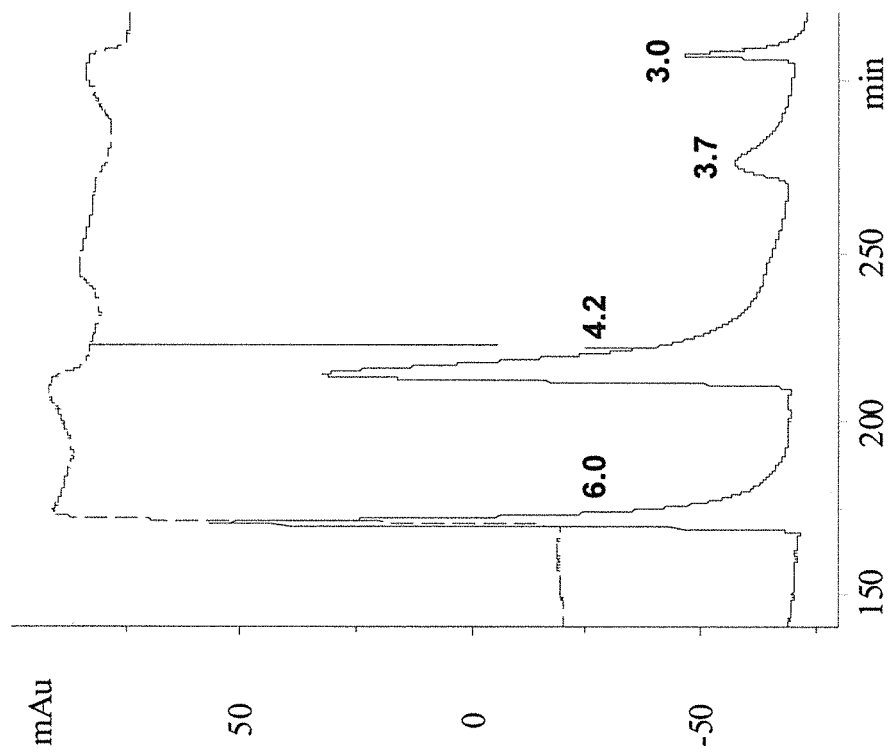
FIG. 2A (elution profile from Protein A) shows an elution profile from Protein-A of CHO harvest culture comprising both correctly folded and misfolded etanercept protein using elution by 0.1 M citrate at indicated pH containing 1 M arginine. The solid curve is UV abso absorbance; the dotted curve, is conductivity (same in the following figures).

The invention is premised on the discovery herein that mixed mode resins using both ion exchange and hydrophobic attraction principles, for example Capto™ MMC and Capto™ Adhere, can be used to bind and then preferentially (i.e. selectively) elute correctly folded versus incorrectly folded conformations of a given protein analyte. Both of the aforementioned mixed mode resins comprise ligands with moieties (i.e., chemical groups) that provide two different modes for attracting and binding protein analyte, namely ion exchange attraction and hydrophobic interaction.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. The invention is not limited to the various embodiments given in this specification.

Unless otherwise defined, all technical and scientific terms used herein have the same meaning as commonly understood by one of ordinary skill in the art to which this invention pertains. In the case of conflict, the present document, including definitions will control.

"Around," "about" or "approximately" shall generally mean within 20 percent, within 10 percent, within 5, 4, 3, 2 or 1 percent of a given value or range. Numerical quantities given are approximate, meaning that the term "around," "about" or "approximately" can be inferred if not expressly stated.

The term "etanercept" as used herein means the active ingredient contained in the commercial formulation of Enbrel®, namely a homodimer of the fusion polypeptide consisting of the extracellular ligand-binding portion of the human 75 kilodalton (p'75) tumor necrosis factor receptor ("TNFR") linked to the Fc portion [fragment, crystallizable] of human Immunoglobulin G ("IgG1"). Etanercept is a homodimer in that two chains of the 75 kilodalton TNFR:Fc molecule as descibred above are connected by a disulfide linkage at a hinge region of the Fc portion. Etanercept consists of 934 amino acids and has an apparent molecular weight of approximately 150 kilodaltons, and the Fc component thereof contains the constant heavy 2 (CH2) domain, the constant heavy 3 (CH3) domain and hinge region, but not the constant heavy 1 (CH1) domain of human IgG1. For the purposes of the present application, the term "etanercept" may also encompass etanercept with minor modifications in the amino acid structure (including deletions, additions, and/or substitutions of amino acids) which do not significantly affect the function of the polypeptide as described above. The term etanercept should also be understood to include proteins intended or considered to be so-called biosimilar or bio-better variants of etanercept.

The term "correctly folded etanercept" as used herein is intended to denote a folding conformation of the etanercept homodimer (as defined above) having biological activity for inhibition of TNF and conformation that are the same or substantially the same as the conformation and biological activity of the active ingredient in Enbrel®.

The term "incorrectly folded etanercept" as used herein is intended to encompass: (i) a homodimeric protein having the same or essentially the same amino acid sequence as etanercept (as defined above), but having a conformation different from that of correctly folded etanercept, wherein said different conformation renders the protein lacking or substantially lacking in biological activity as a TNF inhibitor; and/or (ii) an aggregate in which two or more correctly and/or incorrectly folded etanercept homodimers have become associated (i.e., aggregated or clumped) in such a manner as to form species having higher molecular weight than correctly folded etanercept; and/or (iii) a mixture of (i) and (ii); and/or (iv) aggregated i.e., clumped protein compositions comprising the same or essentially the same sequence, or portions thereof, as correctly folded etanercept but which exhibit decreased elution position (due to greater hydrophobicity) on an HIC column as compared to correctly folded etanercept.

The term "treatment" refers to any administration or application of remedies for disease in a mammal and includes inhibiting the disease, arresting its development, relieving the disease (for example, by causing regression, or restoring or repairing a lost, missing, or defective function) or stimulating an inefficient process. The term includes obtaining a desired pharmacologic and/or physiologic effect and covering any treatment of a pathological condition or disorder in a mammal. The effect may be prophylactic in terms of completely or partially preventing a disorder or symptom thereof and/or may be therapeutic in terms of a partial or complete cure for a disorder and/or adverse affect attributable to the disorder. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating or ameliorating the disorder, or symptoms associated therewith, where ameliorating is used in a broad sense to refer to at least a reduction in the magnitude of a parameter, such as inflammation, pain and/or tumor size.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The term "composition" or "formulation" refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses or powders.

The present invention is suitable for separating correctly folded from incorrectly folded conformations of a given protein. Examples of proteins that can be processed in accordance with the methods of the invention include any disulfide-containing proteins that require refolding such as G-CSF, IGF, insulin, growth hormone, etc. as well as engineered antibodies, e.g., single chain variable domain antibody fragments.

Etanercept suitable for purification according to the mixed mode chromatographic method of the present invention can be produced by living host cells that express etanercept, such as hybridomas in the case of antibodies, or host cells that that have been genetically engineered to produce the polypeptide in the case of fusion polypeptides or antibodies. Methods of genetically engineering cells to produce polypeptides are well known in the art. See, e.g., Ausubel et al., eds. (1990), Current Protocols in Molecular Biology (Wiley, New York). Such methods include introducing nucleic acids that encode and allow expression of the polypeptide into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5.alpha, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and W138. New animal cell lines can be established using methods well know by those skilled in the art (e.g., by transformation, viral infection, and/or selection). Optionally, etanercept can be secreted by the host cells into the medium.

Prior to mixed mode chromatographic separation of correctly folded from misfolded etanercept, purification of the expressed etanercept can be performed by any standard method. When etanercept is produced intracellularly, the particulate debris is removed, for example, by centrifugation or ultrafiltration. When etanercept is secreted into the medium, supernatants from such expression systems can be first concentrated using standard polypeptide concentration filters. Protease inhibitors can also be added to inhibit proteolysis and antibiotics can be included to prevent the growth of microorganisms.

Etanercept can be purified using, for example, hydroxyapatite chromatography, gel electrophoresis, dialysis, and affinity chromatography, and any combination of known or yet to be discovered purification techniques, including but not limited to Protein A chromatography, fractionation on an ion-exchange column, ethanol precipitation, reverse phase HPLC, chromatography on silica, chromatography on heparin SEPHAROSET®, an anion or cation exchange resin chromatography (such as a polyaspartic acid column), chromatofocusing, SDS-PAGE, and ammonium sulfate precipitation.

In very general terms, as applied to etanercept (but not limited thereto), the invention provides a protein separation method comprising the steps of (a) introducing a solution containing an etanercept-based protein mixture having both correctly folded and incorrectly folded etanercept to a mixed mode chromatography resin functionalized with ion exchange moieties as well as hydrophobic interaction moieties under conditions capable of allowing the correctly and incorrectly folded etanercept to bind to the resin; and then (b) washing the resin with elution media capable of eluting correctly folded etanercept from the resin such that the resulting eluate has a higher proportion of correctly folded etanercept than the protein solution introduced in step (a).

Optionally, the method may further include the preliminary steps of expressing etanercept in a mammalian cell culture such as a CHO cell culture, and then purifying the expression product using for example Protein A chromatography whereupon the protein A product output becomes the protein solution used in step (a) of the present invention. It should be understood that the method of the invention may be practiced in such a manner that mammalian expression and protein A steps, giving rise to a starting solution for use in step (a) of the present invention, may be performed by a first entity at a given manufacturing site, while the method of mixed mode separation of the present invention might be performed by the same or a different entity at the same or a different manufacturing site.

Conditions for Step (a)—Binding to CAPTO MMC Mixed Mode Resin. In step (a) of the invention, the protein solution comprising correctly folded and incorrectly folded etanercept should be introduced to the CAPTO MMC mixed mode resin for binding thereto at a pH of from about 4 to about 8, and preferably at a pH of about 4 to about 6. Alternatively, when CAPTO ADHERE mixed mode resin is used the protein solution in step (a) comprising correctly folded and incorrectly folded etanercept should be introduced to the CAPTO ADHERE mixed mode resin for binding thereto at a pH of from about 6 to about 8.5, and preferably at a pH of about 7 to about 8.

Conditions for step (b)—Elution from the Mixed Mode Resin. In step (b) the elution medium comprises a salt at a predetermined concentration, and applied to the column in a predetermined manner effective for preferential elution of correctly folded etanercept protein versus incorrectly folded etanercept. While, generally speaking, the eluate should contain a higher ratio of correctly folded to incorrectly folded etanercept, the salt solution and the manner of application thereof to the resin, is preferably selected such that the amount of correctly folded etanercept greatly exceeds the amount of incorrectly folded etanercept in the eluate of step (b). Early eluted fractions can contain essentially 100% correctly folded protein. The salt solution elution step can be accomplished by changing (increasing) the molar concentration of the salt solution, such as through a gradient. The gradient can be accomplished step wise, but is preferred to be continuous and linear. In a preferred embodiment, the salt solution contains sodium chloride ("NaCl"). The NaCl linear gradient can be from about 0 to about 1 M.

In an alternative embodiment, the salt solution can contain sodium sulfate ("$Na_2SO_4$"). The $Na_2SO_4$ solution may also be applied in a step wise or linear gradient, preferably linearly and most preferably from a concentration gradient of from about 0 to about 1 molar.

The etanercept can be obtained by culturing in CHO cells.

In a preferred embodiment, the salt solution comprises NaCl.

The following procedures were followed for expression, purification of expression products, and analysis of etanercept-containing eluates obtained from the mixed mode chromatography method of the present invention:

Expression of Etanercept. Etanercept is expressed in conditioned media ("CM") of recombinant CHO cells transfected with a gene coding for the human TNFR extracellular domain fused to human Fc at the C-terminus. Examples in the art for mammalian expression of etanercept may be found in the following U.S. patents, incorporated herein by reference: RE 36755; U.S. Pat. No. 5,605,690; EP 464,533; EP 417,563; U.S. Pat. Nos. 8,063,182; and 7,294,481.

Protein A Chromatography. The CM obtained above is processed using a Protein A column with 1 ml HiTrap rProtein A column (available from GE Healthcare) and equilibrated with a 10 mM phosphate, 0.1 M NaCl, pH 7.0 solution. After washing the column with a 1 M arginine-hydrochloride ("arginine"), 0.1 M citrate, pH 6.0 solution, the bound proteins are eluted stepwise with pH 4.2, 3.7 and 3.0 containing 1 M arginine and 0.1 M citrate. Alternatively, the column may be processed without arginine in descending pH with 0.1 M citrate. In the absence of arginine, a majority of the etanercept was eluted at a pH of 3.85 to provide an eluate that comprises contaminants as well as incorrectly folded etanercept, fragments of etanercept, aggregates of etanercept, etc., eluting below this pH. The Protein A eluate is then subjected to Capto™ MMC or Capto™ Adhere in a HiTrap column (available from GE Healthcare) as described below in the examples.

Figure 2B:
FIG. 2B (elution profiled from Protein A) shows the Native-PAGE results for samples eluted from Protein-A wherein Lane-1 is standard (commercial ENBREL®); lane-2 is Load; lane-3 is FT (flow-through); lane-4, pH 6.0; lane-5, pH 4.2; lane-6, pH 3.7; lane-7, pH 3.0.

Analysis of Protein A eluate. Analysis of the Protein A eluate obtained above is set forth in FIGS. 2A and 2B. FIG. 2A shows the elution profile from Protein-A with low pH buffers containing 1 M arginine. A large UV absorbance peak was observed at pH 6.0 (peak marked as 6.0) and contained no band (FIG. 2B, lane-4) corresponding to the commercial Etanercept as examined by native-PAGE (lane-1): note that no Etanercept flowed through the Protein-A column (compare lane-2 and 3). Although no protein bands were observed at pH 6.0 (lane-4), the observed large UV absorbance indicates elution of pigments. After reaching baseline absorbance (FIG. 2A), the column was then eluted with 0.1 M arginine, 0.1 M citrate, pH 4.2, resulting in a sharp elution peak (FIG. 2A, marked 4.2). Native-PAGE analysis of this peak showed an intense band of Etanercept, along with smearing low mobility bands (lane-5). HIC analysis of the eluted protein showed 2 peaks, the first peak corresponding to the main peak of commercial Etanercept and second peak corresponding to the minor species also present in the commercial Etanercept. Although the nature of the second peak is not clear, it appears to be misfolded species of Etanercept, as it bound to Protein-A and hence should contain the Fc domain. The remaining bound proteins were eluted with pH 3.7 and then 3.0, both containing 1 M arginine. These low pH solvents resulted in elution of small peaks as shown in FIG. 2A (3.7 and 3.0). The pH 3.7 peak contained a small amount of etanercept (lane-6), while the pH 3.0 peak contained mainly low mobility species, corresponding to the misfolded species as well as species that may also be aggregating (lane-7). A similar elution pattern was observed in the absence of arginine. A lower pH, e.g., pH 3.85, was required to elute etanercept and further decrease in pH resulted in elution of low mobility species. The fact that these low mobility species bound to Protein-A means that they were also Fc-fusion proteins. Since these species eluted at lower pH than Etanercept, they bound to Protein-A more tightly. These analyses confirm that expression of etanercept in recombinant CHO cells leads to both native (correctly folded) etanercept, corresponding to the correctly folded species, and low mobility species, corresponding to the incorrectly misfolded species, as analyzed by analytical HIC. Since the misfolded species eluted later in HIC, it should be more hydrophobic than the native etanercept. Depending on the CHO clones and fermentation conditions, the amount of correctly folded species varied from 40 to 60 wt 5 of the protein A eluate. In the examples below the capacity of mixed mode chromatography to separate folded species from misfolded species is evaluated.

Analytical Methods.

The eluted fractions from Protein A, Capto™ MMC and Capto™ Adhere compositions can be analyzed using a variety of techniques well known in the art such as size exclusion chromatography (SEC), denatured SEC (dSEC), hydrophobic interaction chromatography (HIC), sodium dodecylsulfate polyacrylamide gel electrophoresis (SDS-PAGE) and native-PAGE. For example, the techniques of Size Exclusion Chromatography are described in Hawe et al, Pharm. Res. 2011, 28: 2302 and/or van Marrschalkerweerd et al., Eur. J. Pharm. Biopharm. 2011, 78: 213.

SDS-PAGE. For example, the eluted fractions from Protein A, Capto™ MMC and Capto™ Adhere can be analyzed by sodium dodecylsulfate or native polyacrylamide gel electrophoresis (SDS-PAGE or native-PAGE, respectively). Both SDS-PAGE and native-PAGE were carried out using 6% Tris-Glycine gel (available from Life Technology). SDS-PAGE may be done under non-reducing conditions so that disulfide-linked aggregates can be observed.

Size Exclusion Chromatography. Eluate fractions obtained using the mixed mode chromatography methods of the present invention may be analyzed using the well known technique of Size Exclusion Chromatography (SEC), a high-performance liquid chromatography ("HPLC") method in which analytes are separated by size (see Rogner, M. (2000). Size Exclusion Chromatography. *Protein Liquid Chromatography*. M. Kastner. Amsterdam, Elsevier. 61: 89-145.). For example, and not by way of limitation, a mobile phase buffer can be prepared to contain 50 mM sodium phosphate monobasic monohydrate and 150 mM arginine. The pH is adjusted to 6.5 using 1 M HCl. Separations can be performed using a Tosoh TSK-Gel SWx1 6 mm×4 cm guard column (cat. no. 8543) attached linearly to a Tosoh TSK-Gel G4000 SWx1 7.8 mm×30 cm (cat. no. 8542). To perform a separation, the columns are brought to room temperature (23° C.) and equilibrated with mobile phase at a flow rate of 0.5 mL/min. 5 microliters of 50 mg/mL of solution comprising etanercept is injected onto the column using an autosampler. The separation can be accomplished over about 30 minutes at a flow rate of about 0.5 mL/minute. Column eluent was monitored at a wavelength of 280 nm during this time. Integration can be performed using Chromeleon software (Dionex). Prior to integration, the SEC chromatogram for a buffer containing no etanercept is subtracted from all chromatograms. All integration can be performed between retention times of 12 minutes and 26 minutes. Several parameters are used to define a peak. The minimum area for a detected peak is set to 0.05 mAu*min. The two-dimensional sensitivity for peak detection is set to 0.01 mAu and 75 seconds. Peak shoulders are added manually using a manual integration tool. All detected peaks are manually adjusted in two steps. First, peak baselines (the bottom boundary of the peak) is adjusted to horizontal. Secondly, the vertical positions of the peak baselines are adjusted to that of the chromatogram baseline. The chromatogram baseline value is defined as the signal in absence of analyte. The signal in absence of analyte is defined as the absorbance in mAu at 12 minutes retention time.

Hydrophobic Interaction Chromatograpy (HIC). Hydrophobic interaction chromatography (HIC) analysis may be carried out on Butyl-Sepharose® using an ammonium sulfate gradient from 1.8 to 0 M. HIC chromatography may also be carried in the manner described in U.S. Pat. No. 7,294,481 (see column 19, lines 49-55). Reference is also made to U.S. Pat. No. 7,157,557; Chen J, Tetrault J, Ley A. (2008) J Chromatogr A. 1177, 272-81; Gagnon P. and Grund E.(1996) BioPharm, 9, 54-64; and Lu, Y., Williamson, B., and Gillespie, R. Recent advancement in application of hydrophobic interaction chromatography for aggregate removal in industrial purification process. Curr. Pharm. Biotech.

Figure 4A:
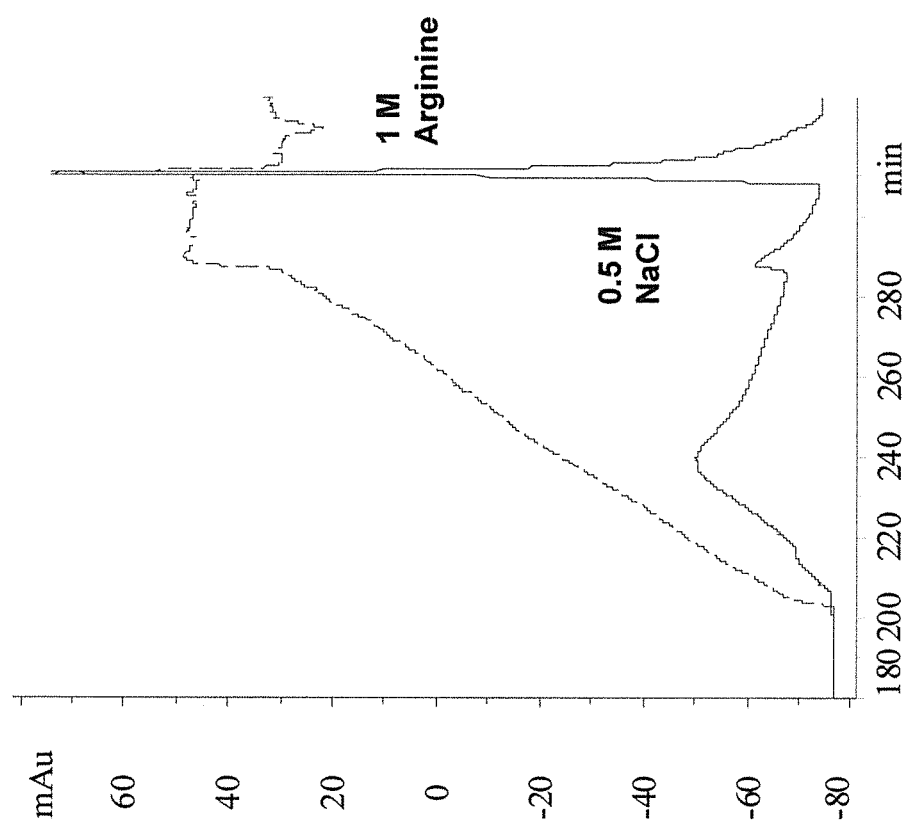
FIG. 4A (Elution profile of Protein A pool from Capto MMC) shows a chromatograph of elution by 0-0.5 M NaCl gradient at pH 7.5. The column was equilibrated with 10 mM phosphate, pH 7.5 before gradient elution.

With regard to HIC analysis of etanercept preparations produced according to the mixed mode chromatography method of the present invention, it is noted that FIG. 4 in U.S. Pat. No. 7,294,481, incorporated herein by reference, contains an HIC chromatogram of an etanercept preparation in which there are three peaks, the largest of which (identified as "peak 2" in the '481 patent) is disclosed as representing properly folded etanercept fusion protein; while a smaller peak (identified as "peak 3" in the 481 patent) is postulated by the patentee to contain "scrambled" (i.e., believed in the present discussion to be synonymous with incorrectly folded) etanercept as well as aggregated etanercept (see U.S. Pat. No. 7,294,481 column 22, lines 13-66, and FIG. 5 thereof). A significant advantage of the present invention is the ability to provide an extraordinarily high purity etanercept containing preparation, in commercially attractive yields, in which "peak 3" of the HIC chromatogram, as referenced in FIG. 4 and FIG. 5 of the '481 patent, and believed herein to comprise incorrectly folded etanercept, can be substantially reduced or essentially eliminated.

The invention is further directed to pharmaceutical formulations of etanercept wherein a high purity etanercept for use in such formulations is obtained using the methods of the present invention. The formulations of the invention may also include buffers, tonicity modifiers, excipients, pharmaceutically acceptable carriers and other commonly used inactive ingredients of the pharmaceutical compositions. For simplicity, these are discussed more fully later in the application.

Buffers maintain pH in a desired range. Suitable buffers include histidine, potassium phosphate, sodium or potassium citrate, maleic acid, ammonium acetate, tris-(hydroxymethyl)-aminomethane (tris), various forms of acetate and diethanolamine. The concentration of the buffer in the formulation is preferably between about 1 mM to about 1 M, and more preferably about 10 mM to about 200 mM. Buffers are well known in the art and are manufactured by known methods and available from commercial suppliers.

Examples of suitable buffers are phosphate, histidine, citrate, maleate, tartrate, succinate, acetate, tris-(hydroxymethyl)-aminomethane (tris), bicarbonate.

In a preferred embodiment, the buffer is sodium phosphate.

In a preferred embodiment, the pH of the pharmaceutical composition is at or near physiological levels. Thus, preferably, the pH of the provided compositions is between about 5.8 and about 8.4; and even more preferably, between about 6.2 and about 7.4. A person of ordinary skill in the art will understand that the pH can be adjusted as necessary to maximize stability and solubility of etanercept in a particular formulation. Thus, etanercept formulations at a pH outside of physiological ranges, yet tolerable to the patient, are also within the scope of the invention.

A tonicity modifier is a molecule that contributes to the osmolality of a solution. The osmolality of a pharmaceutical composition is preferably adjusted to maximize the active ingredient's stability and/or to minimize discomfort to the patient upon administration. It is generally preferred that a pharmaceutical composition be isotonic with serum, i.e., having the same or similar osmolality, which is achieved by addition of a tonicity modifier.

In a preferred embodiment, the osmolality of the provided formulations is from about 180 to about 420 mOsM. However, it is to be understood that the osmolality can be either higher or lower as specific conditions require.

Examples of tonicity modifiers suitable for modifying osmolality include, but are not limited to amino acids (not including arginine) (e.g., cysteine, histidine and glycine), salts (e.g., sodium chloride, potassium chloride and sodium citrate) and/or saccharides/polyols (e.g., sucrose, glucose and mannitol).

Preferred tonicity modifiers are glycine, alanine, sodium chloride, potassium chloride, and sodium sulfate.

In a preferred embodiment, the concentration of the tonicity modifier in the formulation is preferably between about 1 mM to about 1 M, more preferably about 10 mM to about 200 mM. Tonicity modifiers are well known in the art and are manufactured by known methods and available from commercial suppliers.

Excipients, also referred to as chemical additives, co-solutes, or co-solvents, that stabilize the polypeptide while in solution (also in dried or frozen forms) can also be added to a pharmaceutical composition. Excipients are well known in the art and are manufactured by known methods and available from commercial suppliers.

Examples of suitable excipients include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), dextran, poly(vinyl alcohol) PVA, hydroxypropyl methylcellulose (HPMC), polyethyleneimine, gelatin, polyvinylpyrrolidone (PVP), hydroxyethylcellulose (HEC); non-aqueous solvents such as: PEG, and glycerol and dimethylformamide (DMF); amino acids such as: proline, L-serine, sodium glutamic acid, alanine, glycine, lysine hydrochloride, sarcosine and gamma-aminobutyric acid; surfactants such as: Tween® -80 (polysorbate 80), Tween®-20 (polysorbate 20), SDS, polysorbate, poloxamers; and miscellaneous excipients such as: potassium phosphate, sodium acetate, ammonium sulfate, magnesium sulfate, sodium sulfate, trimethylamine N-oxide, betaine, metal ions (e.g., zinc, calcium, and magnesium), CHAPS, monolaurate, 2-O-beta-mannoglycerate or any combination of the above.

Preferred excipients are sucrose, lactose, glycerol, xylitol, sorbitol, mannitol, maltose, inositol, trehalose, glucose, bovine serum albumin (BSA), human serum albumin (HSA), recombinant albumin, dextran, PVA, hydroxypropyl methylcellulose (HPMC), polyethyleneimine, gelatin, polyvinylpyrrolidone (PVP), hydroxyethylcellulose (HEC), PEG, ethylene glycol, glycerol, alanine, glycine, lysine hydrochloride, sarcosine, SDS, polysorbate 20, polysorbate 80, poloxamer 188, trimethylamine N-oxide, betaine, zinc ions, calcium ions, magnesium ions, CHAPS, sucrose monolaurate, and 2-O-beta-mannoglycerate.

The concentration of one or more excipients in a formulation of the invention is/are preferably between about 0.001 to 5 weight percent, more preferably about 0.1 to 2 weight percent.

If desired, an etanercept preparation prepared according to the present invention can be used in the same formulation in which commercial ENBREL® is currently supplied, such formulation comprising, about 25 to about 75 mg/ml of the formulation, and further comprising sucrose, sodium chloride, L-arginine hydrochloride, and sodium phosphate.

Alternatively, the etanercept preparations obtained in accordance with the present invention may be supplied in a pharmaceutical formulation which does not contain arginine; for example any of the non-arginine formulations as described in Manning et al. provisional applications U.S. Ser. Nos. 61/548,518 and 61/669,480 filed Oct. 18, 2011 and Jul. 9, 2012, respectively, both of which are hereby incorporated by reference in their entirety. The non-arginine formulations formulations may contain 0 to 100 mM NaCl, e.g., 0 mM, 25 mM, 50 mM, 75 mM or 100 mM NaCl.

In another embodiment, the invention provides a method of treating a mammal comprising administering a therapeutically effective amount of the pharmaceutical compositions of the invention to a mammal, wherein the mammal has a disease or disorder that can be beneficially treated with etanercept.

In a preferred embodiment, the etanercept is derived from the same species of mammal as is to be treated with the composition.

In a preferred embodiment, the mammal is a human.

Diseases or disorders that can be treated with the provided compositions include but are not limited to rheumatoid arthritis, psoriatic arthritis, ankylosing spondylitis, Wegener's disease (granulomatosis), Crohn's disease (or inflammatory bowel disease), chronic obstructive pulmonary disease (COPD), Hepatitis C, endometriosis, asthma, cachexia, psoriasis, and atopic dermatitis. Additional diseases or disorders that can be treated with the compositions of the present invention include those described in WO 00/62790, WO 01/62272, U.S. patent application Ser. No. 2001/0021380, and U.S. Pat. No. 7,648,702 B2, the relevant portions of which are incorporated herein by reference.

The provided pharmaceutical compositions may be administered to a subject in need of treatment by injection systemically, such as by intravenous injection; or by injection or application to the relevant site, such as by direct injection, or direct application to the site when the site is exposed in surgery; or by topical application.

In one embodiment, the invention provides a method of treatment and/or prevention of rheumatoid arthritis comprises administering to a mammal in need thereof a therapeutically effective amount of one of the provided etanercept compositions.

The therapeutically effective amount of the etanercept in the provided compositions will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations.

In one embodiment, the effective etanercept amount per adult dose is from about 1-500 mg/m$^2$, or from about 1-200 mg/m$^2$, or from about 1-40 mg/m$^2$ or about 5-25 mg/m$^2$.

Alternatively, a flat dose may be administered, whose amount may range from 2-500 mg/dose, 2-100 mg/dose or from about 10-80 mg/dose.

If the dose is to be administered more than one time per week, an exemplary dose range is the same as the foregoing described dose ranges or lower and preferably administered two or more times per week at a per dose range of 25-100 mg/dose.

In another embodiment, an acceptable dose for administration by injection contains 80-100 mg/dose, or alternatively, containing 80 mg per dose.

The dose can be administered weekly, biweekly, or separated by several weeks (for example 2 to 8).

In one embodiment, etanercept is administered at 25 to 75 mg/ml by a single subcutaneous (SC) injection.

In some instances, an improvement in a patient's condition will be obtained by administering a dose of up to about 100 mg of the pharmaceutical composition one to three times per week over a period of at least three weeks. Treatment for longer periods may be necessary to induce the desired degree of improvement. For incurable chronic conditions the regimen may be continued indefinitely. For pediatric patients (ages 4-17), a suitable regimen may involve administering a dose of 0.4 mg/kg to 5 mg/kg of etanercept, one or more times per week.

In another embodiment, the pharmaceutical formulations of the invention may be prepared in a bulk formulation, and as such, the components of the pharmaceutical composition are adjusted to be higher than would be required for administration and diluted appropriately prior to administration.

The pharmaceutical compositions can be administered as a sole therapeutic or in combination with additional therapies as needed. Thus, in one embodiment, the provided methods of treatment and/or prevention are used in combination with administering a therapeutically effective amount of another active agent. The other active agent may be administered before, during, or after administering the pharmaceutical compositions of the present invention. Another active agent may be administered either as a part of the provided compositions, or alternatively, as a separate formulation.

Administration of the provided pharmaceutical compositions can be achieved in various ways, including parenteral, oral, buccal, nasal, rectal, intraperitoneal, intradermal, transdermal, subcutaneous, intravenous, intra-arterial, intracardiac, intraventricular, intracranial, intratracheal, intrathecal administration, intramuscular injection, intravitreous injection, and topical application.

The pharmaceutical compositions of this invention are particularly useful for parenteral administration, i.e., subcutaneously, intramuscularly, intravenously, intraperitoneal, intracerebrospinal, intra-articular, intrasynovial, and/or intrathecal. Parenteral administration can be by bolus injection or continuous infusion. Pharmaceutical compositions for injection may be presented in unit dosage form, e.g., in ampoules or in multi-dose containers, with an added preservative. In addition, a number of recent drug delivery approaches have been developed and the pharmaceutical compositions of the present invention are suitable for administration using these new methods, e.g., Inject-ease®, Genject®, injector pens such as GenPen®, and needleless devices such as MediJector® and BioJector®. The present pharmaceutical composition can also be adapted for yet to be discovered administration methods. See also Langer, 1990, Science, 249:1527-1533.

The provided pharmaceutical compositions can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. The syringe can be accompanied by instructions for administration.

In another embodiment, the present invention is directed to a kit or container, which contains an aqueous pharmaceutical composition of the invention. The concentration of the polypeptide in the aqueous pharmaceutical composition can vary over a wide range, but is generally within the range of from about 0.05 to about 20,000 micrograms per milliliter (μg/ml) of aqueous formulation. The kit can also be accompanied by instructions for use.

The present invention is more particularly described in the following examples that are intended as illustrative only, since many modifications and variations therein will be apparent to those skilled in the art. Further representative embodiments of the present invention are provided below.

Example 1

Capto™ MMC Mixed Mode Purification Using NaCl Elution

Figure 3A:
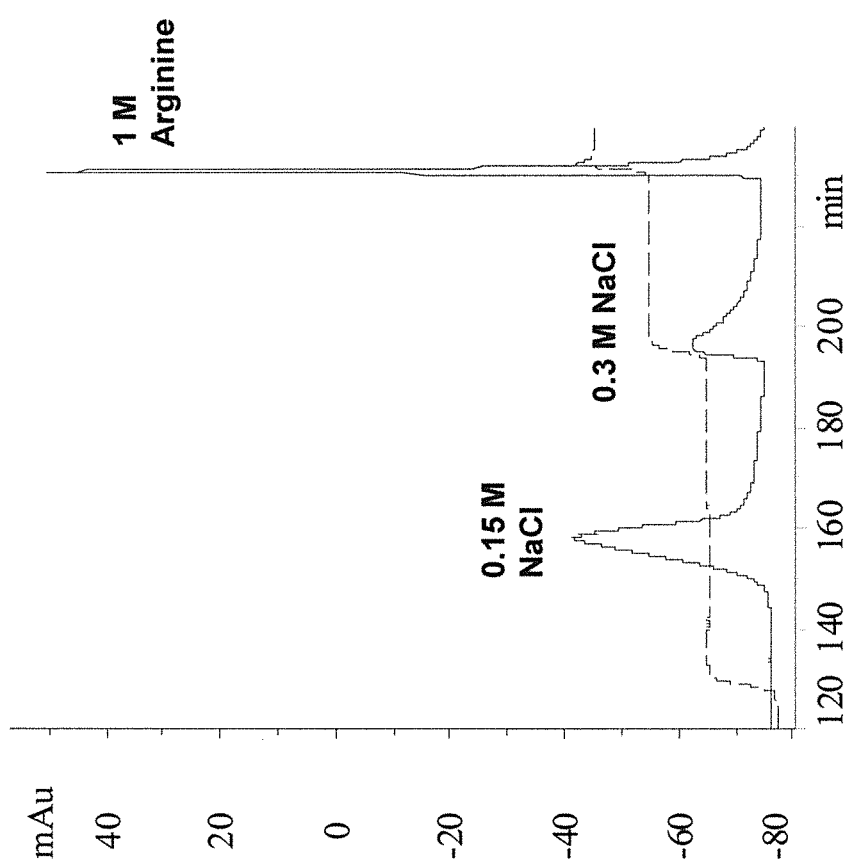
FIG. 3A (elution profile of Protein A pool from Capto MMC) shows a CAPTO MMC chromatogram of elution by NaCl or arginine in 10 mM phosphate, pH 7.5.
Figure 3B:
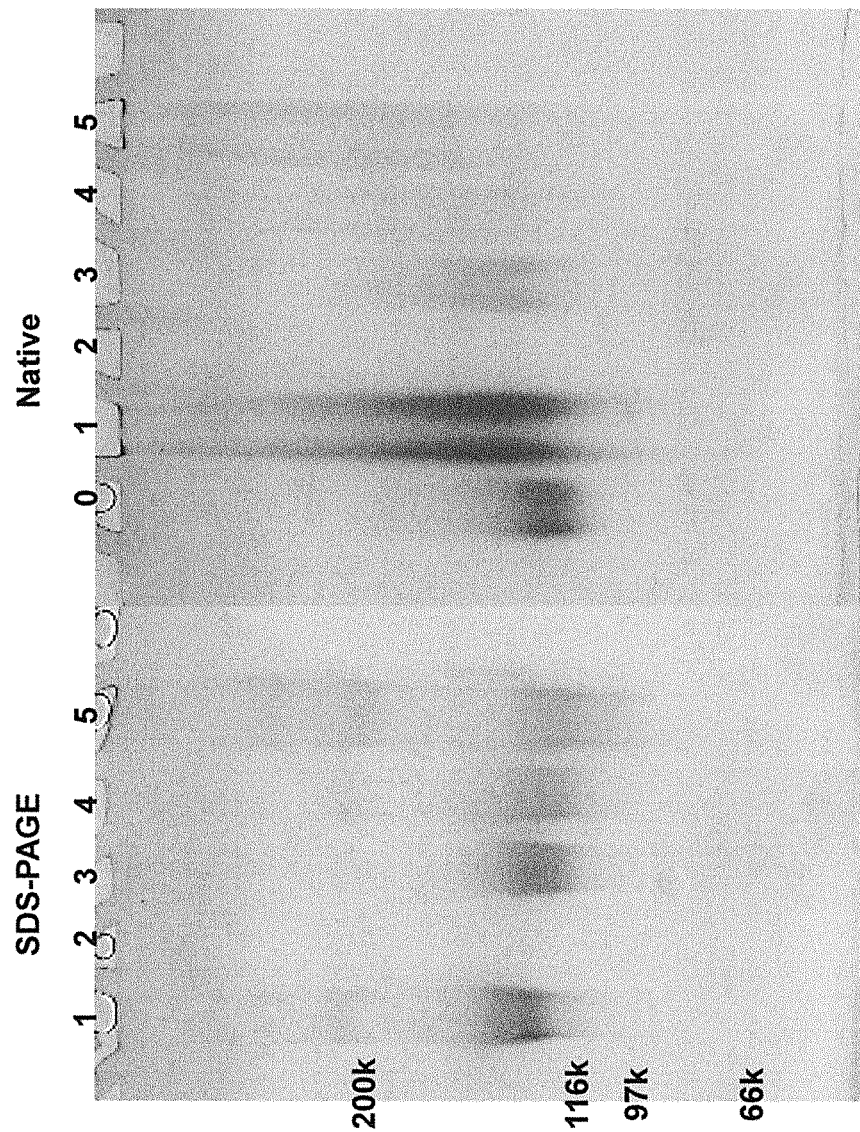
FIG. 3B (elution profile of Protein A pool from Capto MMC) SDS-PAGE and native-PAGE of eluted samples) wherein Lane-0, standard; lane-1, Load; lane-2, FT; lane-3, 0.15 M NaCl; lane-4, 0.3 M NaCl; lane-5, 1 M arginine.

In this example, a Protein A eluate obtained as described above is subjected to Capto™ MMC chromatography. The Capto™ MMC column is equilibrated with a 5 mM citrate, pH 4.5 solution. An appropriate dilution of Protein A eluate (e.g., 3 to 6 fold dilution depending on the elution buffer of Protein A step) with 5 mM citrate results in complete binding to the column. As was shown in SDS-PAGE analyses, the loading sample (pH 4.2, Protein A eluate) is highly heterogeneous and no protein flows through the Capto™ MMC column. The bound proteins is then eluted with a 0.15 M NaCl in 10 mM phosphate, pH 7.5 solution which leads to a simultaneous change in pH (from 4.5 to 7.5) and NaCl concentration (from 0 to 0.15 M). A sharp elution peak containing correctly folded etanercept is observed from analysis of the eluate. However, the recovery was about 40-50%. Following the elution step as just described, the resin containing the remaining bound protein material is contacted with 0.3 M NaCl and the 1M arginine in 10 mM phosphate, pH 7.5 solutions which results in elutions containing mainly misfolded species as well as disulfide-linked aggregates. This example demonstrates that Capto™ MMC is effective in separating the misfolded species from the correctly folded species. The fact that the misfolded species elute at a higher salt concentration (0.3 M vs. 0.1 M) means that they have a stronger electrostatic interaction with the column. In addition, 1 M arginine further increases the elution of misfolded and also aggregated proteins, indicating that these proteins are bound to the Capto™ MMC not only through electrostatic interaction but also hydrophobic interaction and that arginine enhances disruption of both electrostatic and hydrophobic interactions. Analysis of the eluate fractions obtained in this example are represented in FIGS. 3A and 3B.

Example 2

Capto™ MMC Mixed Mode Purification Using NaCl

Resin Equilibrated to pH 7.5

In the foregoing example, the protein solution comprising correctly folded and incorrectly folded etanercept was initially contacted with the CAPTO MMC resin at pH 4.5. In this example, a similar elution to that observed in Example 1 is observed when the Capto™ MMC column is first equilibrated with a 10 mM phosphate, pH 7.5 solution and then eluted with NaCl followed by arginine. Specifically, no etanercept is eluted during this pH equilibration. This result is unexpected because etanercept is negatively charged at pH 7.5; the pI of etanercept ranges from 4.9 to 5.4 due to heavy glycosylation. Thus, at or below pH 4.5, etanercept is positively charged and hence should bind to the negatively charged Capto™ MMC ligands, although hydrophobic interaction may contribute to the binding. At pH 7.5, the negatively charged etanercept should dissociate from the negatively charged Capto™ MMC, but it is found that this does not occur. This may be explained by the hydrophobic interaction between etanercept and Capto™ MMC overwhelming the electrostatic repulsion between negatively charged column and etanercept. Alternatively, Capto™ MMC may hold the bound protein by binding to the local positive charges on the protein moiety (pI of protein moiety is ~8.1).

Example 3

Capto™ MMC Mixed Mode Purification Using NaCl Gradient for Elution

In this example, successful elution is accomplished using an NaCl concentration gradient. Specifically, after washing the column with the 10 mM phosphate, pH 7.5 solution, the bound proteins were eluted with linear salt gradient from 0 to 0.5 M. The loading sample (pH 4.2 Protein A eluate) is extremely heterogeneous (containing both correctly folded and incorrectly folded etanercept) as in the previous case, and the bound proteins are eluted with increasing ionic strength of the NaCl gradient. After 180 min, the gradient is terminated and salt concentration is then brought to 0.5 M, which caused a slightly enhanced protein elution. As determined by subsequent analyses, low salt fractions contain more of the correctly folded etanercept and higher salt fractions were enriched with low mobility (misfolded and aggregated) species. Finally, the remaining proteins is eluted with a 1 M arginine, 10 mM phosphate, pH 7.5 solution. This fraction contains no etanercept, but entirely low mobility (misfolded/aggregated) species. The use of the NaCl gradient elution of Capto™ MMC on different Protein A eluates, combined with a preliminary equilibrium of the resin results in a more pure eluate in terms of correctly folded etanercept. At low NaCl concentrations in the elution media, the eluted samples are enriched with the folded etanercept. The misfolded species gradually increase in the eluate as the salt gradient described above is applied to the resin. After the salt gradient is completed, the resin is contacted with the 1 M arginine solution, and the eluate fraction resulting therefrom is found to contain misfolded species (which include not only misfolded but also aggregated species) as is evident in subsequent SDS-PAGE analysis. Some of the low mobility species are believed to be incorrectly folded (but non-aggregated) etanercept on SDS-PAGE, indicating that a portion of misfolded species migrate as misfolded etanercept homodimer with slower mobility on native-PAGE than the correctly folded etanercept homodimer. Analysis of eluate fractions obtained in this example are provided in FIGS. 4A, 4B and 4C.

Example 4

Capto™ MMC Mixed Mode Purification Using $Na_2SO_4$ Gradent for Elution

Figure 5A:
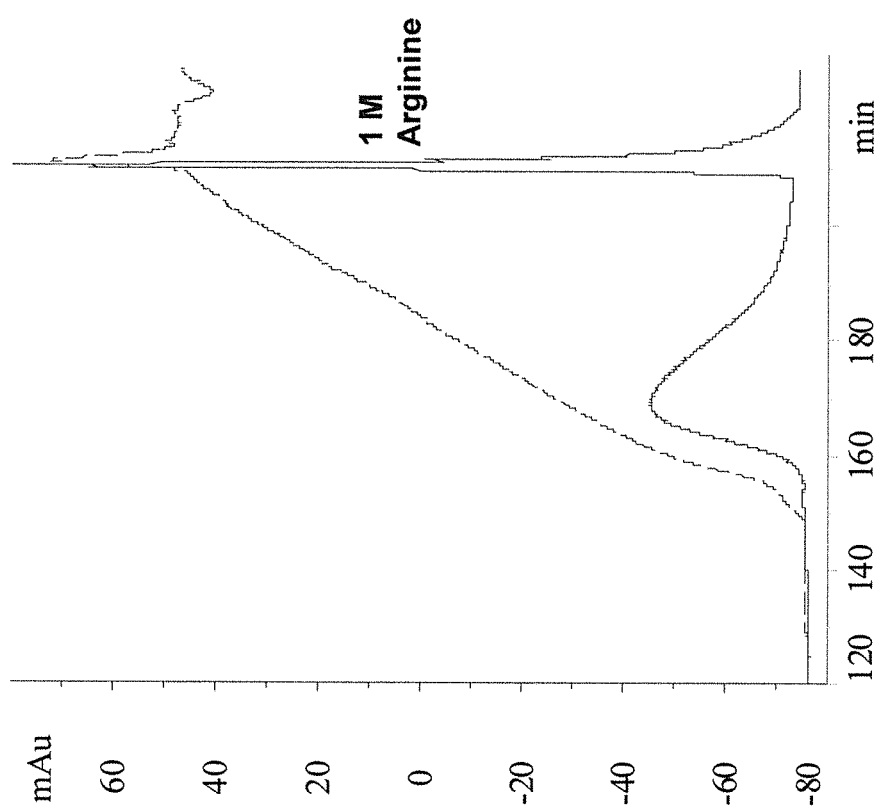
FIG. 5A (Elution profile of Protein-A pool from Capto-MMC) Chromatogram of elution by 0-0.4 M $Na_2SO_4$ gradient at pH 7.5. The column was equilibrated with 10 mM phosphate, pH 7.5 before gradient elution.
Figure 5B:
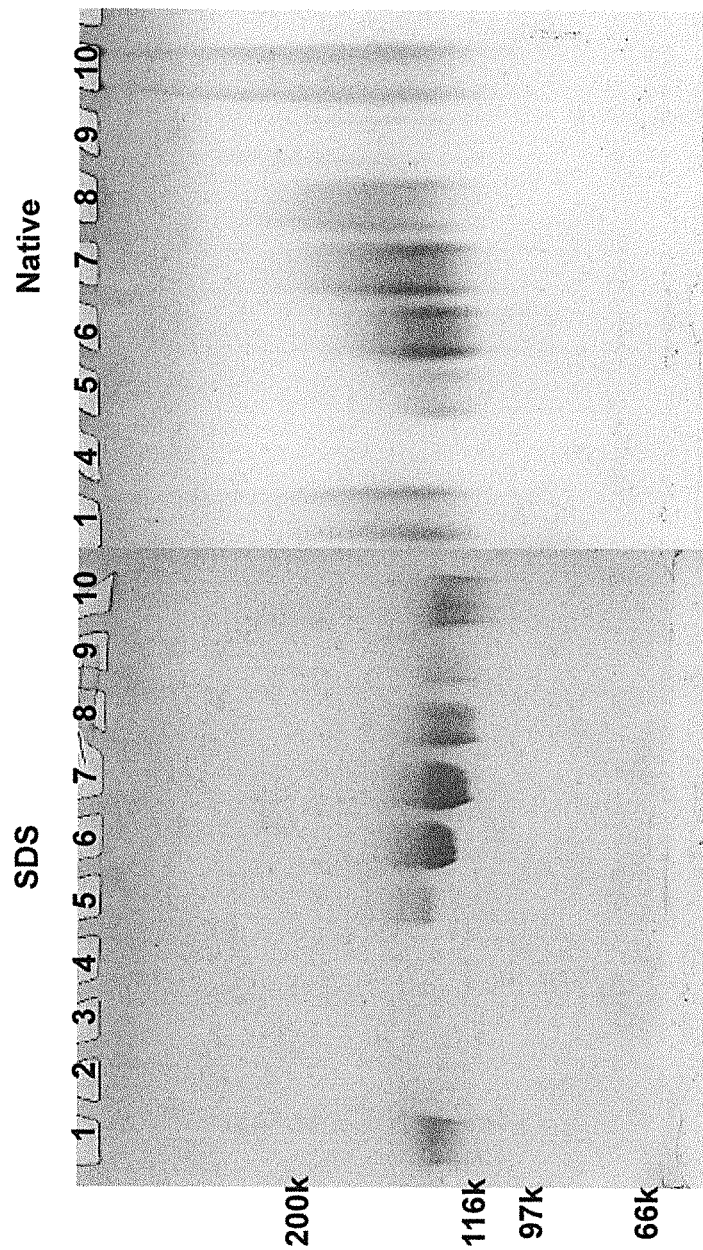
FIG. 5B. (Elution profile of Protein-A pool from Capto-MMC) SDS-PAGE and native-PAGE of eluted samples wherein; lane-1, Load; lane-2, FT; lane-3, buffer wash; lane-4 to lane-9, eluted fractions; lane-10, 1 M arginine.

In this example a $Na_2SO_4$ gradient instead of the NaCl is used as the salt gradient for elution of correctly folded etanercept from the mixed mode resin. While NaCl is in general exclusively used to elute proteins in IEC, it is generally known that different salts have varying degrees of salting-out (precipitation of protein) effects. NaCl is an intermediate between salting-in salts, such as $MgCl_2$, and salting-out salts, such as $Na_2SO_4$. NaCl may be effective in weakening the electrostatic interaction between etanercept and Capto™ MMC, but may be neutral in weakening hydrophobic interaction. It was thought herein that $Na_2SO_4$ should also be effective in weakening the electrostatic interaction, but should enhance the hydrophobic interaction because it is known as a strong salting-out salt. Thus, if the low mobility species are bound by the column by hydrophobic interaction as indicated above, their elution may be suppressed by $Na_2SO_4$. This is tested by elution of the protein solution containing correctly folded and incorrectly folded etanercept with an $Na_2SO_4$ gradient from 0 to 0.4 M, after pH equilibration of the CAPTO MMC resin column with a 10 mM phosphate, pH 7.5 solution. After the $Na_2SO_4$ gradient elution of the proteins is completed, the column is washed with a 1 M arginine, pH 7.5 solution. FIG. 5A shows elution chromatogram, while FIG. 5B shows the SDS-PAGE and native-PAGE of the eluted fractions. A relatively sharp band of correctly folded etanercept is observed in low $Na_2SO_4$ fractions (lanes 6 and 7 FIG. 5B) and the purity of these fractions is greater than the load (lane 1). Higher $Na_2SO_4$ concentrations results in elution of low mobility species on native-PAGE (lanes 8 and 9 FIG. 5B). A final 1 M arginine elution at pH 7.5 results in elution of low mobility (misfolded/aggregated) species. There appears to be some etanercept in this fraction (lane 10 FIG. 5B), indicating that $Na_2SO_4$ may also suppress elution of the native etanercept. It may be concluded that $Na_2SO_4$ is equally, if not more, effective in separating the folded species from the misfolded species, although it may cause retention of native etanercept (lane 10).

Example 5

Capto™ MMC Mixed Mode Purification Using Elution with NaCl and pH Gradient

Figure 4B:
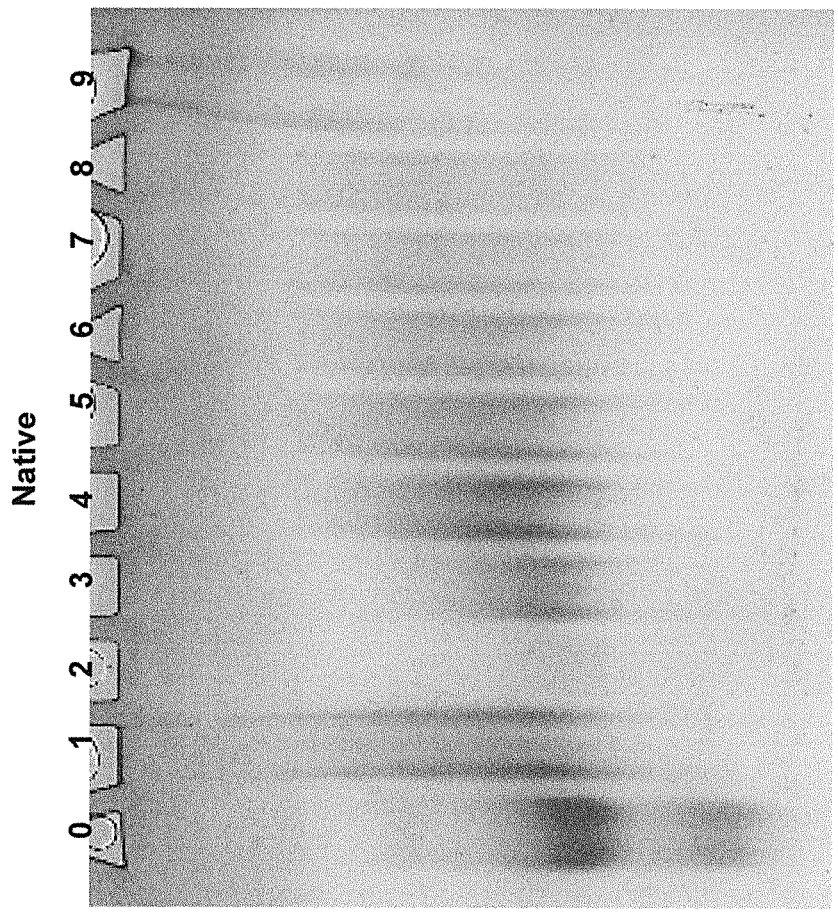
FIG. 4B (Elution profile of Protein A pool from Capto MMC) shows native-PAGE of eluted samples wherein: Lane-0, standard; lane-1, Load; lane-2 to lane-8, eluted fractions; lane-9, 1 M arginine.
Figure 7A:
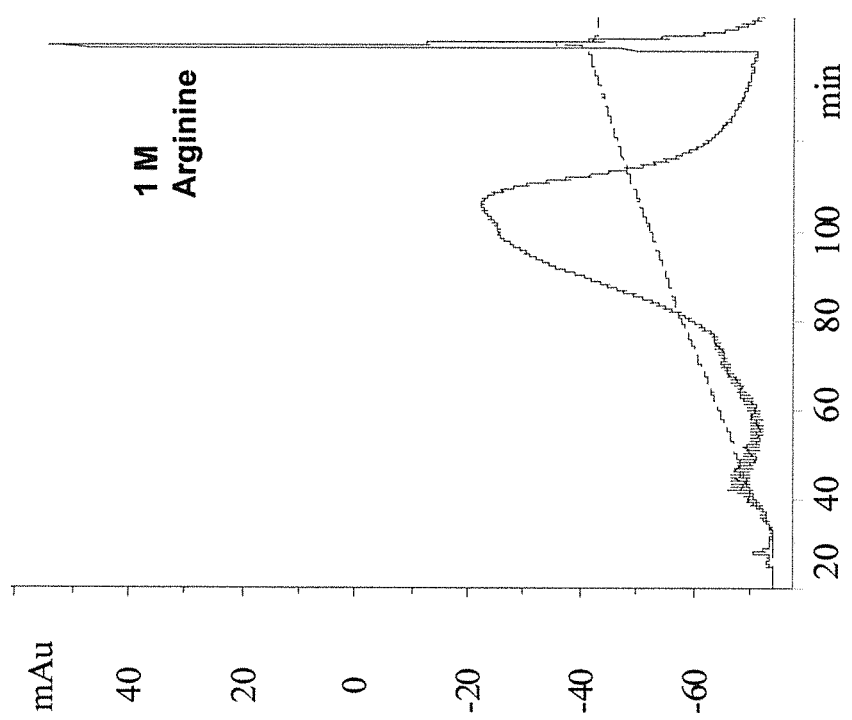
FIG. 7A (Elution profile of Protein-A pool from Capto-MMC) shows a chromatogram of elution by pH and salt gradient.
Figure 7B:
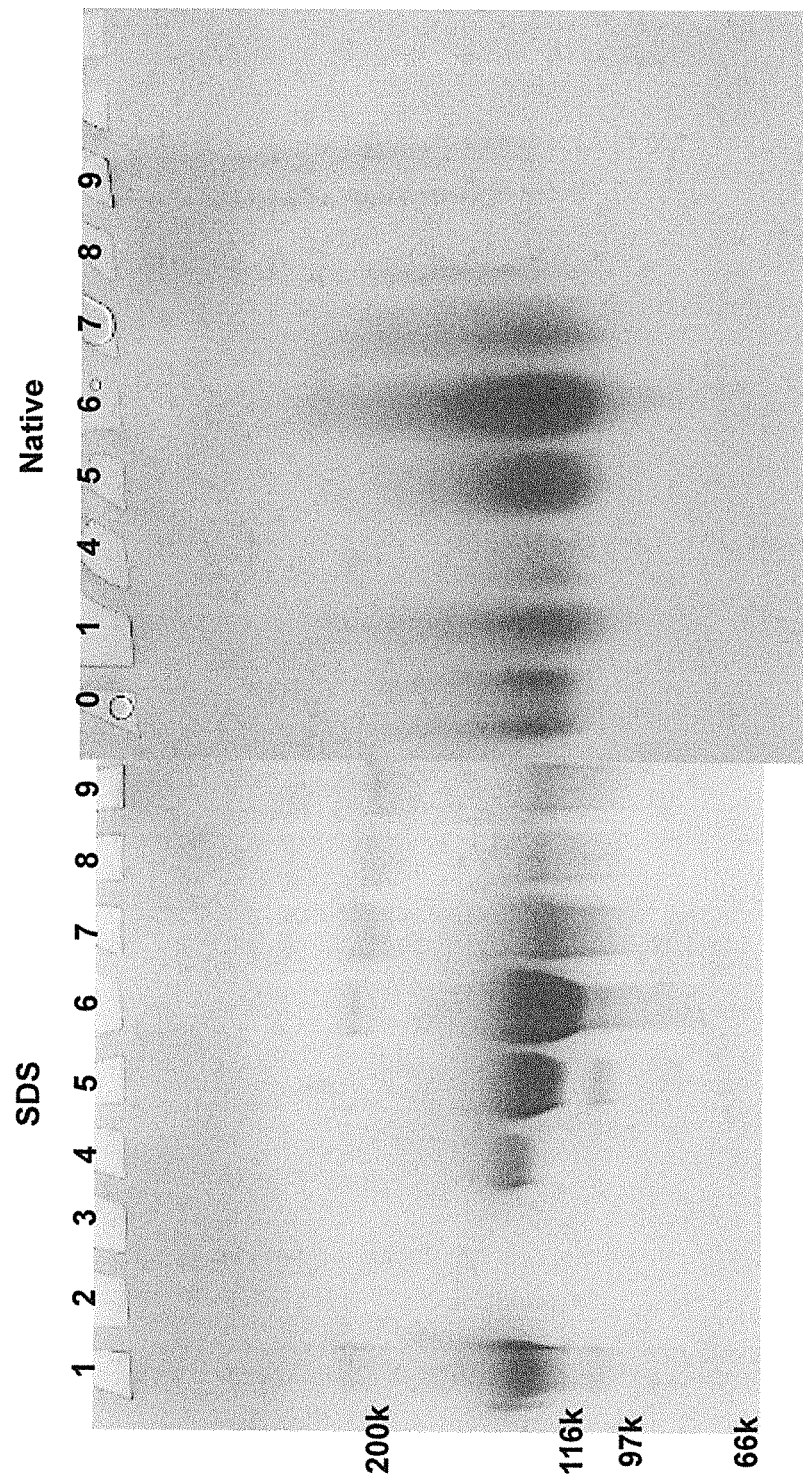
FIG. 7B (Elution profile of Protein-A pool from Capto-MMC) shows SDS-PAGE and native-PAGE of eluted samples wherein Lane-0, standard; lane-1, Load; lane-2 and 3, FT; lane-4 to lane-8, eluted fractions; lane-9, 1 M arginine.

In the preceding examples no proteins are observed to elute during pH equilibration step, i.e., pH change from 4.5 (5 mM citrate) to 7.5 (10 mM phosphate). When the amount of protein loading is increased over 10 mg per 1 ml column, however, this is no longer the case. An increasing elution of the proteins during the pH change occurrs at higher loading, although the reason for this observation is not clear. The purity of this eluted sample is greater than the loading samples, but is far less than the low salt fractions. For example, when the loading sample (Protein A eluate) contains only 51% correctly folded etanercept species, the elution that occurrs during pH equilibration is only 65% pure, higher than the load but far below the low salt fractions, whereas, the salt elutions in the above examples are able to give a 96% purity at the beginning of the salt gradient, as determined by analytical HIC (FIG. 6). As plotted in FIG. 6, the purity of the eluted fractions gradually decreases from 96% to 20% with increasing salt concentrations, consistent with the native-PAGE result for Capto™ MMC (FIGS. 3B, 4B, 5B). The purity of 1 M arginine fraction (in terms of correctly folded etanercept) was low (only 11%), also consistent with the native-PAGE analysis (see FIG. 4B. lane 9 and FIG. 5B, lane 10). In view of the foregoing observations, it is postulated in connection with the discoveries embodied herein that it may be beneficial to combine a pH gradient with a salt gradient in order to counteract potential loss of any correctly folded species during the column pH equilibration for a larger protein loading. Accordingly, in this Example 5 below, a pH gradient is combined with a salt gradient when conducting the above defined step (b) of the present method. In this Example the possibility that small amounts of properly folded etanercept may be undesirably eluted during initial pH equilibrium of the mixed mode resin column is counteracted by combining a pH change with a salt gradient. Specifically, the bound protein is eluted by a simultaneous gradient of both pH and NaCl concentration, i.e., the column is developed from a 5 mM citrate, pH 4.5 solution to a 10 mM phosphate, pH 7.5 solution, containing NaCl. This results in simultaneous changes of both pH and salt concentration, both causing elution of the bound proteins. This is similar to the salt elution profile after the pH equilibrium was observed in that the low mobility species eluted in later fractions (i.e., at higher pH and salt concentration) and in the final 1 M arginine, pH 7.5 wash. For example, Protein A eluate (24 mg) is bound to the column at pH 4.5 and is eluted by a gradient from 5 mM citrate, pH 4.5 to 10 mM phosphate pH 7.5 containing 0.5 M NaCl. It is postulated that this large load with pH equilibration could lead to elution of the bound proteins during pH shift. The elution profile during the pH and salt gradient indeed shows a small peak at the beginning of the gradient and a major peak (the desired correctly folded etanercept) at the intermediate of the gradient. The observed small peak may correspond to the elution that would have been observed if pH equilibration were performed initially without a pH/salt gradient. After the NaCl/pH gradient elution is completed, the column is then subject to further elution with 1 M arginine solution which results in a final sharp peak corresponding to low mobility species. Early eluting low salt and low pH fractions are enriched with etanercept, while high salt and high pH fractions showed elution of low mobility species; the pH gradually increased from 4.5 to 7.5, e.g., pH 4.1-5.1 in the intermediate salt concentrations and pH 6.6 at the end of gradient. The final wash with the 1 M arginine, pH 7.5 solution, shows a smearing band on native-PAGE and multiple bands on SDS-PAGE, essentially identical to the elution that results after initial column equilibration causing pH shift with 10 mM phosphate, pH 7.5 wash. The recovery of properly folded etanercept in the pool was ~70%. A similar result is obtained when elution is carried out with the same pH/salt gradient to the 10 mM phosphate, pH 7.5 solution but ending at a lower salt containing 0.25 M NaCl. This gradient using a lower salt concentration results in incomplete elution of etanercept with a yield of ~50%. As in the previous examples, a large peak was observed with 1 M arginine wash, corresponding to low mobility (misfolded/aggregated) etanercept species. Analysis of the eluates obtained in this example are represented in FIGS. 7A and 7B Example 6

Capto™ MMC Mixed Mode Purification Using $Na_2SO_4$/pH Gradient for Elution

Figure 8A:
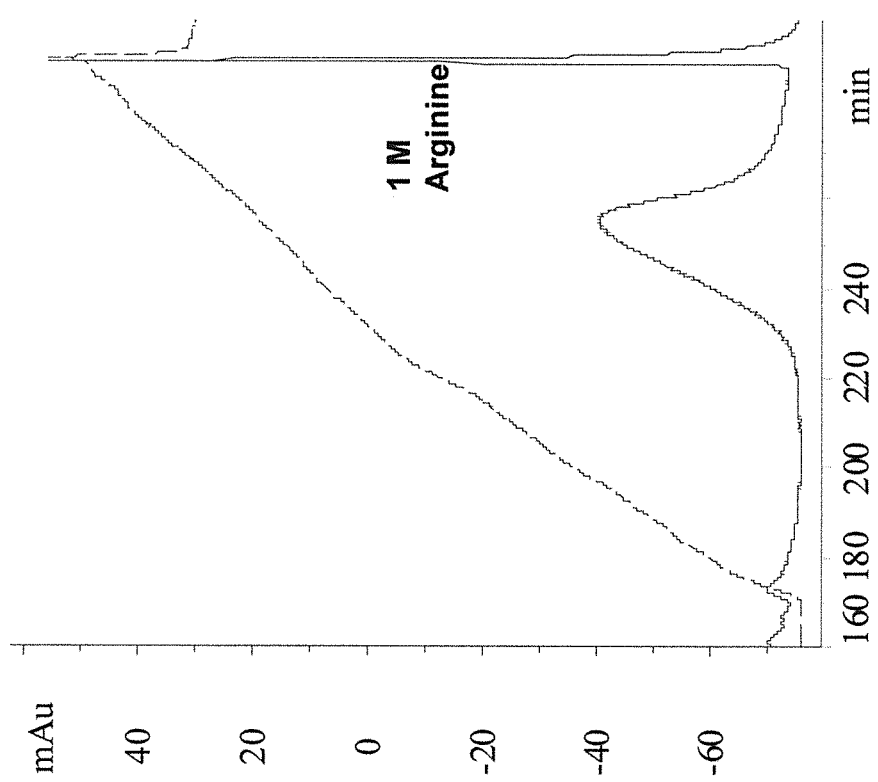
FIG. 8A (Elution profile of Protein-A pool from Capto-MMC) shows a chromatogram of elution by pH and $Na_2SO_4$ gradient.
Figure 8B:
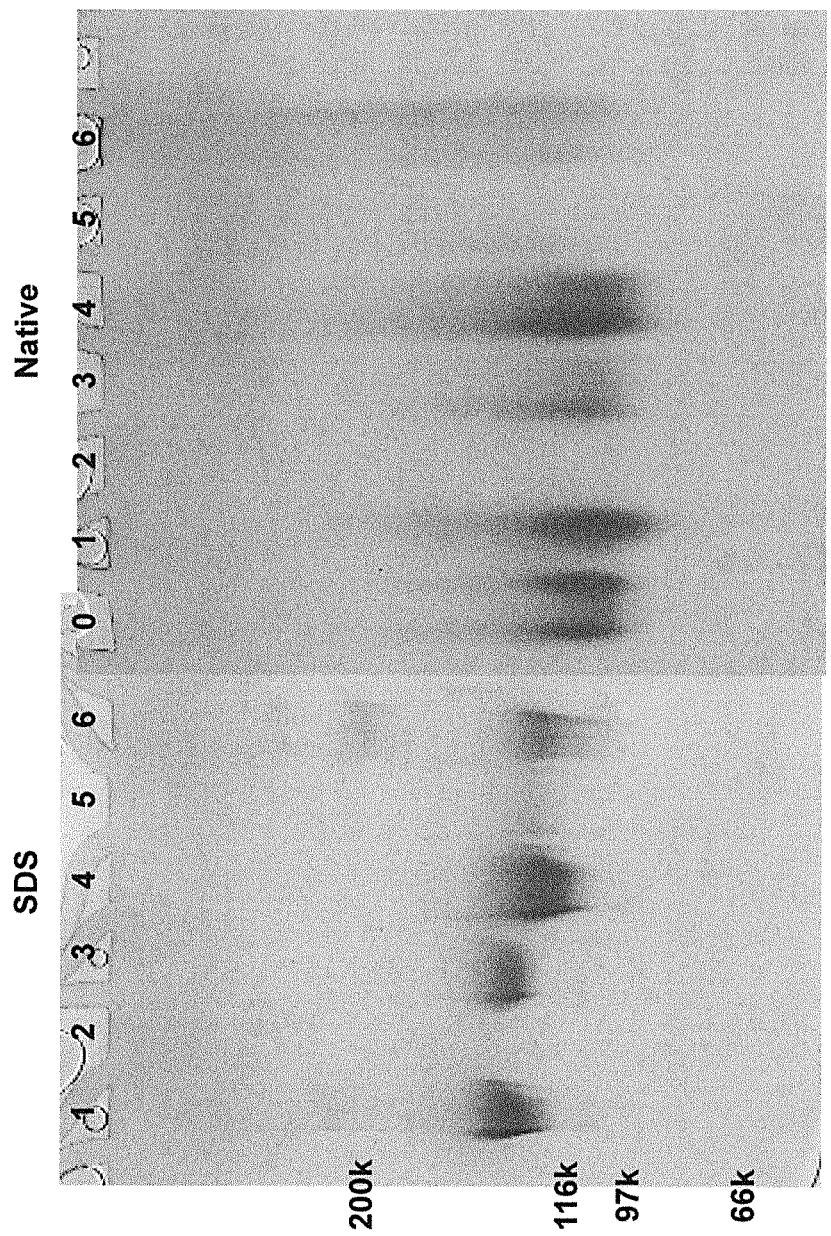
FIG. 8B (Elution profile of Protein-A pool from Capto-MMC) shows SDS-PAGE and native-PAGE of eluted samples wherein Lane-0, standard; lane-1, Load; lane-2, FT; lane-3 to lane-5, eluted fractions; lane-6, 1 M arginine.

Similar to the procedures used in Example 5 above, a pH/salt gradient elution was also carried out using a 0.5 M $Na_2SO_4$ solution as the final solvent, which is thought to improve resolution of the folded species from the misfolded species. The recovery of etanercept in pool is ~50%, and the low recovery is believed due to enhanced hydrophobic interaction by 0.5 M $Na_2SO_4$, leading to retention of not only misfolded species mostly eluting in 1 M arginine wash, but also the etanercept, which also appeared in 1 M arginine wash. Thus, use of $Na_2SO_4$ can enhance the separation (i.e. resolution) of misfolded from correctly folded species, but also reduces the recovery of etanercept. For analysis of the eluates in this Example, reference may be had to FIGS. 8A and 8B.

Example 7

Capto™ Adhere; Elution with NaCl at pH 7.5 and pH 4.5

In this example, a Protein A eluate comprising both correctly and incorrectly folded etanercept species is subjected to mixed-mode chromatography using Capto™ Adhere as the mixed mode resin. The binding of the protein solution comprising correctly folded and incorrectly folded etanercept species was performed at pH 7.5, at which etanercept is negatively charged and hence should bind to the positively charged Capto™ Adhere ligands. When the pH 4.2 Protein A eluate is dialyzed versus the 10 mM phosphate, pH 7.5 solution, protein binding is complete, but elution by salt alone (at pH 7.5) is found to be ineffective, suggesting that Capto™ Adhere is considerably hydrophobic. It is therefore considered that, because the pI of etanercept is 4.9-5.4, that at a lower elution pH of perhaps pH 4.5 the etanercept species would be positively charged and hence repelled from the positively charged Capto™ Adhere resin at pH 4.5. This possibility is investigated by conducting elution of etanercept species from Capto™ Adhere at pH 4.5. The pH 4.2 Protein A eluate (that has been dialyzed to pH 7.5) is bound to the Capto™ Adhere equilibrated with a 10 mM phosphate, pH 7.5 solution. Following the protein loading, the column is washed with 0 and 0.2 M NaCl in the same buffer, with no protein eluting in these washes.

Example 8

Capto™ Adhere; Elution with/without Arginine at pH 4.5

Figure 9:
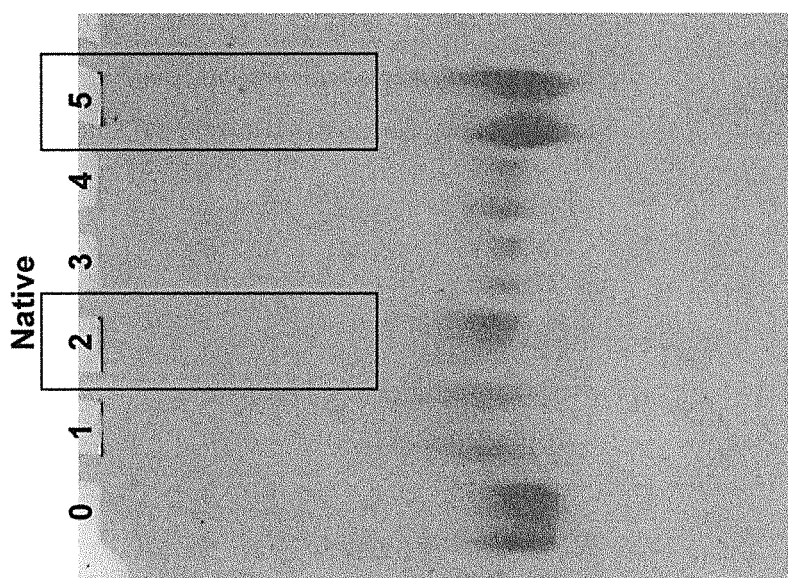
FIG. 9 shows Native-PAGE of Protein-A pool from Capto-Adhere wherein Lane-0, standard; lane-1, Load; lane-2, 5 mM citrate (pH 4,5); lane-3 and 4, 0.1 M arginine (pH 4.5); lane-5, 0.5 M arginine. Low molecular weight species observed are boxed.

In light of the results of Example 7, The bound protein is then eluted with a 5 mM citrate, pH 4.5 solution with and without arginine. Arginine, instead of NaCl, is used in this example to investigate the manner in which a more hydrophobic species (arginine) might impact elution in light of the hydrophobic nature of the Capto™ Adhere ligands. It is found that low mobility (misfolded/aggregated) species along with correctly folded etanercept are eluted with a 5 mM citrate, pH 4.5 wash solution (containing no arginine). Elution of the low mobility species in this fraction may be due to a sudden change in pH, as the measured pH of this fraction was 3.0. When this step is repeated with 0.1 and 0.2 M arginine in a 5 mM citrate, pH 4.5 solution, only marginal amounts of correctly folded etanercept are observed. Complete elution of the correctly folded etanercept required 0.5 M arginine, however the eluate includes an undesired amount of low mobility species. Thus, it is found that even at pH 4.5, arginine is ineffective at low concentrations, and at higher arginine concentrations, resulted in poor resolution between the folded and misfolded species. See FIG. 9 for analysis of the eluates obtained in this example.

Example 9

Capto™ Adhere; Elution with Two Arginine Gradients and pH Gradient of 7.5 to 4.5

Figure 10B:
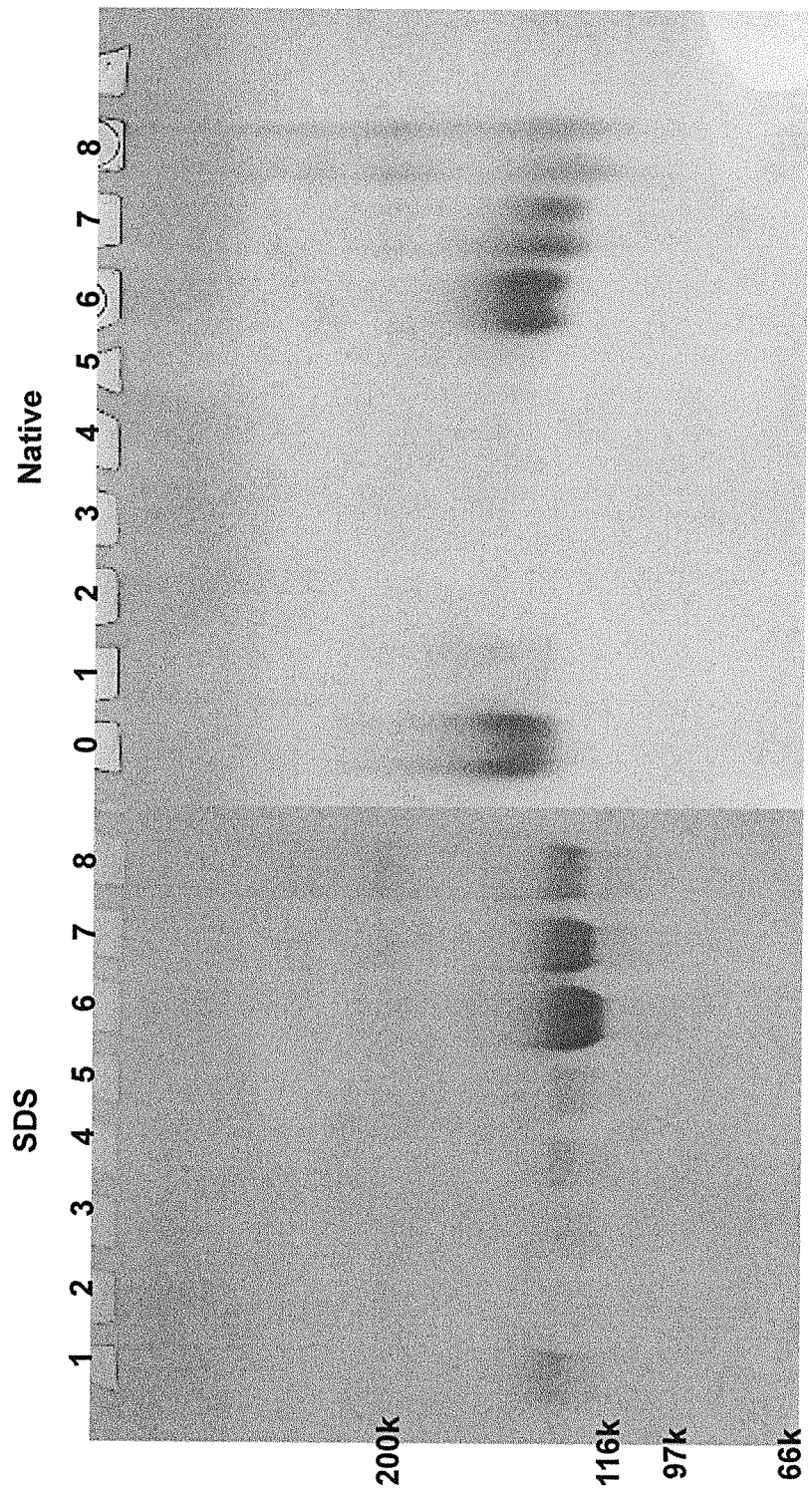
FIG. 10B (Elution profile of Protein-A pool from Capto-Adhere) shows SDS-PAGE and native-PAGE of eluted samples wherein: Lane-0, standard; lane-1, Load; lane-2 to lane-4, FT; lane-5 to lane-7, eluted fractions; lane-8, 0.5 M arginine.
Figure 11A:
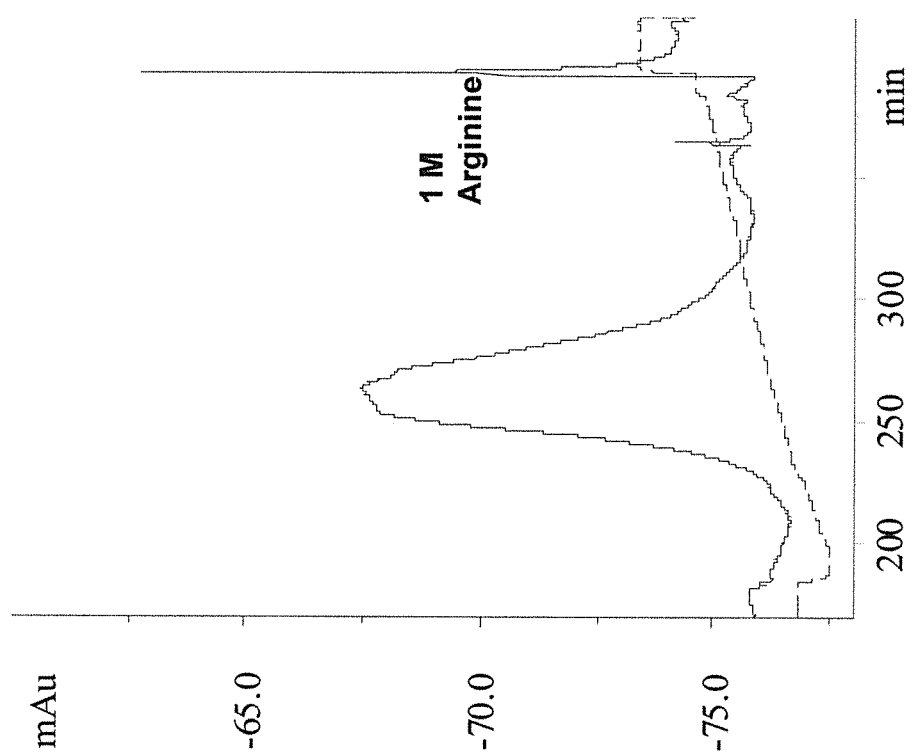
FIG. 11A (Elution profile of Protein-A pool from Capto-Adhere) shows a Chromatogram of elution by pH and arginine gradient.
Figure 11B:
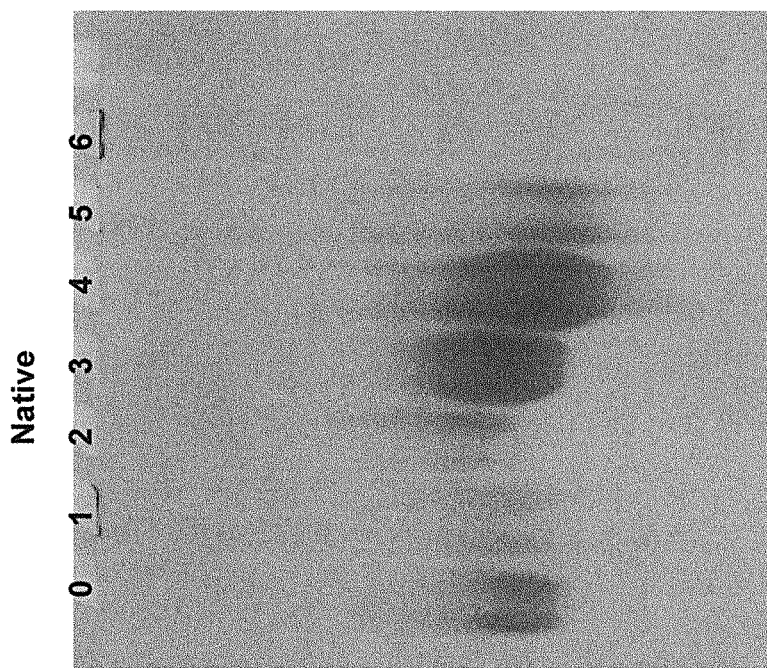
FIG. 11B (Elution profile of Protein-A pool from Capto-Adhere) shows native-PAGE of eluted samples wherein Lane-0, standard; lane-1, Load; lane-2, FT; lane-3 to lane-5, eluted fractions; lane-6, 1 M arginine.

It is then postulated that a combined pH/arginine gradient might result in better resolution between properly folded and misfolded species. As in the previous examples for CAPTO MMC, a pH drop during pH equilibration from 7.5 to 4.5 using 5 mM citrate can be prevented by applying a simultaneous gradient of pH which can then be coupled with an arginine concentration gradient (for example a gradient from 10 mM phosphate, pH 7.5 to 5 mM citrate, pH 4.5 containing arginine). Two arginine gradients were investigated with this pH gradient. In the case of an arginine gradient to 0.25 M arginine, (FIGS. 10A and 10B) it is found that a final 0.5 M arginine wash resulted in elution of both low mobility species and etanercept, indicating that the use of a gradient to an arginine concentration of only 0.25 M arginine would be insufficient for complete elution of correctly folded etanercept. Accordingly, an arginine gradient from 0-0.5 M (coupled with the above pH gradient of 7.5 to 4.5) was investigated (FIGS. 11A and 11B). It is evident from subsequent native-PAGE analysis that the relative peak height was smaller for the final 1 M arginine wash with the higher arginine gradient than the previous 0.25 M arginine gradient. No second peak is observed suggesting that resolution may have been compromised. The pH gradient is such that the pH of the eluted fractions gradually decrease from 7.5 to 6.0, 5.7, 5.2 and finally 4.5. With regard to the 0.5 M arginine and pH gradient, two fractions in the main elution peak are enriched with correctly folded etanercept with a recovery of protein at ~65%. The later part of the gradient showed a smearing band containing etanercept. Thus, although 0.5 M arginine gradient along with pH gradient enhanced elution of the bound etanercept, the correctly folded etanercept co-eluted with the misfolded species in the later part of the arginine/pH gradient. The final 1 M arginine wash showed only a smearing band.

Example 10

Capto™ Adhere; Elution with Arginine Gradient and pH Gradient of 7.5 to 4.5

Figure 13:
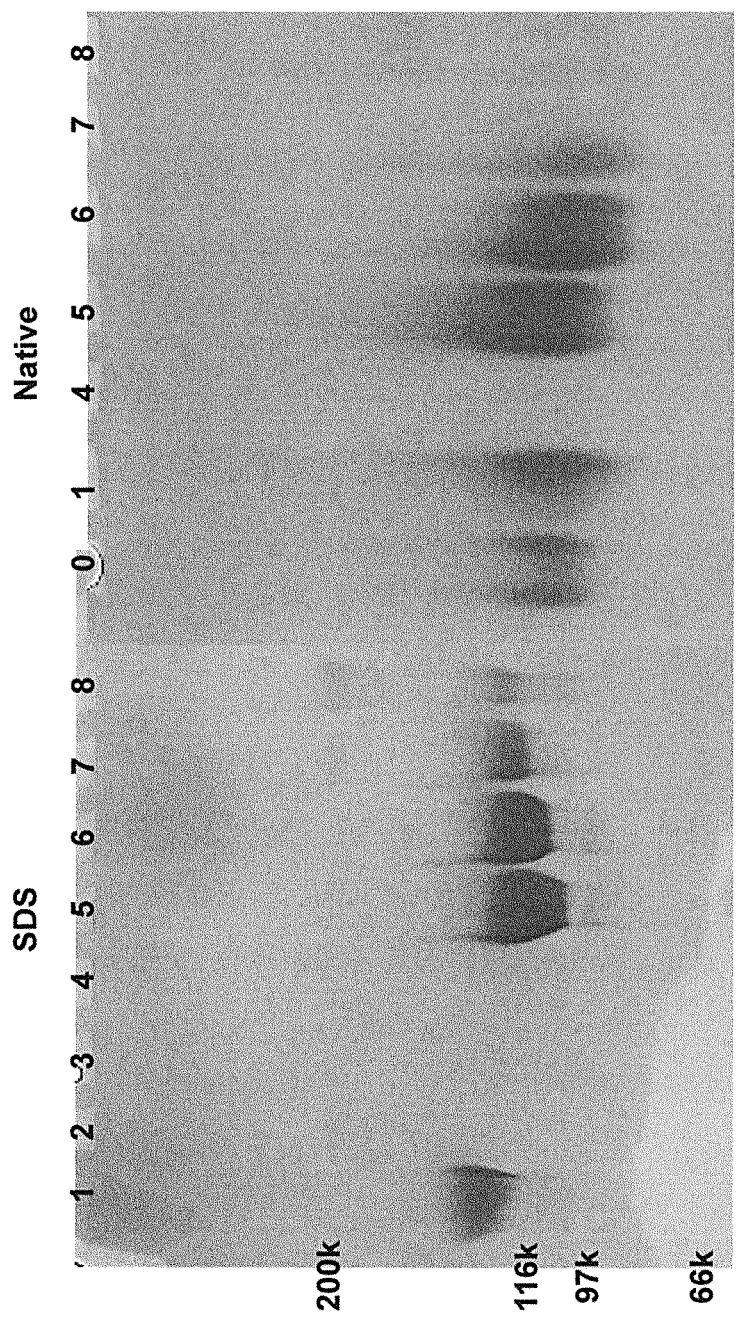
FIG. 13 (Elution profile of Capto-MMC pool from Capto-Adhere) shows SDS and Native-PAGE of eluted samples. Elution was done with arginine gradient at pH 7.5. wherein: Lane-0, standard; lane-1, Load; lane-2 and 3, FT; lane-4 to lane-7, eluted fractions; lane-8, 1 M arginine.
Figure 14:
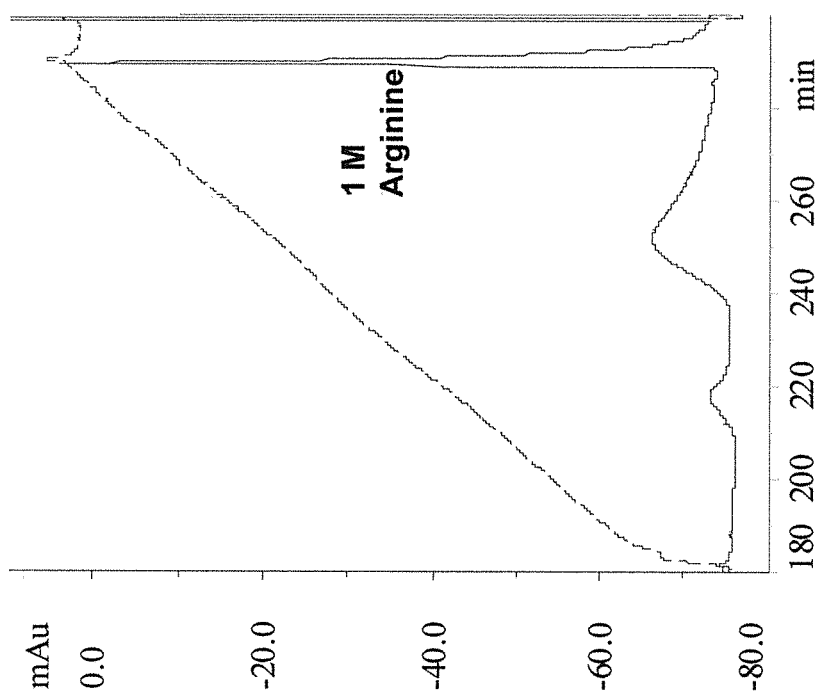
FIG. 14 is an elution chromatogram of Capto-MMC pool from Capto-Adhere. Elution was done by NaCl gradient at pH 7.5.

Arginine gradient elutions are also performed at pH 7.5 using Capto™ MMC pools. Bound proteins were eluted with a gradient from 10 mM phosphate, pH 7.5 to 0.6 M arginine, 10 mM phosphate, pH 7.5. SDS-PAGE and native-PAGE profiles show elution of correctly folded etanercept in the middle fractions (0.2-0.4 M arginine) (FIG. 13). Low mobility species as seen in both gels are observed in the later fraction and a final 1 M arginine pH 7.0 wash. By comparison, when 0.6 M arginine is replaced with 0.5 M NaCl in the gradient elution at pH 7.5, elution of etanercept was greatly reduced. FIG. 14 shows the elution profile at pH 7.5 during the salt gradient to 0.5 M NaCl. Two peaks were observed during the gradient, containing mostly etanercept, but with a low yield. A large amount of etanercept was eluted in the final 1 M arginine wash indicating that the salt concentration of 0.5 M NaCl coupled with pH 7.5 was not optimal for separation of correctly folded etanercept from misfolded/ aggregated material. As noted above, 1 M arginine was highly effective in eluting correctly folded etanercept, although with presence of low mobility species. It is noted that modifying the salt elution gradient to apply a gradient of about 0 to about 1M NaCal and conducting elution at pH 8 results in excellent resolution of correctly folded etanercept vs high low mobility (misfolded/aggregated) species in early elution products of such gradient as shown in Example 12. It appears that hydrophobic contribution of etanercept binding to Capto Adhere is reduced at pH 8.0, resulting in effective elution of correctly folded etanercept with NaCl alone.

Example 11

Capto™ Adhere; Elution with Arginine/Nacl Gradients at pH 7.5

Figure 15:
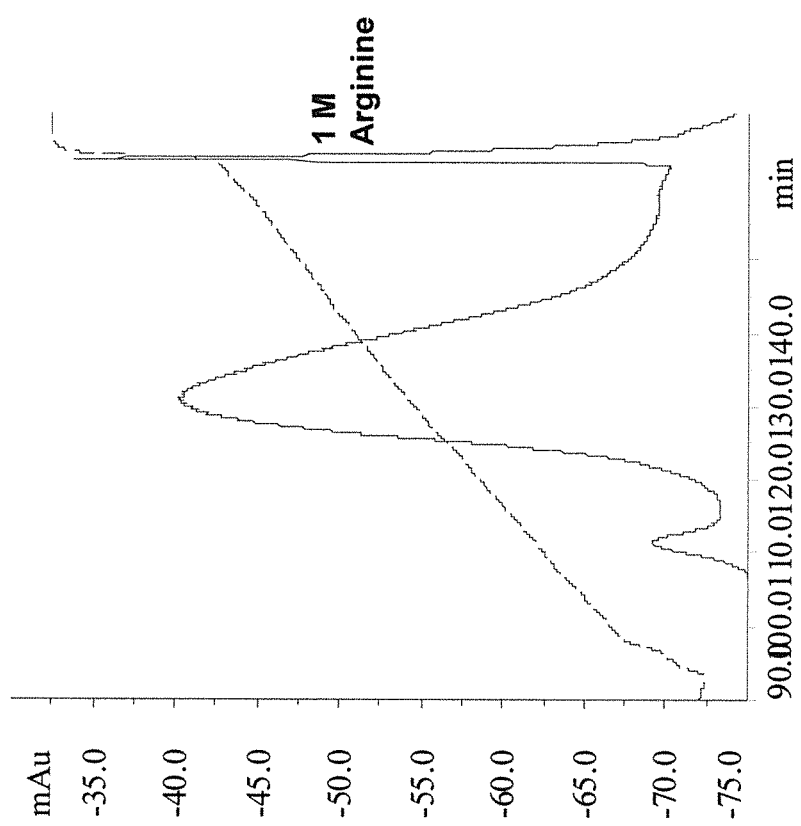
FIG. 15A (Elution profile of Capto-MMC pool from Capto-Adhere) shows a Chromatogram of elution by salt/arginine gradient at pH 7.5.
FIG. 15B. (Elution profile of Capto-MMC pool from Capto-Adhere) SDS-PAGE and native-PAGE of eluted samples wherein: Lane-0, standard; lane-1, Load; lane-2, FT; lane-3 to lane-6, eluted fractions; lane-7, 1 M arginine.
Figure 15B:
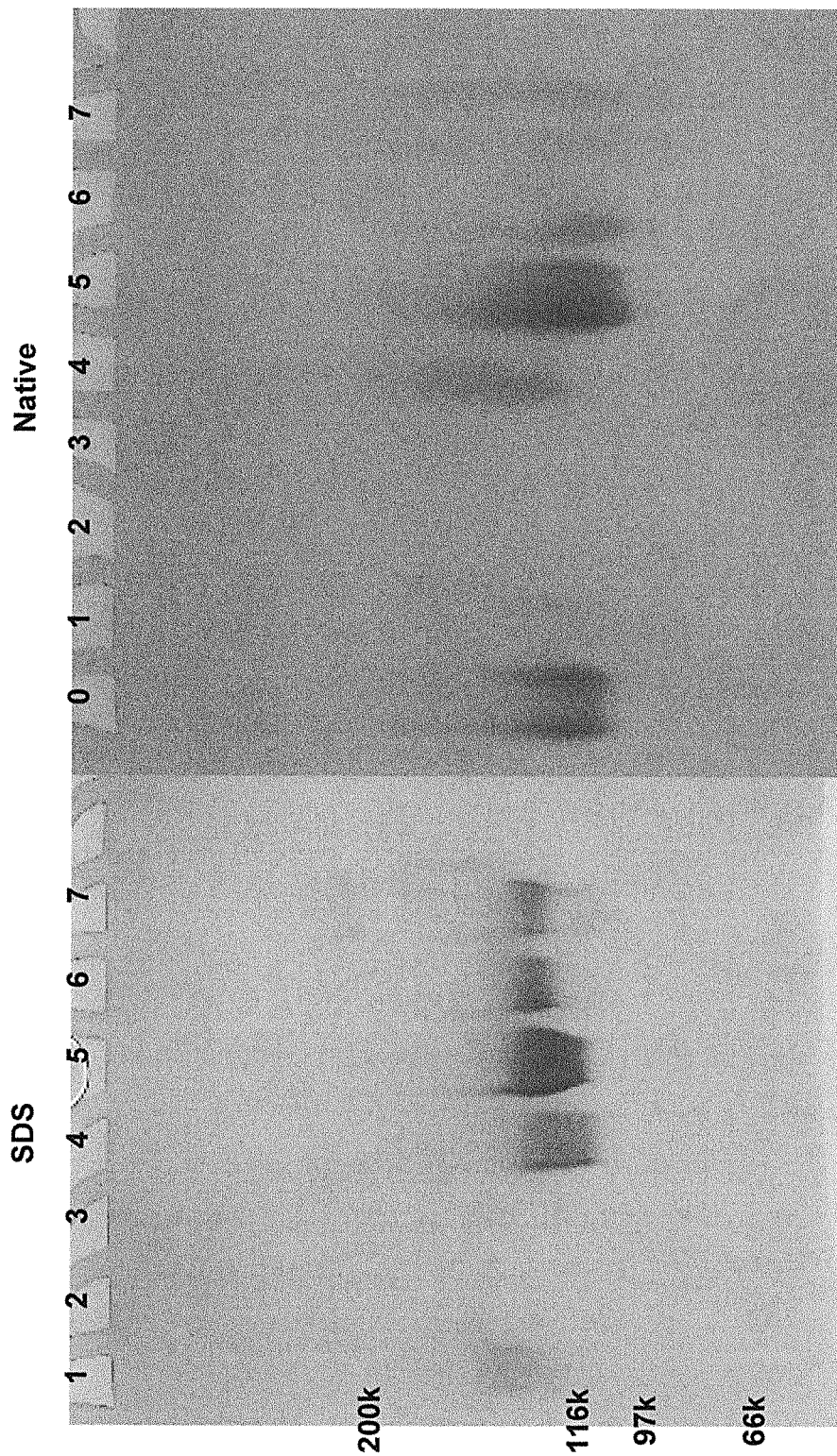
Figure 16:
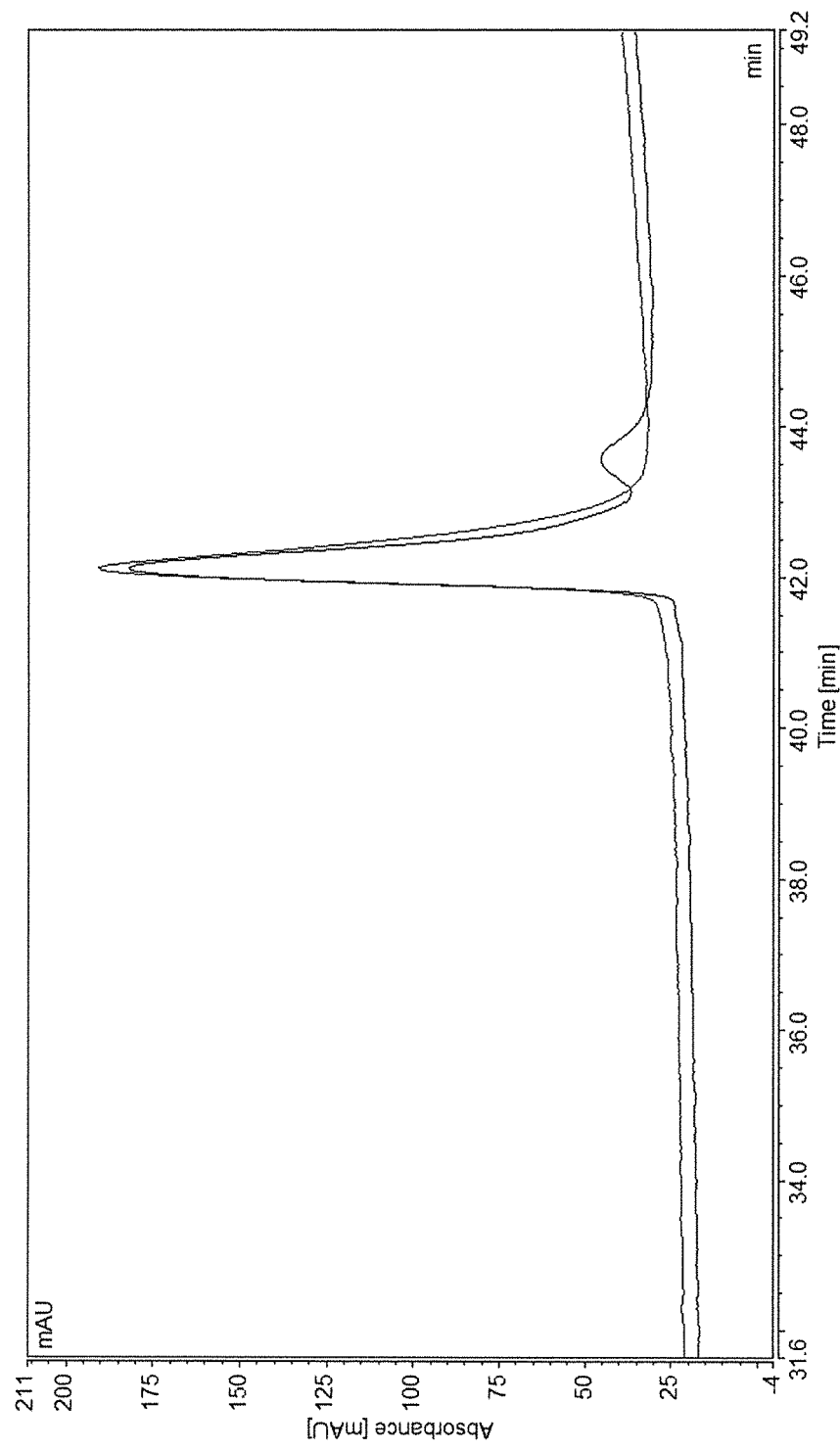
FIG. 16 is a HIC chromatogram corresponding to the etanercept material produced in Example 12, in which the plot exhibiting essentially no second smaller peak (misfolded material) corresponds to the material produced according to the present invention (example 12); and wherein the additional curve in the figure corresponding to commercially available etanercept, provided for comparative purposes, is seen to exhibit a second minor peak representing misfolded and/or aggregated material.

In this example a combined NaCl/arginine gradient is investigated at pH 7.5. Two such gradients were investigated: The first gradient that is investigated for the elution medium is one in which final NaCl and arginine concentrations are 0.4 and 0.2, respectively. A second gradient is then investigated in which the final NaCl and arginine concentrations are 0.25 M NaCl and 0.5 M arginine, respectively. In both instances the gradients are applied in a 10 mM phosphate, pH 7.5 solution. The first gradient was still too weak to reduce hydrophobic interactions and hence elute etanercept. The second gradient was more effective, as indicated by a smaller peak in the final 1 M arginine wash. In particular, as confirmed with SDS-PAGE, elution of etanercept occurs throughout the second tested gradient up to 0.25 M NaCl, 0.5 M arginine without high molecular weight (low mobility/misfolded/aggregated) species. This high molecular weight species is then eluted in the final 1 M arginine wash. On native-PAGE, a majority of native correctly folded etanercept is shown to elute in the middle fraction. A smearing band was observed with the 1 M arginine wash. It is therefore evident that a combination of arginine and NaCl can lead to elution of etanercept and separation of low mobility and high molecular weight species, corresponding to the misfolded species. HIC analysis of the Capto™ Adhere fractions for the Capto™ MMC pools (60-80% pure) shows that the eluted fractions during gradient (except for the tail fractions) normally gave a purity greater than 95%. Analyses of the eluates obtained in this example are represented in FIGS. 15A and 15B.

Example 12

Capto™ Adhere and Capto™ MMC

In this example, a Protein A eluate comprising correctly folded and misfolded etanercept was obtained by a method similar to the Protein A method described above. The eluate was subsequently applied to a Capto™ MINICe column, and the product pool was then applied to a Capto™ ADHERE column to provide a superior etanercept product, both quantitatively and qualitatively.

STEP 1. Cell Expanson. In a manner known in the art, cell expansion necessary to generate a sufficient number of cells for inoculation of a production bioreactor is performed using a clone of CHO cells expressing the etanercept fusion protein. The product of this expresson process (a harvested cell culture fluid) results in a mixture of correctly folded etanercept, as well as incorrectly folded and/or aggregated etanercept, along with additional impurities. The harvested cell culture fluid comprising such protein mixture is subjected to detergent viral inactivation.

STEP 2. Affinity Chromatography. Affinity chromatography is performed on the harvested cell culture obtain in Step 1 above using a conventional Protein A affinity column in a well known manner. Product recovery is approximately 85%. The product obtained is a complex protein mixture comprising correctly folded etanercept, incorrectly folded etanercept, and/or aggregates of correctly and/or incorrectly folded etanercept, or protein fragments. The product obtained from this Protein A affinity column purification step is adjusted to pH 3.5 and then subjected to a viral inactivation step. Following viral inactivation the product is adjusted to pH 5.5 and then further clarified in a known manner using a commercially obtained capsule filter.

STEP 3A. Mixed-Mode Cation Exchange Chromatography. A 31.8 L (45 cm diameter×20 cm bed height) packed bed GE Healthcare Capto MMC chromatography column is used to purify the product obtained in Step 2 above. Prior to use, the column is equilibrated with 2 CV of 25 mM acetate pH 5.5 and sanitized with 2 CV of 0.1 N NaOH, 1 M NaCl and neutralized with 2 CV of 25 mM acetate, 0.7 M NaCl, pH 5.5. The column is then equilibrated with 8-10 CV of 25 mM acetate pH 5.5 until the effluent is pH 5.5 and 3.5 mS/cm. The Protein A pool from step 2 above is diluted to <6 mS/cm with WFI and applied to a column loading of up to 15 g/L media for each cycle. The column is operated at a linear velocity of 200 cm/h to give a 6 minute residence time. After loading, the column is washed with 2 CV of 25 mM acetate pH 5.5. The product is then eluted with an 8.5 CV, 15% to 85% gradient of 25 mM acetate pH 5.5 to 25 mM acetate, 0.7 M NaCl, pH 5.5. Product collection begins at 0.15 OD (A280, 1.0 cm path length) and collection ends at 50% of peak maximum. The eluate volume is approximately 5 CV. Residual product and contaminants are stripped from the column with 2 CV of 10 mM Tris, 1 M NaCl, pH 8.0 and discarded. The product obtained from the mixed mode column is filtered using a Millipore Opticap XL10, 0.22 µm Durapore capsule filter, (0.69 m$^2$). The product obtained from this step represents a recovery of about 70% of the Protein A material obtained in Step 2.

Figure 12:
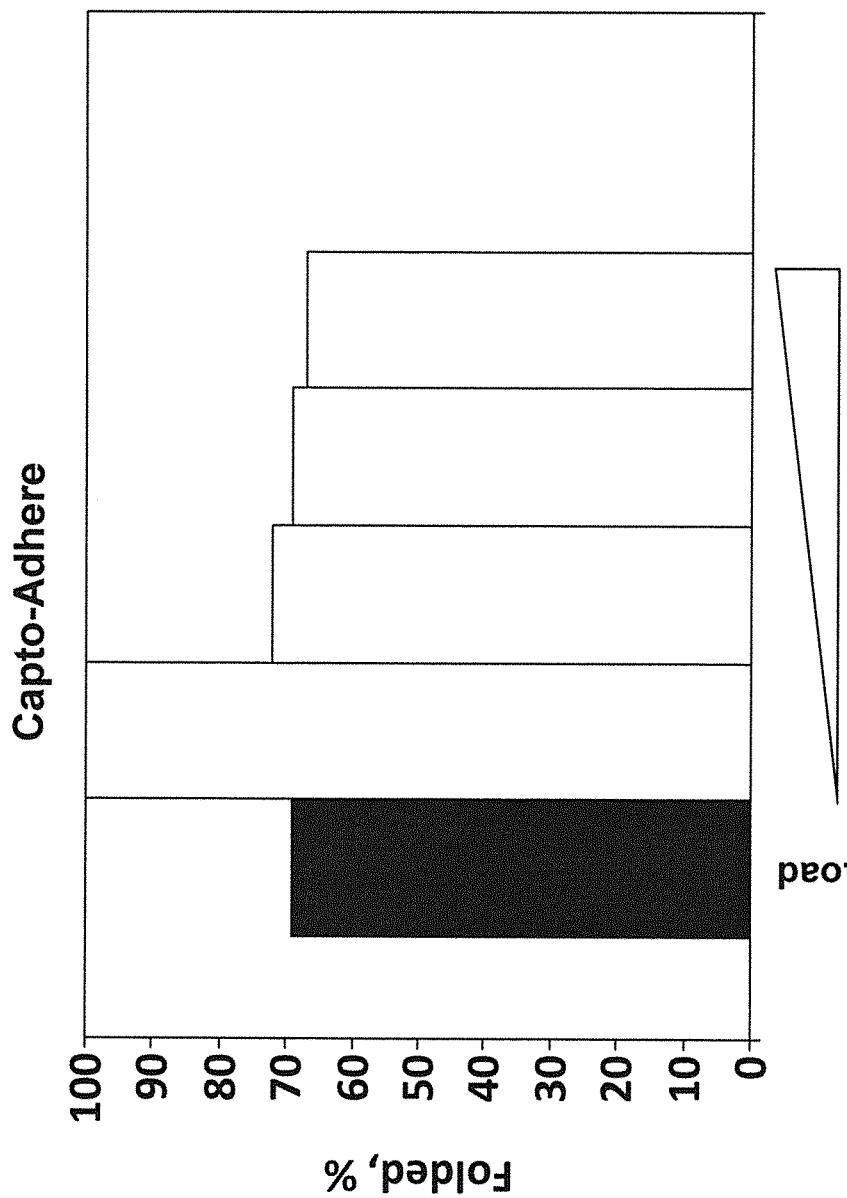
FIG. 12 is a schematic representation of HIC (hydrophobic interaction chromatography) analysis of Capto-Adhere mixed mode resin elution fractions obtain in step 3B of example 12 wherein the load sample is the material obtained in step 3A of example 12. Percentage of correctly folded etanercept is indicated on the vertical axis, and application of the salt gradient over time is represented on the horizontal axis. An elution fraction obtained early in the gradient contains 100% correctly folded etanercept.

STEP 3B. Mixed Mode Anion Exchange Chromatopgraphy. A 27.0 L (45 cm diameter×17 cm bed height) packed bed GE Healthcare Capto Adhere chromatography column is used to further purify the product obtained in step 3A above. Prior to use, the column is equilibrated with 2 CV of 25 mM Tris, pH 8.0 and sanitized with 2 CV of 0.1 N NaOH, 1M NaCl and neutralized and equilibrated with 2 CV of 25 mM Tris, pH 8.0. Prior to product loading, the column is equilibrated with 3 CV of 10 mM Tris, pH 8.0. The Capto MMC pool from Step 3A above is adjusted to pH 8.1 with 0.045 kg of 1 M Tris, pH 8.3 per kg of pool. The product from Step 3A above was diluted in-line 1:3.8 with WFI to adjust the conductivity to 12.0 mS/cm and pH 8.0. The resulting material is then applied to a column loading of up to 15 g/L media. The column is operated at a linear velocity of 170 cm/h to give a 6 minute residence time. After loading, the column is washed with 2 CV of 25 mM Tris, pH 8.0. The product is then eluted with a 10 CV gradient (20% to 90%) of 25 mM Tris, pH 8.0 to 10 mM Tris, 1 M NaCl, pH 8.0. Product collection is started at 0.15 OD (A280, 1.0 cm path length) and collection ended at 25% of peak maximum. The eluate volume is 4-6 CV. The eluted product is filtered using a commercially available capsule filter and then subjected in a known manner to viral filtration and tangential flow filtration steps. Overall product recovery from step 3B (including the final viral and tangential flow filtration steps) was approximately 68%. Product recovery measured before the filtration steps was about 75%. A schematic representation of HIC data obtained on eluation fractions from this step are representing in FIG. 12.

Analysis: The final filtered product obtained in this example is found to have greater than about 90 wt % correctly folded etanercept as determined by HIC; less than 5 wt % incorrectly folded etanercept species as determined by HIC; less than about 3 wt % of clipped material by HIC analysis (believed to be fragments of etanercept in which the TNFR portion thereof has been truncated) and a combined amount of correctly and incorrectly folded etanercept of greater than 95 wt % as determined by size exclusion chromatography.

The fact that protein binding occurred in the presence of salting-out conditions suggests a possibility that hydrophobic interaction is not involved in etanercept binding Capto™ MMC and Capto™ Adhere, considering that hydrophobic protein binding to HIC normally requires strong salting-out. However, hydrophobic interaction may be facilitated in the presence of electrostatic interaction between the protein and these mixed mode resins. Thus, without wishing to be bound to any particular theory, the binding of etanercept to the mixed mode resin may be mediated through both electrostatic and hydrophobic interaction modes even in the absence of salting-out conditions. The analytical HIC clearly indicates that the misfolded species, which elutes at lower ammonium sulfate concentration, is more hydrophobic than the folded species. Assuming that both folded and misfolded species have an identical electrostatic property and bind equally well to the charged group of Capto™ MMC or Capto™ Adhere ligands, it is possible that the stronger hydrophobic contribution of the misfolded species cause them to bind tighter to the mixed mode resins, thus necessitating stronger elution conditions for the misfolded species as is observed in the preceding examples. For Capto™ MMC, this can be achieved at higher salt concentration, which may not be enough to significantly enhance hydrophobic interaction, but may be sufficient to break additional electrostatic interaction between the Capto™ MMC and both the correctly and incorrectly folded species. On the contrary, Capto™ Adhere appears to be more hydrophobic than Capto™ MMC, requiring arginine, or alternatively higher salt concentration with higher pH, to elute the correctly folded species. Higher arginine concentration or harsher conditions are required to elute the misfolded species.

While the present invention uses the terms "misfolded" or "incorrectly folded" or "improperly folded" interchangeably, it should also be understood that these terms are intended to also encompass aggregated species, in that the mixed mode resins are also found to be effective in removing aggregated species in the same elution fractions which are found to contain the misfolded species. In fact, etanercept forms disulfide-linked oligomers as seen in SDS-PAGE. Such oligomers are eluted mostly in 1 M arginine wash, indicating their stronger hydrophobic interaction with the resins. Accordingly, for etanercept, it appears that both Capto™ MMC and Capto™ Adhere can result in simultaneous removal of the misfolded and aggregated species. Removal of misfolded material and aggregates, whether covalent or non-covalent, is highly desired in order to provide for safer biopharmaceuticals due to the potential immunogenicity of aggregate material (whether correctly or incorrectly folded).

With regard to the effects of arginine in the preceding examples, it is evident that arginine (arginine hydrochloride) not only serves as a salt but also weakens hydrophobic interaction. Arginine is known in the art to suppress protein aggregation and surface adsorption. In addition, arginine interacts with aromatic groups and thereby interferes with aromatic-aromatic or aromatic-cation interaction between proteins or between proteins and the surface. Both Capto™ MMC and Capto™ Adhere possess an aromatic group which can contribute to protein binding. It could not have been predicted that such a mode of binding could be effectively disrupted by arginine, but not NaCl. Arginine also weakens interaction between fatty acids, suggesting that it can disrupt hydrophobic interaction, not mediated through aromatic groups. The hydrophobic nature of arginine, although not clearly understood mechanistically, can thus play an important role in modulating protein-protein interaction and surface adsorption and hence protein elution from the mixed mode resin. However, as shown in example, 12 above, it is not necessary to use arginine in order to practice the present invention to provide an extremely high purity etanercept preparation. This is perhaps due to weak hydrophobic contribution of Capto MMC and Capto Adhere resins to protein binding. Nevertheless, use of arginine in combination with NaCl may improve the recovery and resolution of mixed mode chromatography for proteins.

Further Representative Embodiments Provided Below

A. A mixed mode chromatography method for separating a correctly folded protein from an incorrectly folded protein, comprising the steps of:
(a) binding a first protein mixture comprising both correctly folded and incorrectly folded conformations of a given protein to a mixed mode chromatography resin having both ion exchange moieties and hydrophobic moieties;
(b) eluting the correctly folded protein from the mixed mode resin to obtain a second protein mixture comprising a higher proportion of correctly folded protein than the first protein mixture.

B. The method of embodiment A wherein the mixed mode chromatography resin is a Capto™ MMC mixed mode chromatography resin.

C. The method of embodiment A wherein the mixed mode chromatography resin is a Capto™ Adhere mixed mode chromatography resin.

D. The method of any of embodiments A-C wherein the correctly and incorrectly folded protein conformations comprise correctly folded and incorrectly folded etanercept.

E. The method of embodiment D wherein the incorrectly folded etanercept constitutes less than about 10 wt. %, and preferably less than about 5 wt. % of the eluate obtained in step (b); the correctly folded etanercept constitutes more than about 90 wt % and preferably more than about 95 wt % of the eluate obtained in step (b); and a combined amount of correctly folded and incorrectly folded etanercept constitutes at least about 95 wt. percent and preferably at least about 98 wt. % of the eluate obtained in step (b).

F. The method any of embodiments A to E wherein the mixed mode resin is Capto™ MMC and steps (a) and (b) of the method are conducted at a pH of between about 4.5 to about 7.5; and the elution step (b) is carried out by contacting the mixed mode resin with a salt solution.

G. The method of any of embodiments A to E wherein the mixed mode resin is Capto™ Adhere and steps (a) and (b) are conducted at a pH of about 4.5 to about 8.5; and the elution step (b) is carried out by contacting the mixed mode resin with a salt solution, said solution optionally further comprising arginine.

H. The method of embodiments F or G wherein the salt solution is applied in step (b) through a gradient whereby the salt concentration is gradually increased.

I. The method of embodiment H wherein the salt concentration gradient of step (b) causes an increase in the salt concentration of from about 0 to about 1M.

J. The method of any of embodiments F through I wherein the salt is selected from sodium chloride and sodium sulfate.

K. The method of any of embodiments A through J wherein, during step (b), the pH of the solution contacting the resin in step (b) is gradually changed.

L. The method of embodiment K wherein the pH is gradually increased.

M. The method of embodiment K wherein the pH is gradually decreased.

N. The method of any of embodiments A to M wherein the amount of correctly folded protein obtained in the eluate of step (b) is at least about 60 wt % of the amount of protein present in the protein mixture introduced to the resin in step (a).

O. The method of embodiment N wherein the amount of correctly folded protein is at least about 70 wt. % of the amount of protein present in the protein mixture introduced to the resin in step (a).

P. The method of any of embodiments A-O in which a protein mixture comprising at least 90 wt % correctly folded etanercept and preferably less than about 5 wt. % incorrectly folded etanercept is obtained without performing, or without need to perform any chromatographic separation or purification steps to separate correctly folded from incorrectly folded etanercept, other than the following:
  (1) one or more purification steps, preferably comprising a protein A chromatographic purification step, where such step(s) are employed to purify a harvest cell culture fluid containing etanercept-based proteins, and where such purification step does not any appreciable separation of correctly from incorrectly folded etanercept.
  (2) the mixed mode chromatographic steps (a) and (b) recited in embodiment 1; and
  (3) SEC, HIC or other analytical chromatographic steps performed solely for purposes of analysis.

Q. The method of any of embodiments A through P wherein the amount of protein present in the eluate of step (b) is determined by UV absorbance at A 280; the amount of correctly folded etanercept in the eluate of step B is determined by hydrophobic interaction chromatography; and the combined amount of correctly and incorrectly folded etanercept present in the eluate of step (b) is determined by size exclusion chromatography.

R. A mixed mode chromatography method for purifying a protein mixture in order to separate correctly folded etanercept from incorrectly folded etanercept present in said mixture, the method comprising the steps of:
  (a) contacting a mixed mode chromatography resin having hydrophobic moieties and ion exchange moieties with a solution containing a protein mixture comprising correctly folded etanercept and incorrectly folded etanercept, such that both the correctly and incorrectly folded etanercept become affixed to, bound or captured upon the mixed mode chromatography resin; and
  (b) contacting the mixed mode resin with a solution capable of eluting the etanercept proteins from the mixed mode chromatography resin to obtain an eluate in which the ratio of the amount of correctly folded etanercept to incorrectly folded etanercept is greater than that of the protein mixture introduced to the resin in step (a).

S. The method of embodiment R wherein the mixed mode chromatography resin is a Capto™ MMC mixed mode chromatography resin.

T. The method of embodiment R wherein the mixed mode chromatography resin is a Capto™ Adhere mixed mode chromatography resin.

U. The method of embodiments A-T wherein
  (A) incorrectly folded etanercept constitutes less than about 5 wt. percent of the eluate obtained in step (b); correctly folded etanercept constitutes more than about 90 wt % of the eluate obtained in step (b); and a combined amount of correctly folded and incorrectly folded etanercept constitutes at least about 95 wt. percent of the eluate obtained in step (b); or
  (B) the eluate, or portion thereof, obtained in step (b) comprises correctly folded etanercept and is free or essentially free of incorrectly folded etanercept.

V. The method any of embodiments A to U wherein the mixed mode resin is Capto™ MMC and steps (a) and (b) of the method are conducted at a pH of between about 4.5 to about 7.5; and the elution step (b) is carried out by contacting the mixed mode resin with a salt solution.

W. The method of any of embodiments R to V wherein the mixed mode resin is Capto™ Adhere and steps (a) and (b) are conducted at a pH of about 4.5 to about 8.5; and the elution step (b) is carried out by contacting the mixed mode resin with a salt solution, said solution optionally further comprising arginine.

X. The method of embodiments V or W wherein the salt solution is applied in step (b) through a gradient whereby the salt concentration is gradually increased.

Y. The method of embodiment X wherein the salt concentration gradient of step (b) causes an increase in the salt concentration of from about 0 to about 1M.

Z. The method of any of embodiments V through Y wherein the salt is selected from sodium chloride and sodium sulfate.

AA. The method of any of embodiments R through Z wherein, during step (b), the pH of the solution contacting the resin in step (b) is gradually increased or gradually decreased.

BB. The method of any of embodiments R to AA wherein the amount of correctly folded protein obtained in the eluate of step (b) is at least about 60 wt % and preferably at least of about 70 wt. % of the amount of protein present in the protein mixture introduced to the resin in step (a).

CC. The method of any of embodiments A to BB, wherein the method is practiced two or more times in the following manner:
  performing a first mixed mode separation (separation #1) by carrying out steps (a) and (b); followed by
  performing a second mixed mode separation (separation #2): by carrying out steps (a) and (b) again;
  wherein the eluate obtained in step (b) of separation #1 is used as the solution containing a protein mixture in step (a) of separation #2.

DD. The method of embodiment CC wherein the mixed mode resin used in separation #1 is the same as, or different from, the mixed mode resin used in separation #2.

EE. The method of embodiment DD wherein separation #1 and separation #2 are carried out in a manner selected from the following combinations:
  Separation #1 uses CAPTO MMC as the mixed mode chromatography resin and
  Separation #2 uses CAPTO ADHERE as the mixed mode chromatography resin; - - -
  Separation #1 uses CAPTO ADHERE as the mixed mode chromatography resin and
  Separation #2 uses CAPTO MMC as the mixed mode chromatography resin; - - -
  Separation #1 uses CAPTO MMC as the mixed mode chromatography resin and
  Separation #2 uses CAPTO MMC as the mixed mode chromatography resin; or - - -
  Separation #1 uses CAPTO ADHERE as the mixed mode chromatography resin
  Separation #2 uses CAPTO ADHERE as the mixed mode chromatography resin.

FF. The method of embodiment EE wherein separation #1 and separation #2 are carried out in the following manner: Separation #1 uses CAPTO MMC as the mixed mode chromatography resin; and Separation #2 uses CAPTO ADHERE as the mixed mode chromatography resin.

GG. An etanercept-containing protein mixture, or a pharmaceutically acceptable formulation comprising said mixture, obtained by the method of any of embodiments A to FF and wherein said protein mixture comprises correctly folded etanercept in amount constituting greater than about 90 wt. % of the protein mixture; and comprising incorrectly folded etanercept in an amount constituting less than about 5 wt % of the protein mixture; and wherein the protein mixture has a combined amount of correctly folded and incorrectly folded etanercept constituting at least about 95 and preferably at least about 98 wt. % of the etanercept-containing protein mixture.

HH. A pharmaceutically acceptable formulation containing highly pure etanercept suitable for administration to a subject requiring treatment for a TNF alpha mediated condition, said formulation containing a protein mixture comprising a major amount of correctly folded etanercept and a minor amount of incorrectly folded etanercept, wherein:
  (i) the incorrectly folded etanercept constitutes less than about 10 wt. %, preferably less than about 8 wt. % and most preferably less than about 5 wt. % of the protein mixture;
  (ii) the correctly folded etanercept constitutes more than 90 wt. % and preferably more than about 92 wt % and preferably more than about 95 wt % of the protein mixture; and
  (iii) the total amount of correctly folded etanercept and incorrectly folded etanercept (but not including aggregates thereof) constitutes at least 95 and preferably at least 98% by weight of the protein mixture;
wherein the formulation further comprises pharmaceutically acceptable inactive ingredients, excipients or carriers rendering the formulation suitable for administration to the subject.

II. The formulation of embodiment HH wherein the etanercept preparation constitutes about 25 to about 75 mg/ml of the formulation, and the formulation further comprises sucrose, sodium chloride, L-arginine hydrochloride, and sodium phosphate.

JJ. A method for producing an etanercept-containing protein mixture having high purity with respect to the amount of correctly folded versus incorrectly folded etanercept present therein, said method comprising the steps of:
  (1) expressing etanercept in a mammalian expression system to obtain a harvest cell culture fluid containing an etanercept-containing protein mixture comprising both correctly folded and incorrectly folded etanercept;
  (2) subjecting the harvest cell culture fluid obtained in step 1 to a purification process whereby an etanercept-containing protein mixture is obtained with a reduced amount of, or substantially free of, undesired impurities present in the harvest cell culture fluid produced in step (1);
  (3) contacting the etanercept-containing protein mixture obtained in step (2) one or more times with a mixed mode chromatographic resin having both ion exchange moieties and hydrophobic interaction moieties in order to affix proteins contained in the mixture to the resin; and
  (4) contacting the resin having protein bound thereon from step 3 with a solution to elute correctly folded etanercept from the mixed mode resin to obtain an eluate comprising an etanercept-containing protein mixture having a higher proportion of correctly folded etanercept versus incorrectly folded etanercept than the etanercept-containing mixture introduced to the resin in step 3;
wherein:
  (i) the amount of protein present in the etanercept-containing protein mixture obtained from purification of step 2 is at least about 80 wt % of the amount of the etanercept-based protein mixture present in the harvest cell culture fluid obtained in step 1.
  (ii) the combined amount of correctly and incorrectly folded etanercept protein present in the protein mixture eluted in step 4 is at least about 60 wt. % of the amount thereof present in the protein mixture obtained from step 2;
  (iii) the amount of correctly folded etanercept present in the eluate of step 4 is at least about 30 wt. %, and preferably at least about 35 wt % of the amount of etanercept-containing protein mixture present in the harvest cell culture fluid obtained in step 1; and
  (iv) said correctly folded etanercept constitutes at least about 90 wt % and preferably at least about 95 wt. % of the eluate obtained in step 4.

KK. The method of embodiment JJ wherein the mixed mode resin is selected from the group consisting of CAPTO MMC and CAPTO ADHERE.

LL. The method of embodiments JJ or KK comprising the following additional steps:
  Step (5): contacting the protein mixture obtained in the eluate of step 4 with a mixed mode chromatographic resin having both ion exchange moieties and hydrophobic interaction moieties in order to affix the proteins contained in the mixture to the resin, and then;
  step (6) contacting the resin with a solution to elute correctly folded etanercept therefrom to obtain an eluate comprising a protein mixture having a higher proportion of correctly folded versus incorrectly etanercept;
wherein the mixed mode resin used in said additional steps 5 and 6 is the same as, or different from the mixed mode resin used in steps 3 and 4.

MM. The method of embodiment LL wherein the mixed mode resin used in step (3) and (4) is CAPTO MMC and the resin used in steps (5) and (6) is CAPTO ADHERE.

NN. The method of any of embodiments JJ to MM wherein step 4 (and/or step 6 in the case of embodiment LL) is conducted by contacting the mixed mode resin with a salt solution in order to elute correctly folded etanercept from the mixed mode resin, and optionally (i) wherein the concentration of the salt solution is gradually increased in steps (4) or (6) during said contacting of the solution with the resin; and optionally (ii) the pH of the elution solution is gradually increased or decreased in steps (4) and/or (6) during said contacting of the solution with the resin.

OO. The method of any of embodiments JJ to NN, wherein product obtained in one or more of the steps of the method are subjected to filtration, such as viral filtration and/or tangential flow filtration.

PP. The method of any of embodiments JJ to OO, wherein step 2 is carried out using a protein A chromatography column.

QQ. The method of any of embodiments JJ to OO wherein step 2 is carried out using a mixed mode resin having hydrophobic and ion exchange moieties.

RR. The method of any of embodiments A-PP in which a protein mixture comprising at least 90 wt % correctly folded etanercept and preferably less than about 5 wt. % incorrectly folded etanercept is obtained without performing any chromatographic separation or purification steps to separate correctly folded from incorrectly folded etanercept, other than one or more of the following steps:
  (1) optionally, one or more purification steps, preferably comprising a protein A chromatographic purification step, such step(s) being employed to purify a harvest cell culture fluid containing etanercept-based proteins, wherein the purification step does not separate correctly from incorrectly folded etanercept;

(2) said one or more occurrences of the mixed mode chromatographic steps (3) and (4) recited in embodiment A (or steps 3, 4, 5 and 6 as per embodiment LL); and (3) optionally, one or more SEC, HIC or other chromatography steps performed solely for purposes of analysis.

SS. The method of any of embodiments A to RR which excludes use of single mode hydrophobic interaction chromatography as a means of separating correctly folded etanercept from incorrectly folded etanercept, except when performed solely for purposes of analysis.

TT. A method for treating a subject suffering from a TNF mediated disease, comprising the steps of administering to such individual a pharmaceutical formulation containing a protein mixture comprising correctly folded etanercept and incorrectly folded etanercept, said mixture being obtained by the method of any of embodiments A through SS wherein the amount of incorrectly folded etanercept in the protein mixture is less than about 5 wt % of said mixture.

UU. The method of embodiment TT, wherein the amount of incorrectly folded etanercept in the protein mixture is less than about 3 wt % of said mixture and amount of correctly folded etanercept in the mixture is greater than about 95 wt % of said mixture.

VV. A method for treating a subject suffering from a TNF mediated disease, comprising the steps of administering to such individual a pharmaceutical formulation containing a protein mixture comprising correctly folded etanercept and incorrectly folded etanercept wherein the amount of incorrectly folded etanercept in the protein mixture is less than about 5 wt % of said mixture.

WW. The method of embodiments TT-VV wherein the amount of incorrectly folded etanercept in the protein mixture is less than about 3 wt % of said mixture and the amount of correctly folded etanercept in the mixture is greater than about 95 wt % of the mixture.

XX. The method of any of embodiments TT-VV wherein the combined amount of correctly folded and incorrectly folded etanercept (excluding aggregates thereof) is at least about 95 wt % of said mixture.

YY. The method of embodiment XX wherein the combined amount of correctly folded and incorrectly folded etanercept (excluding aggregates thereof) is at least about 98 wt % of said mixture.

ZZ. The methods or compositions of any of embodiments A through YY wherein the term "incorrectly folded etanercept" is understood, unless otherwise noted, to include aggregates comprising correctly folded and/or incorrectly folded etanercept.

AAA. The method of embodiments JJ to QQ wherein the amount of etanercept based protein contained in the harvest cell culture of step 1 is determined by Fc elisa.

BBB. The method of any of embodiments JJ-QQ wherein the amount of etanercept-based proteins present in the eluates obtained from the mixed mode resin in step 4 (or as in the case of embodiment LL, steps 4 and 6) is determined by UV absorbance at A280.

CCC. The method of embodiment BBB wherein the amount of etanercept-based protein present in the product obtain from the purification process of step 2 is determined by UV absorbance at A280 or by Fc elisa.

DDD. A method for separating correctly folded etanercept from incorrectly folded etanercept, wherein chromatographic means are used to achieve such separation, and wherein the chromatographic means consist solely or essentially of mixed mode chromatography in which a mixture comprising correctly folded and incorrectly folded etanercept is contacted with a mixed mode chromatographic resin having ion exchange and hydrophobic moieties, and then eluted therefrom, to obtain an eluate comprising at least about 85 and preferably at least about 90, and most preferably at least about 95 wt % correctly folded etanercept.

EEE. The method of embodiment DDD wherein the mixed mode resin is selected from CAPTO MMC and CAPTO ADHERE; the elution is conducted with a salt solution, optionally applied using a gradient of increasing salt concentration; the pH of the salt solution is in the range of about 4 to about 8.5, applied optionally in a gradient in which the pH is gradually increased or decreased; and wherein the eluate is obtained from the resin over a period of time, and eluate collected early in said period is free or essentially free of incorrectly folded etanercept.

What is claimed is:

1. A method of reducing incorrectly folded etanercept in and stabilizing an aqueous injectable pharmaceutical formulation containing about 25 to about 75 mg/ml correctly-folded etanercept, comprising:
    a) removing incorrectly folded and aggregated etanercept from an etanercept-containing protein mixture using a mixed-mode chromatography procedure configured to produce an etanercept-containing composition such that the amount of said incorrectly folded etanercept is less than 5 wt % of said composition and wherein the amount of said correctly folded etanercept is greater than 95 wt %, wherein said incorrectly folded etanercept is an etanercept protein that has a conformation different from that of the correctly folded etanercept and said different conformation renders said incorrectly folded etanercept protein lacking in biological activity as a TNF inhibitor and said incorrectly folded etanercept is not an aggregate, wherein said mixed-mode chromatography procedure comprises binding correctly folded etanercept and incorrectly folded etanercept to a mixed-mode chromatography resin having both ion exchange and hydrophobic moieties and contacting the mixed-mode chromatography resin to elute with a salt solution at a pH between 4.5 and 8.5; and
    b) combining the etanercept-containing composition formed in step (a) with a correctly folded etanercept-stabilizing formulation comprising about 0.1 to about 2 weight percent of a combination of sugar and an amino acid wherein the amino acid is not arginine and is not cysteine, 0 to about 25 mM NaCl, and an aqueous buffer selected from the group consisting of phosphate, histidine, citrate, maleate, tartrate, acetate, tris-(hydroxymethyl)-aminomethane (tris), and bicarbonate to form the aqueous injectable pharmaceutical formulation containing about 25 to about 75 mg/ml etanercept, wherein the aqueous injectable pharmaceutical formulation has a pH of about 6.2 to 7.4 and does not contain cysteine and does not contain arginine, and wherein the correctly folded etanercept-stabilizing formulation stabilizes said correctly-folded etanercept in said etanercept-containing composition such that the aqueous injectable pharmaceutical formulation is less immunogenic than a commercially available etanercept-containing composition and contains less incorrectly folded etanercept than a commercially available etanercept-containing composition.

2. The method of claim 1, wherein the aqueous injectable pharmaceutical formulation comprises about 0.1 to about 2 wt % of a combination of sucrose with alanine, glycine, or lysine; and about 10 mM to about 200 mM of one or more tonicity modifiers selected from potassium chloride, sodium sulfate, and sodium citrate.

3. The method of claim 1, wherein less than 3 wt % of the etanercept in the etanercept-containing composition is incorrectly folded etanercept.

4. The method of claim 1, wherein less than 1 wt % of the etanercept in the etanercept-containing composition is incorrectly folded etanercept.

5. The method of claim 1, wherein less than 5 wt % of the etanercept in the etanercept-containing composition is incorrectly folded etanercept, fragments of etanercept, and aggregated etanercept.

6. The method of claim 1, wherein the aqueous injectable pharmaceutical formulation further comprises sodium citrate.

7. The method of claim 6, wherein the aqueous injectable pharmaceutical formulation comprises about 10 mM to about 200 mM of the sodium citrate.

8. The method of claim 1, wherein the aqueous injectable pharmaceutical formulation comprises about 0.1 to about 2 wt % of a combination of sucrose and lysine, and about 25 mM sodium chloride.

9. The method of claim 8, wherein the aqueous injectable pharmaceutical formulation does not contain any amino acid other than lysine.

10. The method of claim 9, wherein the aqueous buffer is citrate buffer.

11. The method of claim 1, wherein the eluting step comprises a NaCl gradient ranging from 0 to 0.5M NaCl and/or a pH gradient in a range of pH 4.5 and pH 8.

12. The method of claim 1, wherein the eluting step comprises a NaCl gradient ranging from 0 to 0.25M NaCl and an arginine gradient ranging from 0 to 0.5M arginine.

13. The method of claim 1, wherein hydrophobic interaction chromatography (HIC) is not used to separate said incorrectly folded etanercept from said correctly folded etanercept.

14. A method of treating a tumor necrosis factor (TNF) mediated disease in a patient comprising administering to said patient the aqueous injectable pharmaceutical formulation prepared according to claim 1.

15. The method of claim 14, comprising administering 25-100 mg etanercept per dose to the subject.

16. The method of claim 14, comprising injecting the aqueous injectable pharmaceutical formulation subcutaneously or intramuscularly.

17. The method of claim 14, wherein less than 3 wt % of the etanercept in the etanercept-containing composition is incorrectly folded etanercept.

18. A method of treating a subject in need of treatment for rheumatoid arthritis, psoriatic arthritis ankylosing spondylitis, Crohn's disease, chronic obstructive pulmonary disease (COPD), asthma, or atopic dermatitis comprising administering to the subject the aqueous injectable pharmaceutical formulation prepared according to claim 1.

19. The method of claim 18, comprising administering 25-100 mg etanercept per dose to the subject.

20. The method of claim 19, wherein the administering comprises injecting the aqueous etanercept composition subcutaneously or intramuscularly.

21. A vial, syringe, or injector pen containing the aqueous injectable pharmaceutical formulation prepared according to claim 1.

22. The vial, syringe, or injector pen of claim 21, wherein less than 3 wt % of the etanercept in the etanercept-containing composition is incorrectly folded etanercept.

* * * * *